(12) United States Patent
Tyler et al.

(10) Patent No.: US 9,828,341 B2
(45) Date of Patent: Nov. 28, 2017

(54) DENDRITIC CORE COMPOUNDS

(71) Applicant: Victoria Link Limited, Wellington (NZ)

(72) Inventors: Peter Charles Tyler, Wellington (NZ); Olga Vladimirovna Zubkova, Waikanae Beach (NZ)

(73) Assignee: Victoria Link Limited, Wellington (NZ)

( * ) Notice: Subject to any disclaimer, the term of this patent is extended or adjusted under 35 U.S.C. 154(b) by 140 days.

(21) Appl. No.: 14/646,807

(22) PCT Filed: Nov. 28, 2013

(86) PCT No.: PCT/NZ2013/000215
§ 371 (c)(1),
(2) Date: May 22, 2015

(87) PCT Pub. No.: WO2014/084743
PCT Pub. Date: Jun. 5, 2014

(65) Prior Publication Data
US 2015/0291522 A1 Oct. 15, 2015

(30) Foreign Application Priority Data
Nov. 28, 2012 (NZ) ........................ 603908

(51) Int. Cl.
*C07D 207/46* (2006.01)
*C07C 235/08* (2006.01)
*C07C 235/12* (2006.01)
*C07C 237/22* (2006.01)

(52) U.S. Cl.
CPC .......... *C07D 207/46* (2013.01); *C07C 235/08* (2013.01); *C07C 235/12* (2013.01); *C07C 237/22* (2013.01)

(58) Field of Classification Search
None
See application file for complete search history.

(56) References Cited

U.S. PATENT DOCUMENTS

| 5,104,815 | A | 4/1992 | Garner et al. |
| 6,030,640 | A | 2/2000 | Shimizu et al. |
| 2003/0097019 | A1 | 5/2003 | Newkome et al. |
| 2005/0008571 | A1 | 1/2005 | Newkome et al. |
| 2010/0272660 | A1 | 10/2010 | Malle |

FOREIGN PATENT DOCUMENTS

| EP | 0891875 B1 | 10/2003 |
| JP | H11152256 A | 6/1999 |
| WO | WO9525736 A1 | 9/1995 |
| WO | WO0220469 A1 | 3/2002 |

OTHER PUBLICATIONS

Naidoo et al., Bidirectional solid phase synthesis of a model oligoglycine bolaamphiphile and purification by rapid self-assembly, J Pept Sci. May 2012;18(5):317-25.
Shimizu et al., Noncovalent Formation of Polyglycine II-Type Structure by Hexagonal Self-Assembly of Linear Polymolecular Chains, Japan J. Am. Chem. Soc., 1997, 119 (26), pp. 6209-6210.
Desaraju et al., Synthesis and iron complexation studies of bis-hydroxamic acids, Journal of Coordination Chemistry (1986), 14(3):241-248.
Kogiso et al., Dicarboxylic Oligopeptide Bolaamphiphiles: Proton-Triggered Self-Assembly of Microtubes with Loose Solid Surfaces, Langmuir (1998), 14(18):4978-4986.
Shimizu et al., Organic Supramolecular Self-Assembled Materials Stabilized by Multiple Hydrogen Bonds, Transactions of the Materials Research Society of Japan (1999), 24(3):431-436.

*Primary Examiner* — Alicia L Otton
*Assistant Examiner* — Po-Chih Chen
(74) *Attorney, Agent, or Firm* — Glenn J. Foulds; Bozicevic, Field & Francis LLP

(57) ABSTRACT

The invention relates to compounds that are useful for the preparation of dendrimer compounds, the use of these compounds for preparing dendrimers and processes for preparing the compounds.

20 Claims, No Drawings

DENDRITIC CORE COMPOUNDS

TECHNICAL FIELD

This invention relates generally to compounds that are intermediates for the preparation of dendrimer compounds, the use of these compounds for preparing dendrimers and processes for preparing the compounds.

BACKGROUND

Interest in dendritic compounds has grown in recent times, and dendrimers have found application in a wide range of areas, such as pharmaceuticals, drug delivery, gene delivery, sensor technologies (cation photodetection and fluorescence signal quenching), in the synthesis of monodisperse metallic nanoparticles, in environmental remediation, as blood substitutes usually in the oxygen-carrying sense (oxygen therapeutics) and plasma substitutes (volume expenders).

Dendritic structures tend to be complex. However, for some applications, such as pharmaceuticals, it is desirable to employ compounds that are discrete, well-characterised, single entities. This can be an issue in the dendrimer space, so it is desirable to use intermediates and processes which produce such single entities. There is therefore a need for simple dendritic cores that can be used to prepare dendritic compounds for use in certain applications.

Newkome et al. (*Macromolecules*, 1993, 26, 2394-2396) have described the synthesis of a dodecaacid dendritic core, starting from the tetraacid compound (structure shown in Scheme 1, below) and coupling this with a branched amine. This produced a compound with twelve terminal acids (attachment points), which was further elaborated (through five generations) to produce dendrimers having up to 972 terminal acids.

Newkome et al. (*J. Org. Chem.* 2002, 67, 3957-3960) have also reported the synthesis of a tetraamine (amine terminated) dendritic core, starting from the tetraacid compound. The tetraamine core was further elaborated by reaction with excess acrylonitrile to generate an octanitrile as an oily product.

Hukkamäki et al. (Hukkämaki, J.; Pakkanen, T. T. *Journal of Molecular Catalysis A: Chemical* 2001, 174, 205-21,) have also described the synthesis of the same amine terminated dendritic core. The tetraamine core was further elaborated by reaction with acrylonitrile to produce a (two generation) dendrimer having eight terminal amine groups.

For the synthesis of simple, well-defined dendritic molecules as single compounds, it would be desirable to employ a simple, stable dendritic core as an intermediate which could provide a route to the synthesis of, for example, dendrimers having pharmaceutical uses.

It is therefore an object of the present invention to provide intermediate compounds for the preparation of dendritic compounds, or to at least provide a useful choice.

SUMMARY OF INVENTION

In a first aspect, the invention provides a compound of formula (I)

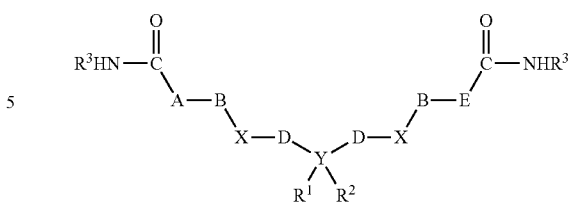

wherein:
Y is O;
B is O;
$R^1$ and $R^2$ are absent; and
either A, E, D and X are all $CH_2$; or A, D and X are all $CH_2$ and E is $(CH_2CH_2O)_t{}^\#CH_2$ wherein $^\#$ indicates a point of attachment of E to its adjacent carbonyl group;
t is an integer from 1 to 10;
or wherein:
Y is C;
$R^1$ and $R^2$ are both H; and
A, E, B and D are $CH_2$ and X is O;
or wherein:
Y is C;
A is $(CH_2)_u$
$R^1$ and $R^2$ are both H;
B, X, D and E are all absent; and
u is an integer from 1 to 10;
or wherein:
Y is C;
X is O;
B is $(CH_2)_p$;
A, E and D are all $CH_2$; and
$R^1$ is H, NHZ or $C_{1-6}$alkyl and $R^2$ is a radical of formula (i) or a radical of formula (ii)

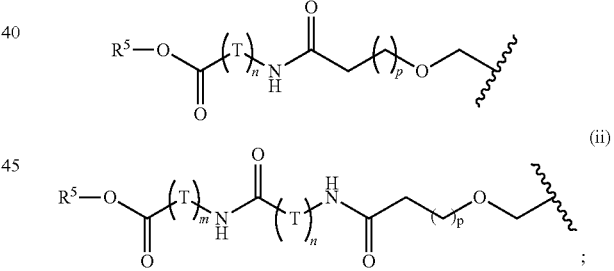

Z is H, acyl, $C(O)(CH_2)_wN(H)G$, $*CH_3*C(O)$— where $*C$ denotes $^{13}C$ or $^{14}C$, 5-TAMRA (4-carboxytetramethylrhodamine), Fluorescein (resorcinolphthalein), Alexa Fluor 350 (7-amino-4-methyl-6-sulfocoumarin-3-acetic acid), BODIPY (4,4-difluoro-4-bora-3a,4a-diaza-s-indacene) or Alkyne MegaStokes dye 608 (1-{3-{[4-(2-cyclooctyn-1-ylmethyl)benzoyl]amino}propyl}-4-{2-[4-(dimethylamino)phenyl]ethenyl}pyridinium hexafluorophosphate);
w is an integer from 1 to 11;
G is H, acyl, Boc (t-butoxycarbonyl), Troc (2,2,2-trichloroethyloxycarbonyl), Fmoc (9-fluorenylmethoxycarbonyl), Cbz (benzyloxycarbonyl),$*CH_3*CO$— where $*C$ denotes $^{13}C$ or $^{14}C$, 5-TAMRA (4-carboxytetramethylrhodamine), Fluorescein (resorcinolphthalein), Alexa Fluor 350 (7-amino-4-methyl-6-sulfocoumarin-3-acetic acid), BODIPY (4,4-difluoro-4-bora-3a,4a-diaza-s-indacene) or Alkyne MegaStokes dye 608 (1-{3-{[4-(2-cyclooctyn-1- ylmethyl)benzoyl]amino}propyl}-4-{2-[4-(dimethylamino) phenyl]ethenyl}pyridinium hexafluorophosphate);
or wherein:
Y is C;
X is O;
B is $(CH_2)_p$;
A, E and D are all $CH_2$; and
$R^1$ and $R^2$, both the same, are a radical of formula (i) or a radical of formula (ii)

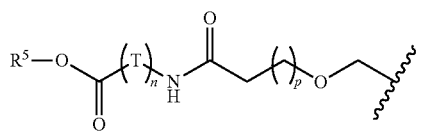

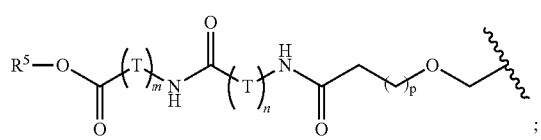

$R^3$ is a radical of formula (iii) or a radical of formula (iv)

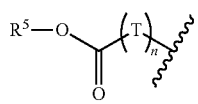

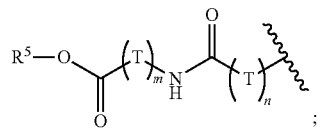

each T is independently selected from the group consisting of $(CH_2CH_2O)_xCH_2CH_2$ and $CH_2$;
each x is independently an integer from 1 to 12;
m is an integer from 1 to 11, provided that when T is $(CH_2CH_2O)_xCH_2CH_2$ then m is 1;
n is an integer from 1 to 11, provided that when T is $(CH_2CH_2O)_xCH_2CH_2$ then n is 1;
p is an integer from 1 to 5;
$R^5$ is H,

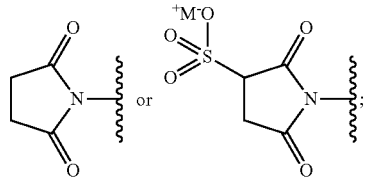

and
M is sodium or ammonium.
Preferably each T is $CH_2$.
Alternatively preferably at least one T is $CH_2$.
Alternatively preferably at least one T is $(CH_2CH_2O)_xCH_2CH_2$.
More preferably each T is $CH_2$ and m is an integer from 3 to 10, e.g. an integer from 4 to 9, e.g. an integer from 5 to 8, e.g. an integer from 6 to 7. Most preferably m is 7.

Preferably each T is $CH_2$ and n is an integer from 3 to 10, e.g. an integer from 4 to 9, e.g. an integer from 5 to 8, e.g. an integer from 6 to 7. Most preferably n is 7.
Alternatively preferably at least one T is $CH_2$ and m is an integer from 3 to 10, e.g. an integer from 4 to 9, e.g. an integer from 5 to 8, e.g. an integer from 6 to 7. Most preferably m is 7. Preferably at least one T is $CH_2$ and n is an integer from 3 to 10, e.g. an integer from 4 to 9, e.g. an integer from 5 to 8, e.g. an integer from 6 to 7. Most preferably n is 7.
Alternatively preferably at least one T is $(CH_2CH_2O)_xCH_2CH_2$ and x is an integer from 2 to 10, e.g. an integer from 2 to 9, e.g. an integer from 2 to 8, e.g. an integer from 2 to 7, e.g. an integer from 2 to 6, e.g. an integer from 2 to 5, e.g. an integer from 2 to 4. Most preferably x is 3.
Preferably Y is O. Alternatively, it is preferred that Y is C.
Preferably $R^3$ is a radical of formula (iii)

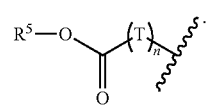

Alternatively it is preferred that $R^3$ is a radical of formula (iv)

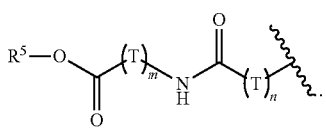

It is further preferred that, in $R^3$, one T is $(CH_2CH_2O)_xCH_2CH_2$ and one T is $CH_2$.
It is further preferred that, in $R^3$, $(T)_m$ is $(CH_2CH_2O)_xCH_2CH_2$ and $(T)_n$ is $(CH_2)_n$. Alternatively it is preferred that, in $R^3$, $(T)_n$ is $(CH_2CH_2O)_xCH_2CH_2$ and $(T)_m$ is $(CH_2)_m$.
Alternatively preferably $R^3$ is a radical of formula (iv) wherein each T is $(CH_2CH_2O)_xCH_2CH_2$, wherein each x in each radical of formula (iv) is independently selected.
Preferably $R^1$ and $R^2$ are both a radical of formula (i)

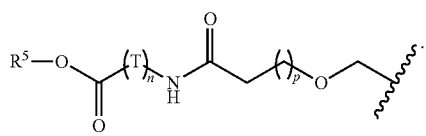

Alternatively it is preferred that $R^1$ and $R^2$ are both a radical of formula (ii)

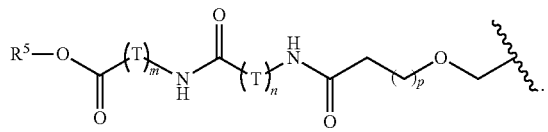

It is further preferred that, in $R^1$, one T is $(CH_2CH_2O)_xCH_2CH_2$ and one T is $CH_2$ and, in $R^2$, one T is $(CH_2CH_2O)_xCH_2CH_2$ and one T is $CH_2$.

It is further preferred that, in both $R^1$ and $R^2$, $(T)_m$ is $(CH_2CH_2O)_xCH_2CH_2$ and $(T)_n$ is $(CH_2)_n$. Alternatively it is preferred that, in both $R^1$ and $R^2$, $(T)_n$ is $(CH_2CH_2O)_xCH_2CH_2$ and $(T)_m$ is $(CH_2)_m$. Alternatively it is preferred that, in both $R^1$ and $R^2$, each T is $(CH_2CH_2O)_xCH_2CH_2$, wherein each x in each radical of formula (ii) is independently selected.

Alternatively it is preferred that $R^1$ is H or $C_{1-6}$alkyl, e.g. $CH_3$ or $CH_2CH_3$. Alternatively it is preferred that $R^1$ is $NH_2$. Alternatively it is preferred that $R^1$ is NHZ, more preferably where Z is $C(O)(CH_2)_wN(H)G$, e.g. where G is Troc (2,2,2-trichloroethyloxycarbonyl), Fmoc (fluorenylmethyloxycarbonyl) or Cbz (benzyloxycarbonyl). Preferably w is 7.

Preferably $R^5$ is selected from the group consisting of

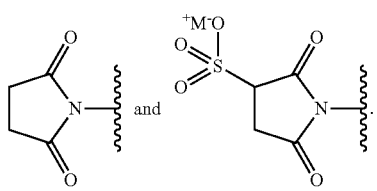

Preferably $R^5$ is

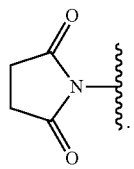 [SMILES: *N1C(=O)CCC1=O]

Alternatively preferably $R^5$ is H. Alternatively preferably $R^5$ is

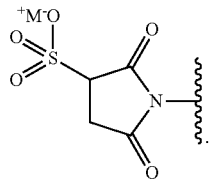

Preferably Y is O; B is O; $R^1$ and $R^2$ are absent; and either A, E, D and X are all $CH_2$ or A, D and X are all $CH_2$ and E is $(CH_2CH_2O)_tCH_2$; and t is an integer from 1 to 10, preferably an integer from 1 to 2.

Alternatively it is preferred that Y is C; $R^1$ and $R^2$ are both H; A, E, B and D are $CH_2$ and X is O.

Alternatively it is preferred that Y is C; A is $(CH_2)_u$; $R^1$ and $R^2$ are both H; B, X, D and E are all absent; and u is an integer from 1 to 10.

Alternatively it is preferred that:
Y is C; X is O; A, E and D are all $CH_2$; B is $(CH_2)_p$;
$R^1$ is H, NHZ or $C_{1-6}$alkyl;

$R^2$ is a radical of formula (i) or a radical of formula (ii)

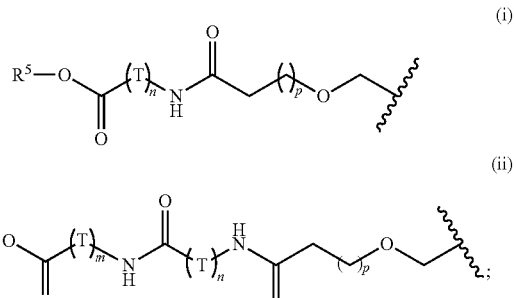

and
Z is H, acyl, $C(O)(CH_2)_wN(H)G$, *$CH_3$*CO— where *C denotes $^{13}C$ or $^{14}C$, 5-TAMRA (4-carboxytetramethylrhodamine), Fluorescein (resorcinolphthalein), Alexa Fluor 350 (7-amino-4-methyl-6-sulfocoumarin-3-acetic acid), BODIPY (4,4-difluoro-4-bora-3a,4a-diaza-s-indacene) or Alkyne MegaStokes dye 608 (1-{3-{[4-(2-cyclooctyn-1-ylmethyl)benzoyl]amino}propyl}-4-{2-[4-(dimethylamino)phenyl]ethenyl}pyridinium hexafluorophosphate);
w is an integer from 1 to 11;
G is H, acyl, (t-butoxycarbonyl), Troc (2,2,2-trichloroethyloxycarbonyl), Fmoc (9-fluorenylmethoxycarbonyl), Cbz (carboxybenzyl),* *$CH_3$*CO— where *C denotes $^{13}C$ or $^{14}C$, 5-TAMRA (4-carboxytetramethylrhodamine), Fluorescein (resorcinolphthalein), Alexa Fluor 350 (7-amino-4-methyl-6-sulfocoumarin-3-acetic acid), BODIPY (4,4-difluoro-4-bora-3a,4a-diaza-s-indacene) or Alkyne MegaStokes dye 608 (1-{3-{[4-(2-cyclooctyn-1-ylmethyl)benzoyl]amino}propyl}-4-{2-[4-(dimethylamino)phenyl]ethenyl}pyridinium hexafluorophosphate).

Preferably $R^2$ is a radical of formula (ii)

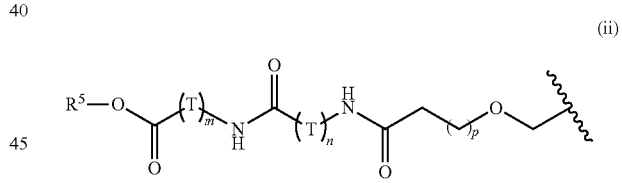

and $R^1$ is H, NHZ or $C_{1-6}$alkyl. It is further preferred that, in $R^2$, one T is $(CH_2CH_2O)_xCH_2CH_2$ and one T is $CH_2$.

It is further preferred that, in $R^2$, $(T)_m$ is $(CH_2CH_2O)_xCH_2CH_2$ and $(T)_n$ is $(CH_2)_n$. Alternatively it is preferred that, in $R^2$, $(T)_n$ is $(CH_2CH_2O)_xCH_2CH_2$ and $(T)_m$ is $(CH_2)_m$. Alternatively it is preferred that, in $R^2$, each T is $(CH_2CH_2O)_xCH_2CH_2$, wherein each x in each radical of formula (ii) is independently selected.

Alternatively it is preferred that Y is C; X is O; A, E and D are all $CH_2$; B is $(CH_2)_p$; $R^1$ and $R^2$, both the same, are a radical of formula (i) or a radical of formula (ii)

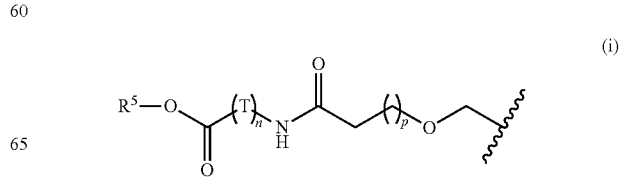

-continued

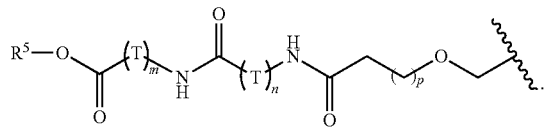
(ii)

Preferably, Y is C; X is O; A, E and D are all CH$_2$; B is (CH$_2$)$_p$; R$^1$ and R$^2$, both the same, are a radical of formula (i)

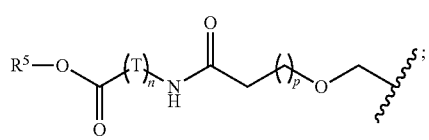
(i)

R$^3$ is a radical of formula (iii)

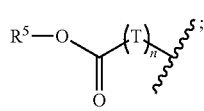
(iii)

and p is 1.

Alternatively preferably Y is C; X is O; A, E and D are all CH$_2$; B is (CH$_2$)$_p$; R$^1$ and R$^2$, both the same, are a radical of formula (ii)

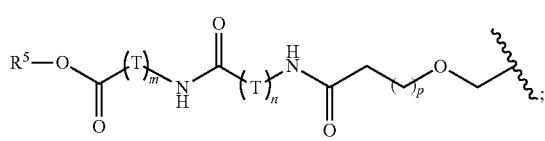
(ii)

R$^3$ is a radical of formula (iv)

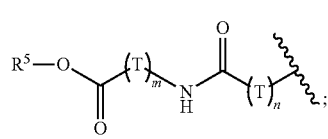
(iv)

and p is 1.

Preferably Y is C; R$^1$ and R$^2$ are both H; A, E, B and D are CH$_2$; X is O; and R$^3$ is a radical of formula (iii)

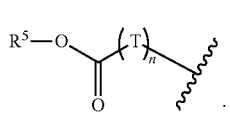
(iii)

Alternatively preferably Y is C; R$^1$ and R$^2$ are both H; A, E, B and D are CH$_2$; X is O; and R$^3$ is a radical of formula (iv)

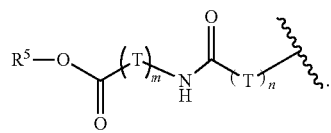
(iv)

Preferably Y is C; X is O; A, E and D are all CH$_2$; B is (CH$_2$)$_p$; R$^1$ is H; R$^2$ is a radical of formula (i)

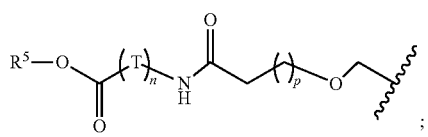
(i)

R$^3$ is a radical of formula (iii)

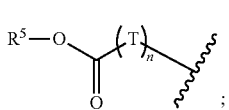
(iii)

and p is 1.

Alternatively preferably Y is C; X is O; A, E and D are all CH$_2$; B is (CH$_2$)$_p$; R$^1$ is H; R$^2$ is a radical of formula (ii)

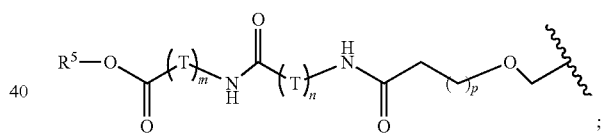
(ii)

R$^3$ is a radical of formula (iv)

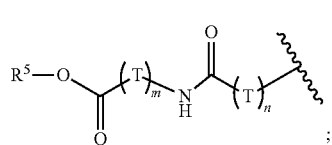
(iv)

and p is 1.

Alternatively preferably Y is C; X is O; A, E and D are all CH$_2$; B is (CH$_2$)$_p$; R$^1$ is H; R$^2$ is a radical of formula (ii)

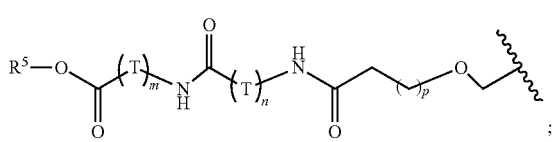
(ii)

$R^3$ is a radical of formula (iii)

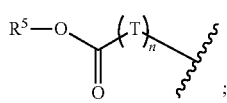
(iii)

and p is 1.

Alternatively preferably Y is C; X is O; A, E and D are all $CH_2$; B is $(CH_2)_p$; $R^1$ is H; $R^2$ is a radical of formula (i)

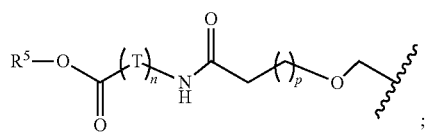
(i)

and $R^3$ is a radical of formula (iv)

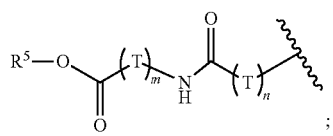
(iv)

and p is 1.

Preferably Y is C; A is $(CH_2)_u$; $R^1$ and $R^2$ are both H; B, X, D and E are all absent; u is an integer from 1 to 10; and $R^3$ is a radical of formula (iii)

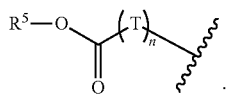
(iii)

Alternatively preferably Y is C; A is $(CH_2)_u$; $R^1$ and $R^2$ are both H; B, X, D and E are all absent; u is an integer from 1 to 10; and $R^3$ is a radical of formula (iv)

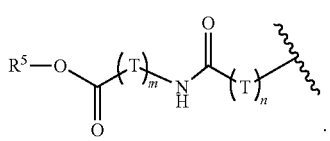
(iv)

Preferably Y is O; B is O; $R^1$ and $R^2$ are absent; and either A, E, D and X are all $CH_2$ or A, D and X are all $CH_2$ and E is $(CH_2CH_2O)_tCH_2$; t is an integer from 1 to 10, preferably an integer from 1 to 2; and $R^3$ is a radical of formula (iii)

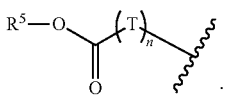
(iii)

Alternatively preferably Y is O; B is O; $R^1$ and $R^2$ are absent; and either A, E, D and X are all $CH_2$ or A, D and X are all $CH_2$ and E is $(CH_2CH_2O)_tCH_2$; t is an integer from 1 to 2; and $R^3$ is a radical of formula (iv)

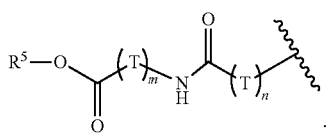
(iv)

Preferably p is 1.
Preferably t is an integer from 1 to 2.
Preferably M is sodium.
Preferably the compound of formula (I) is selected from the group consisting of:

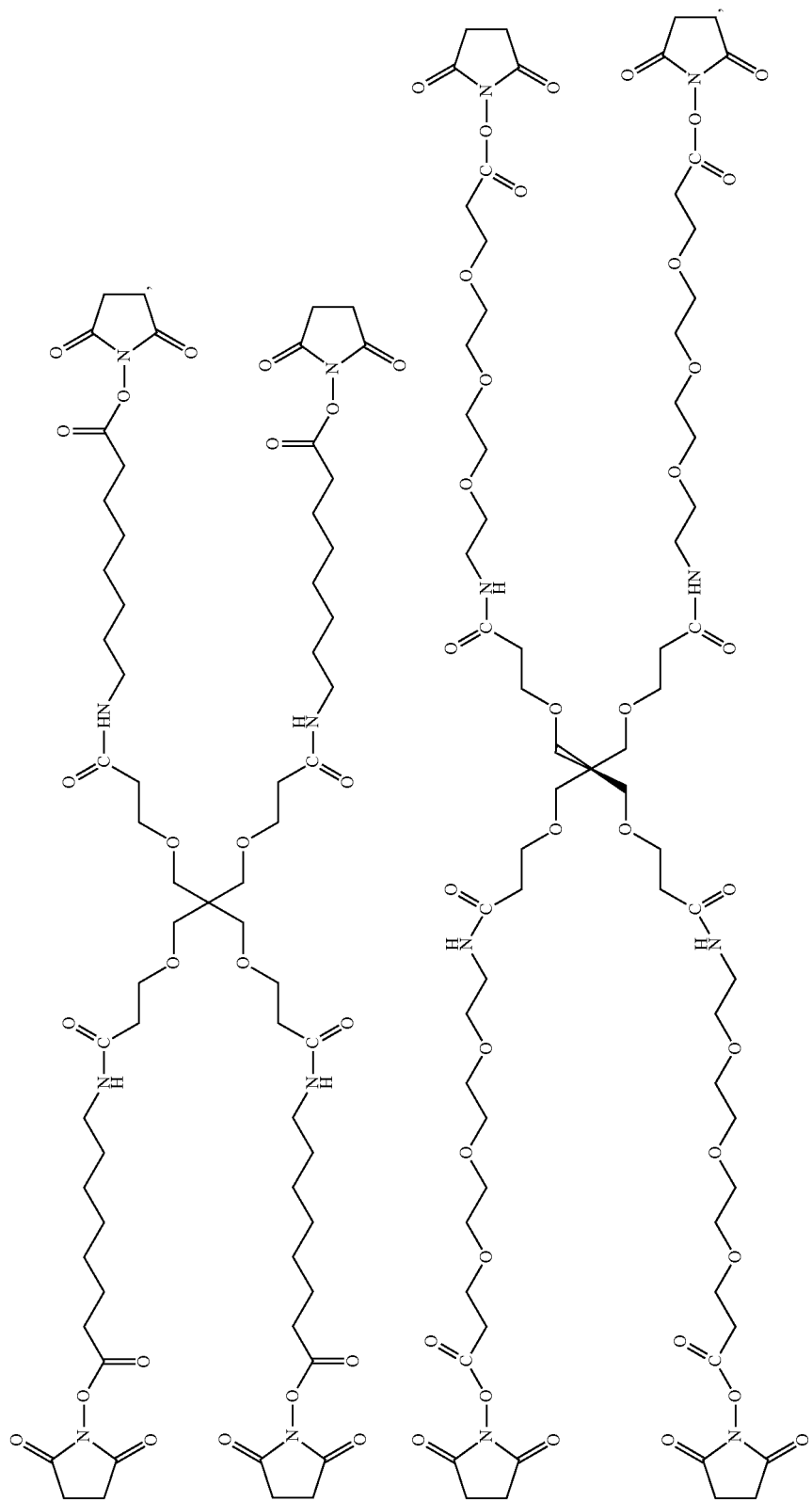

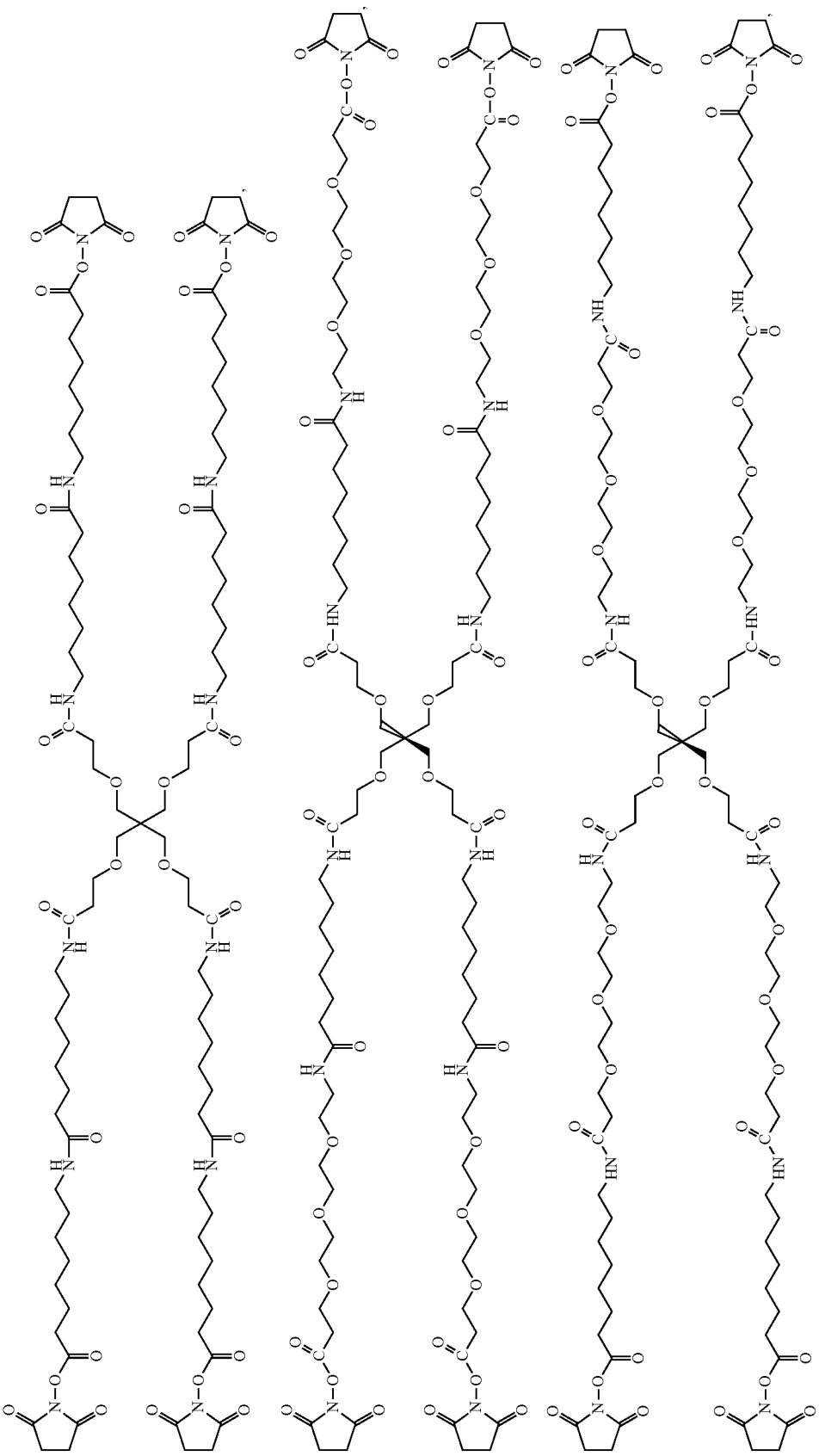

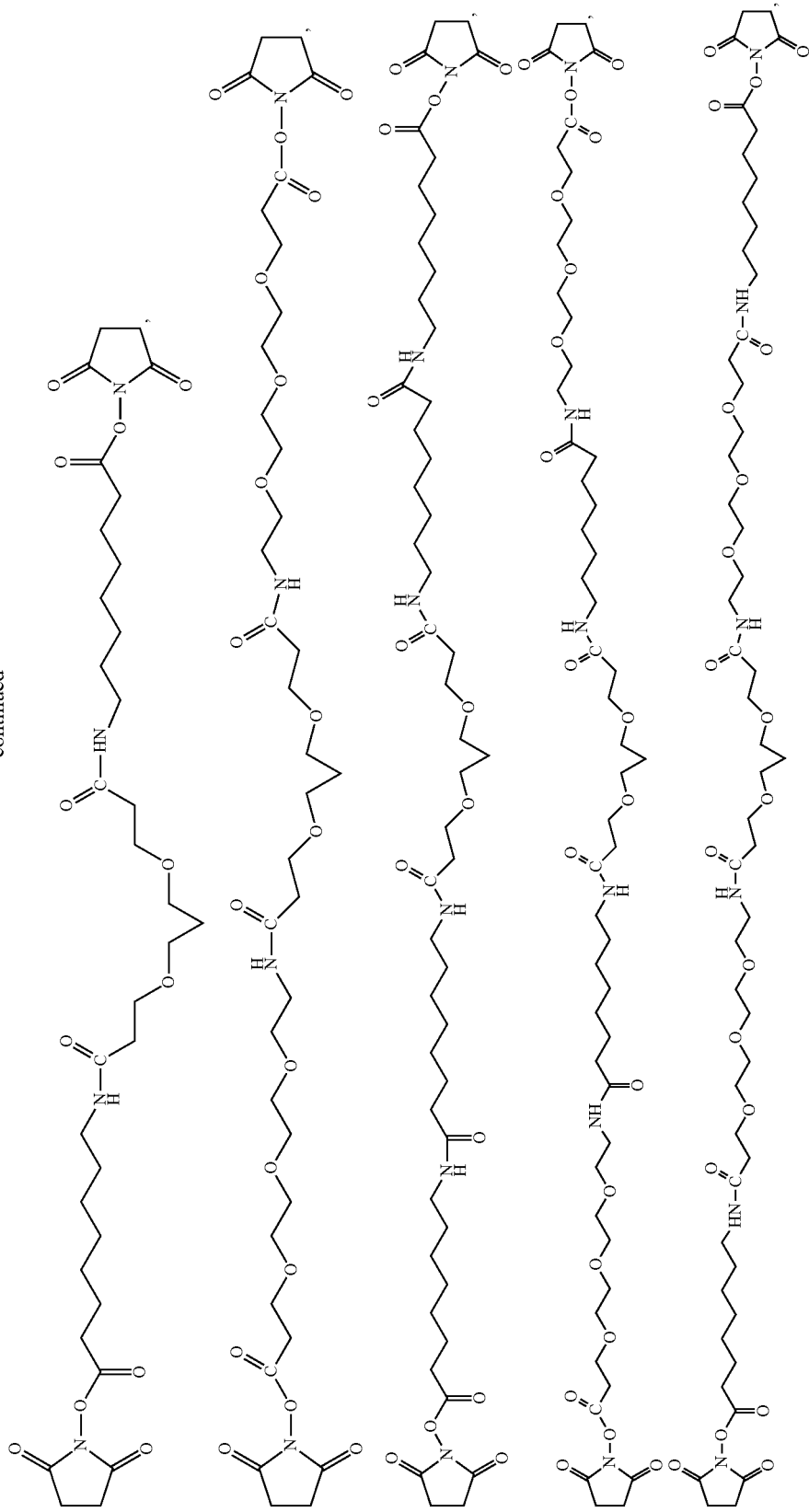

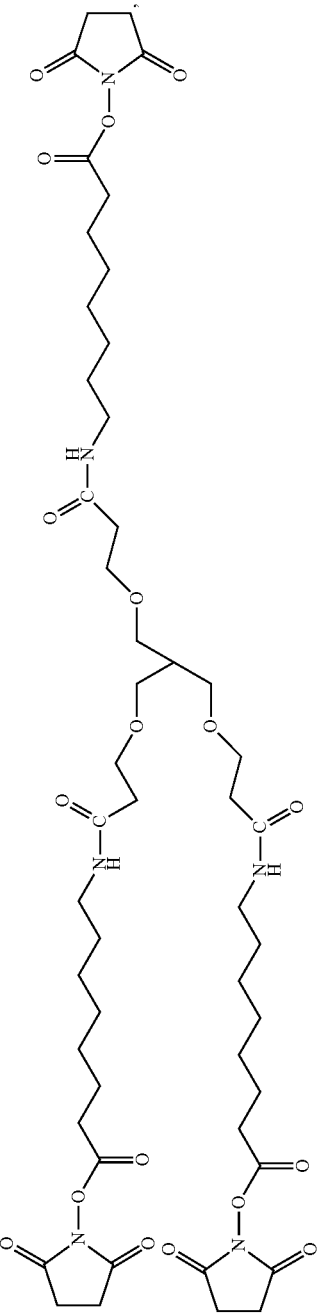
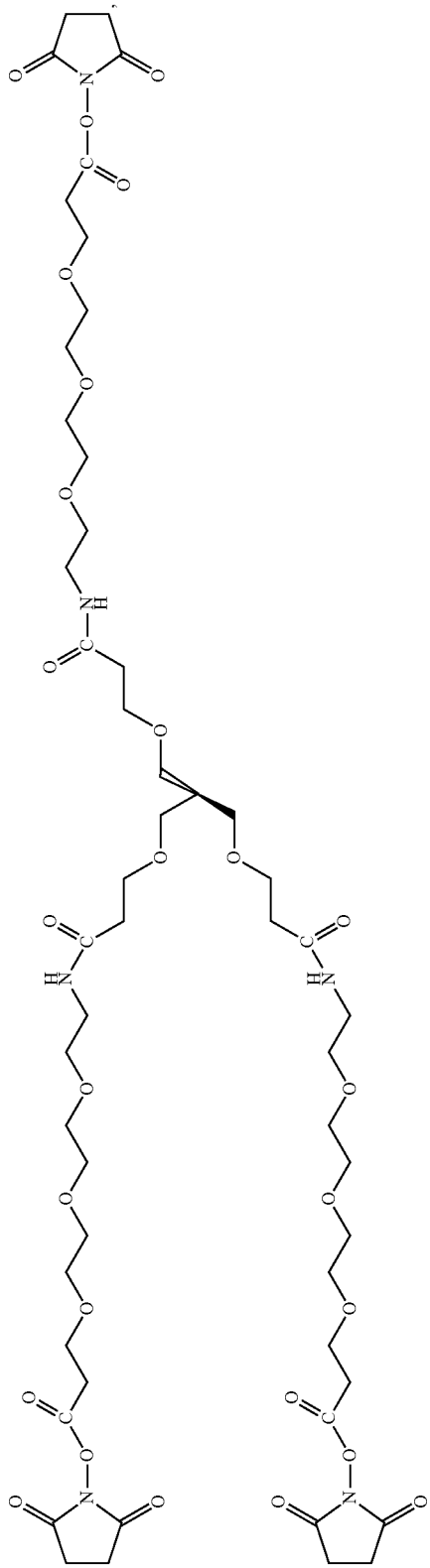

-continued
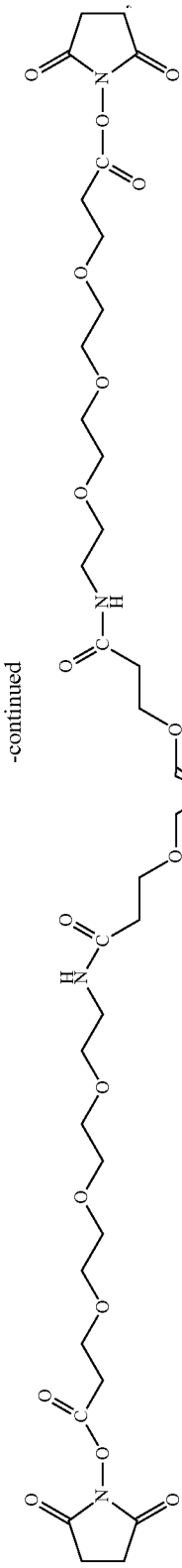 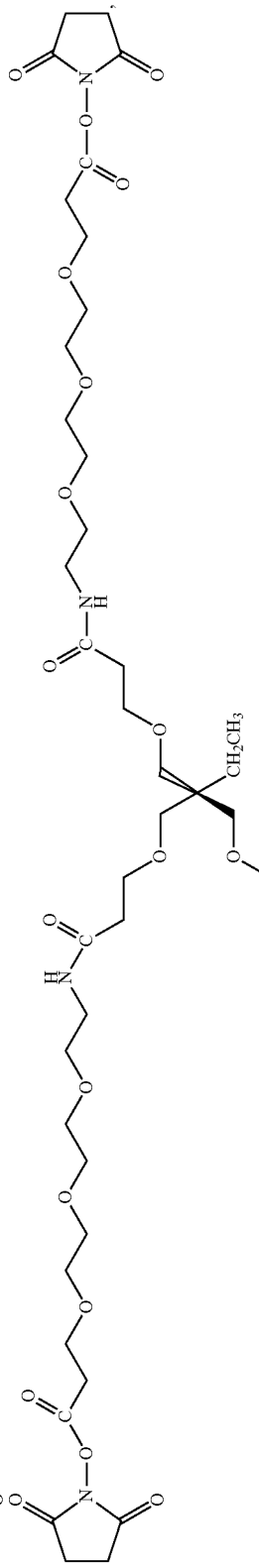

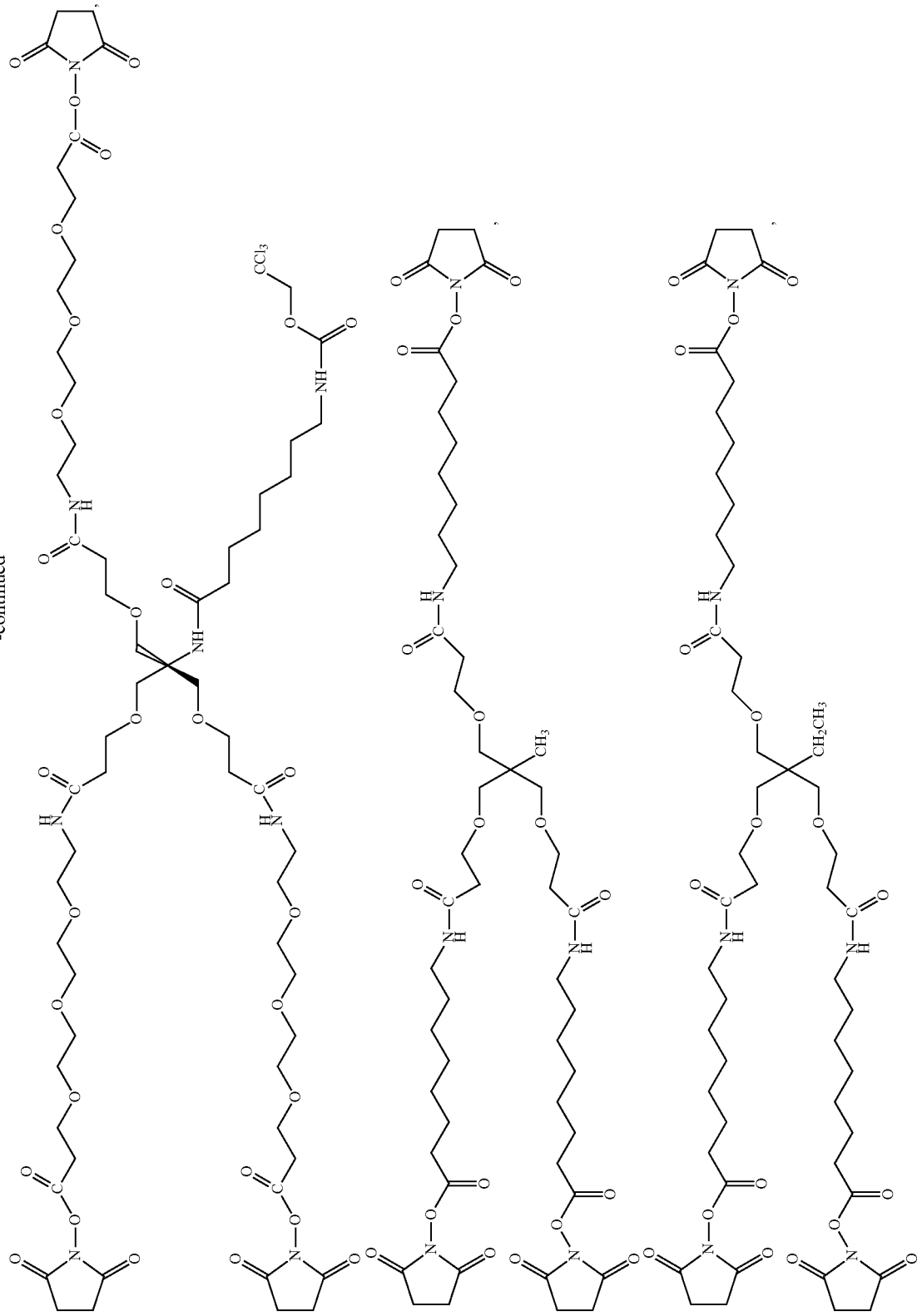

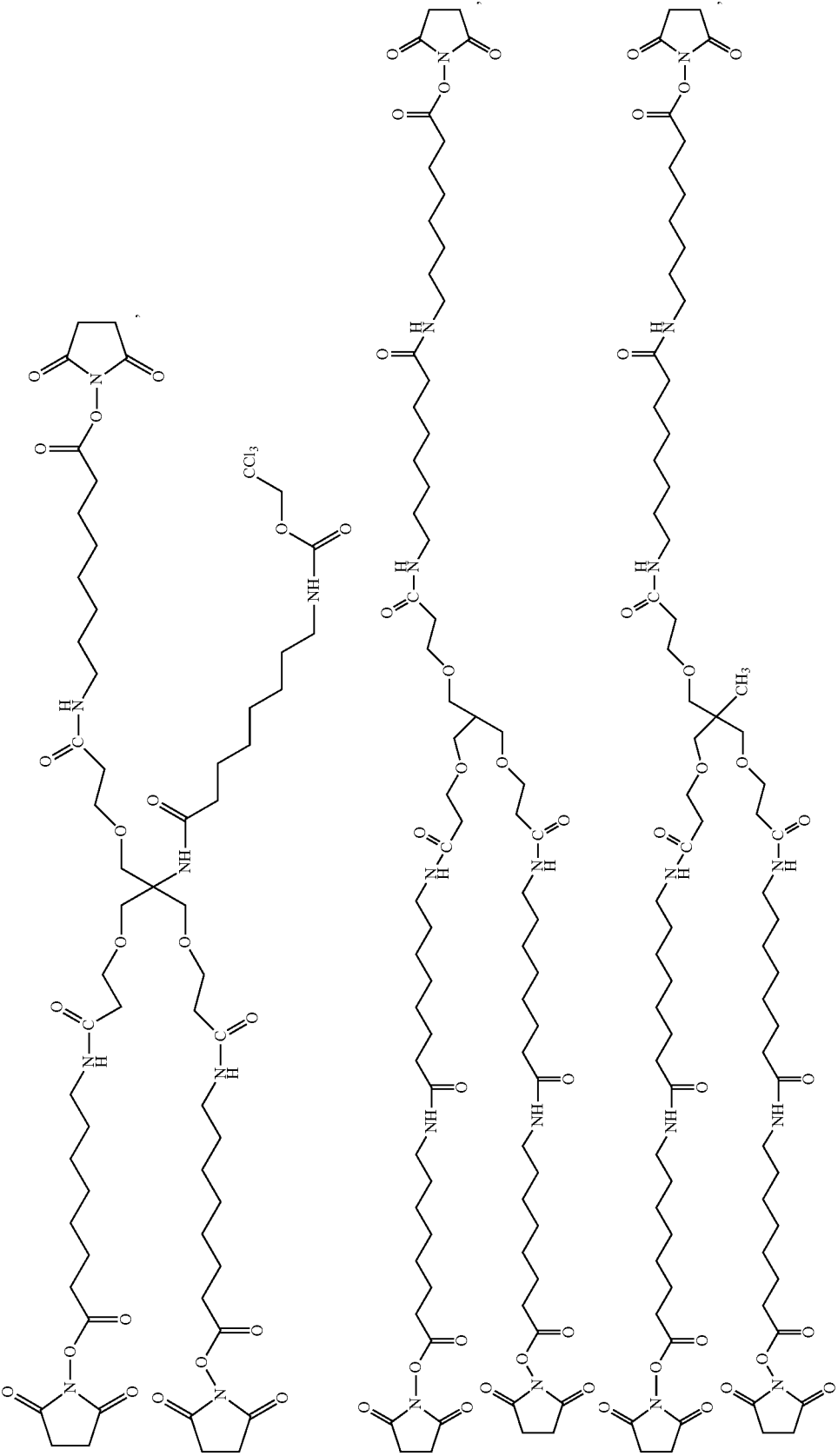

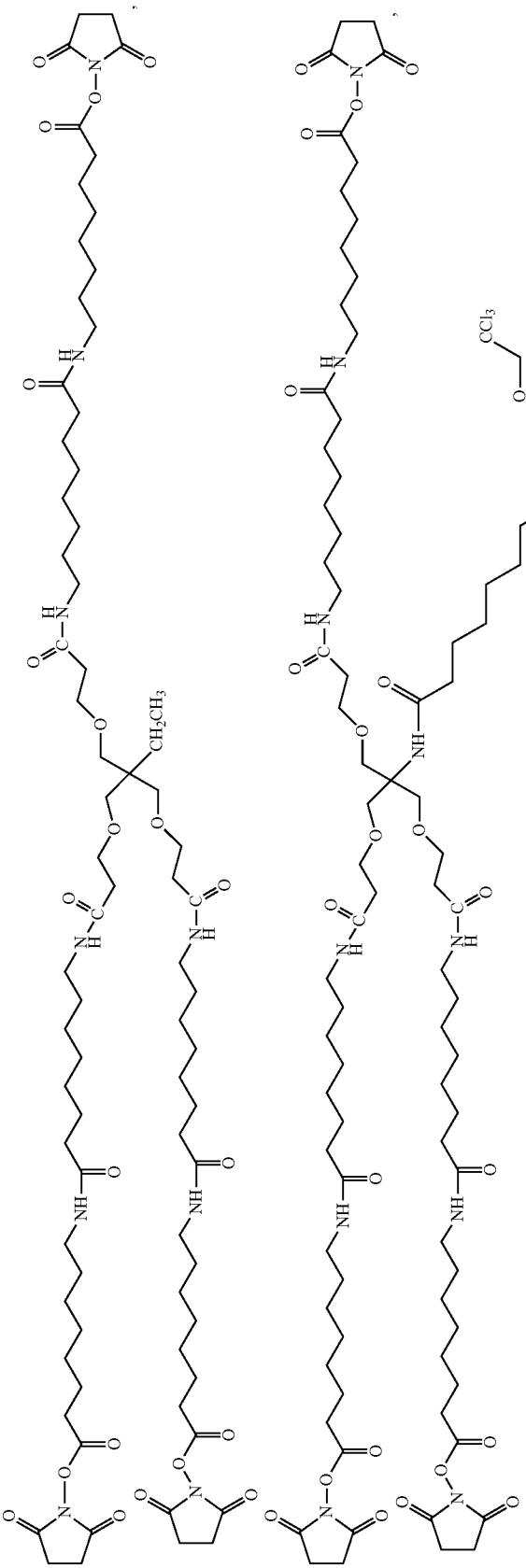
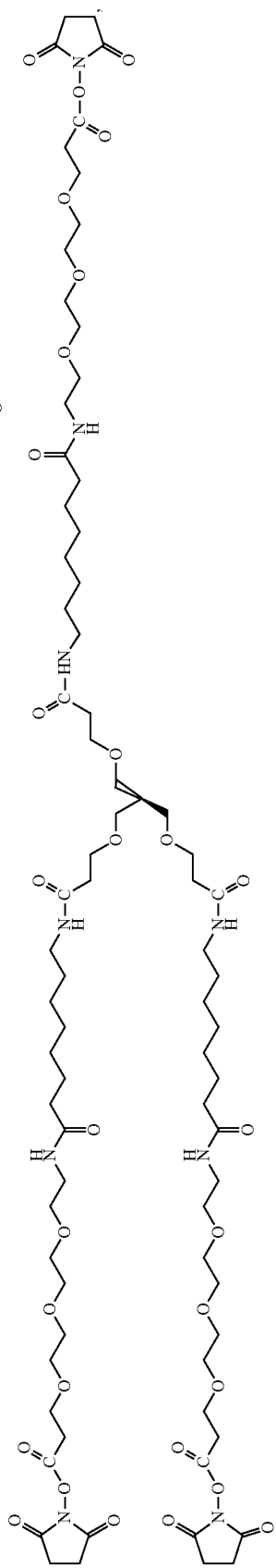

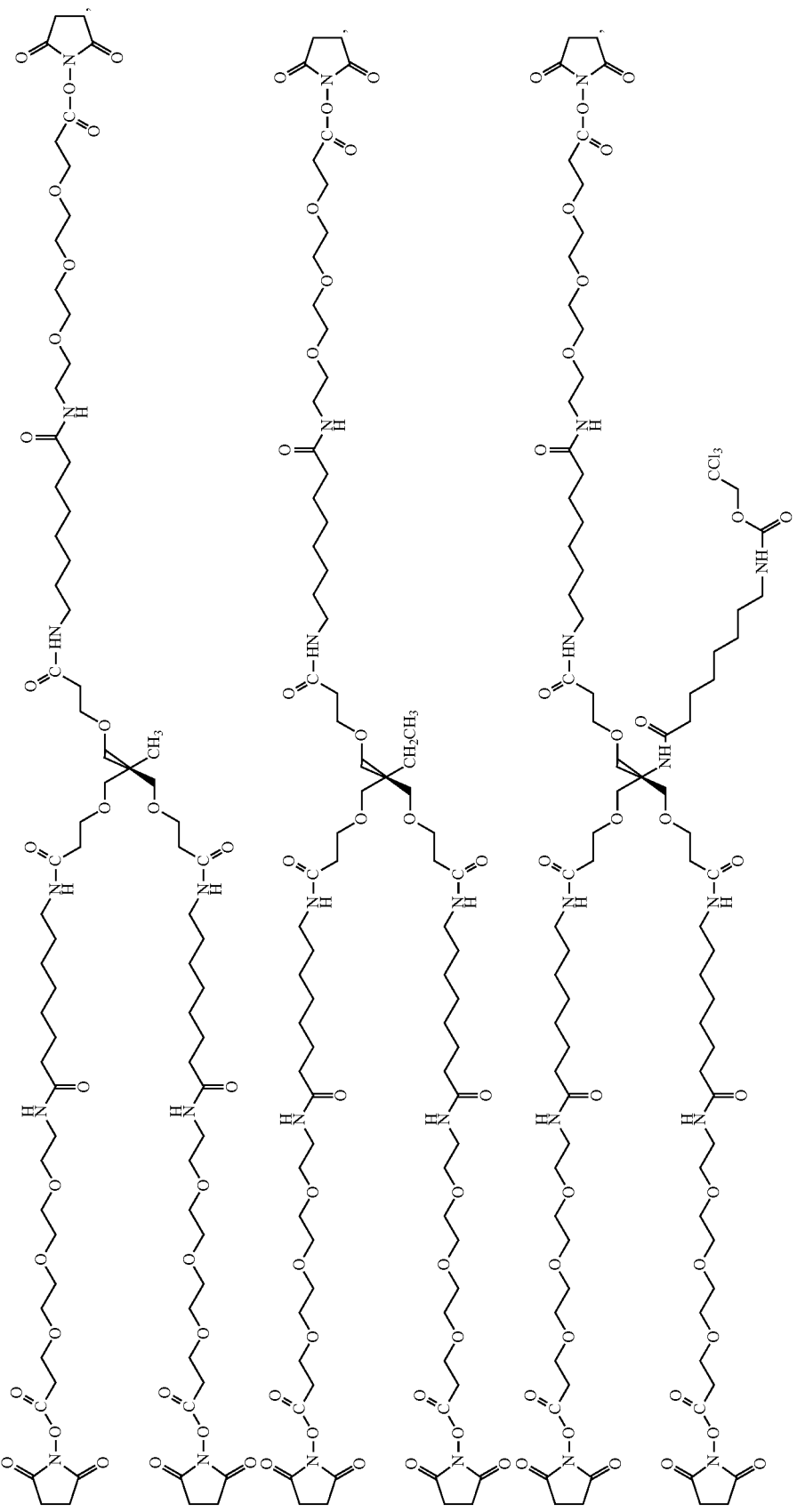

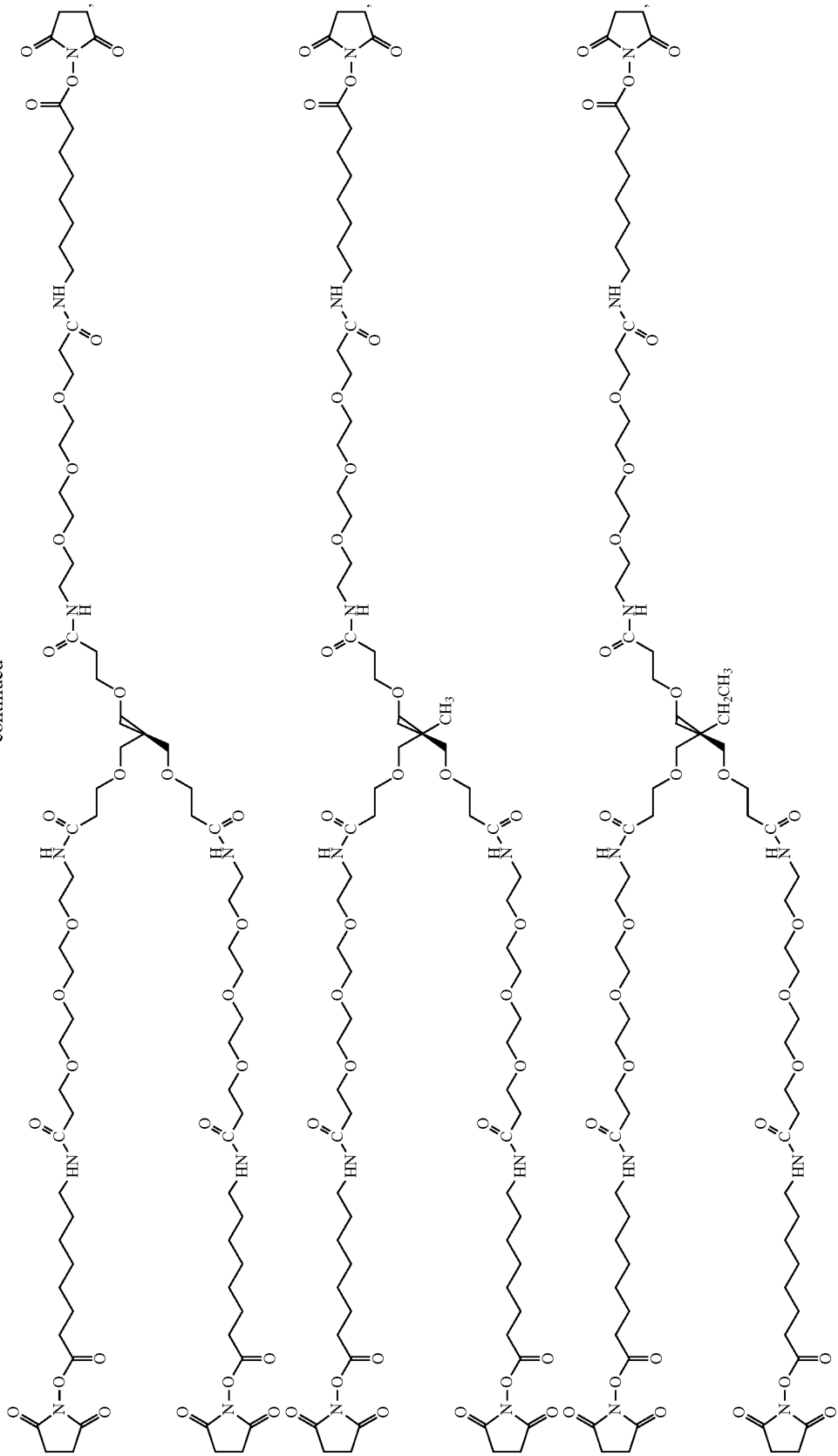

-continued
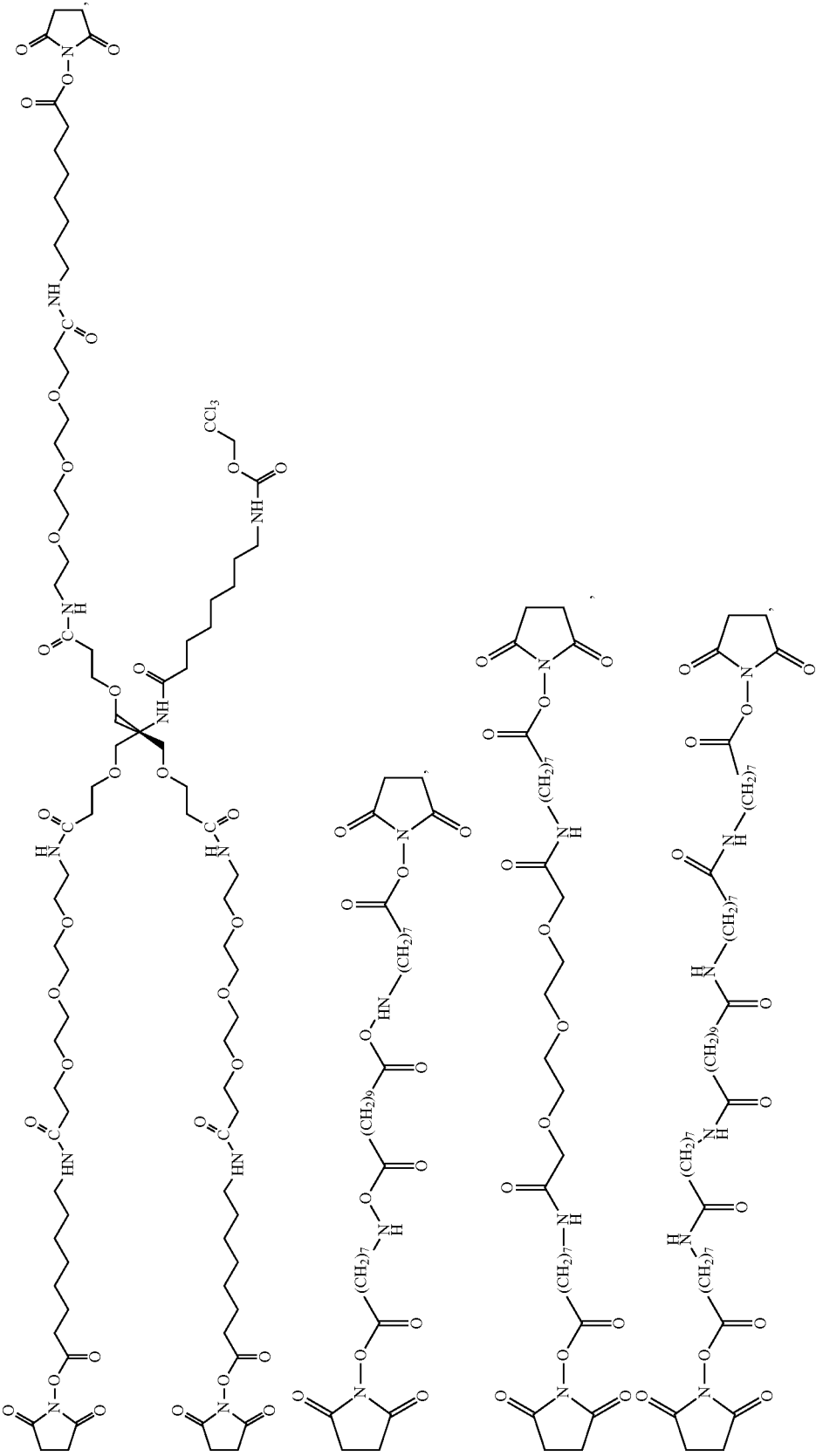

-continued
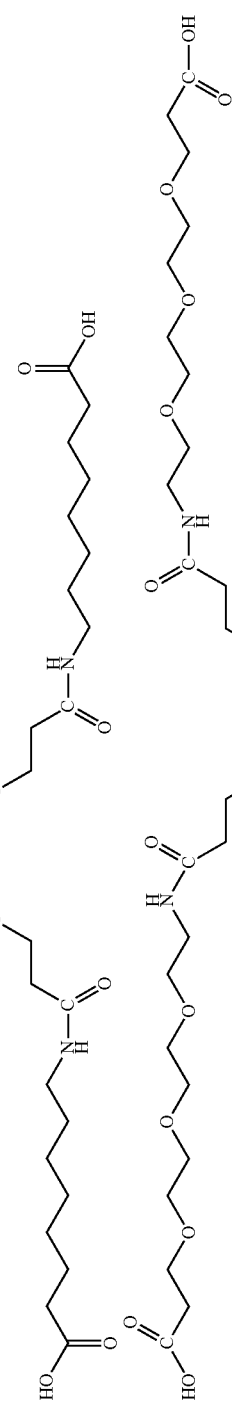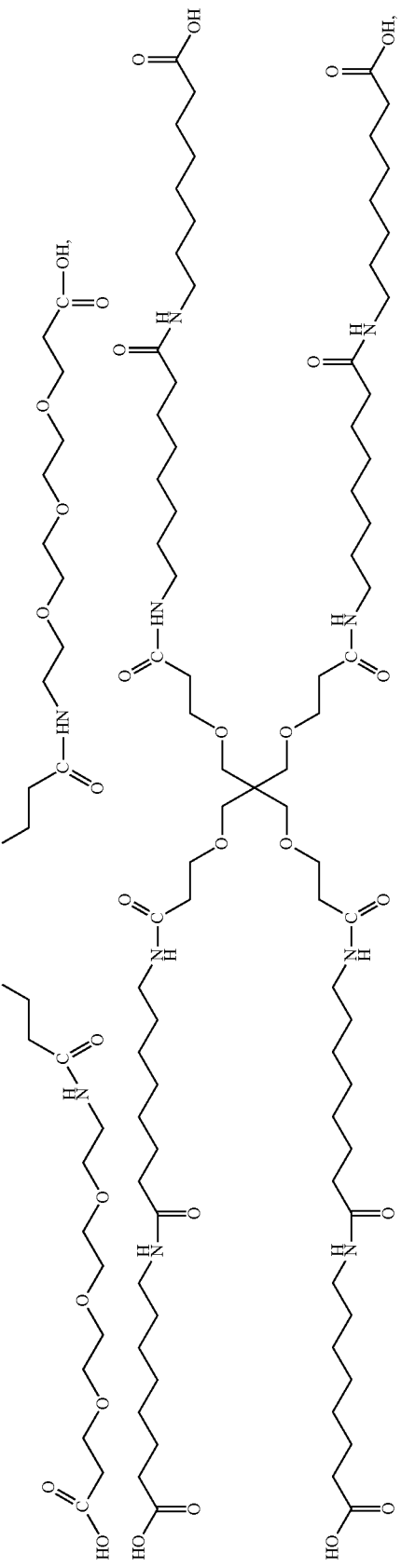

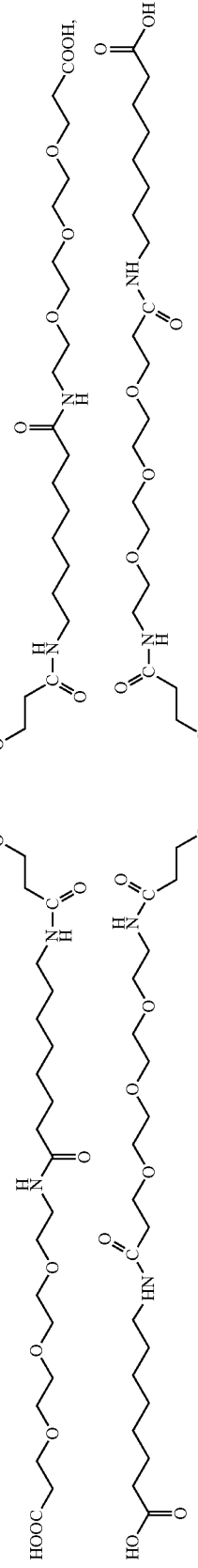
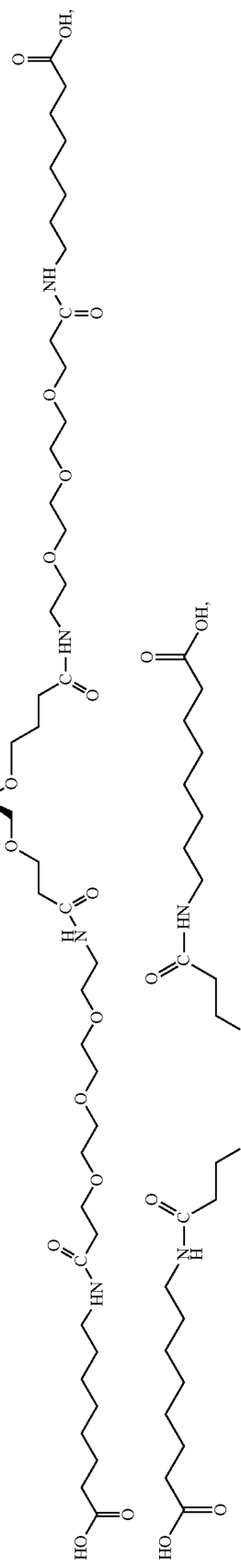
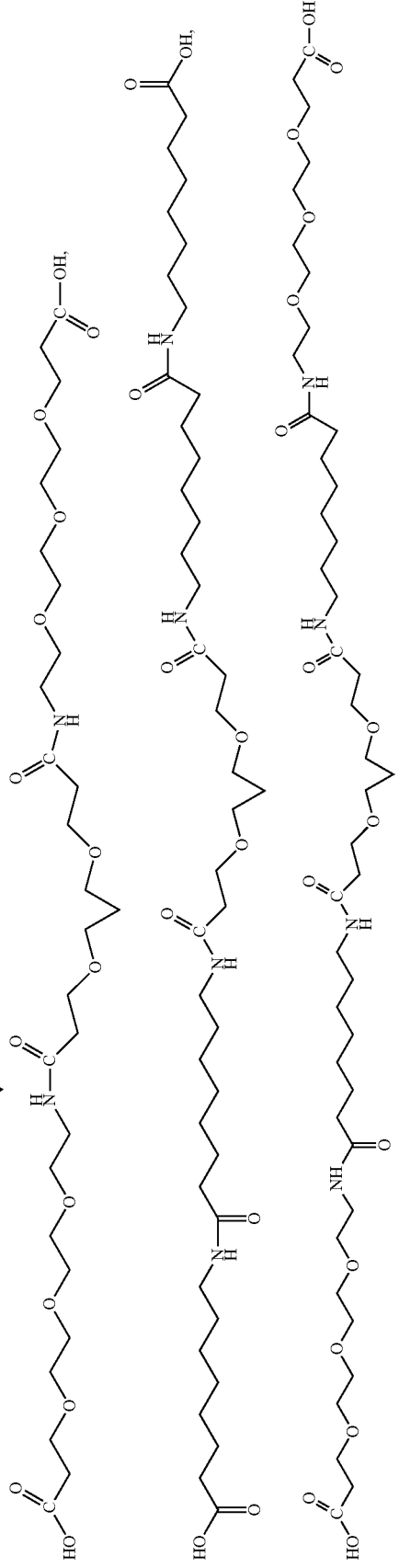

-continued
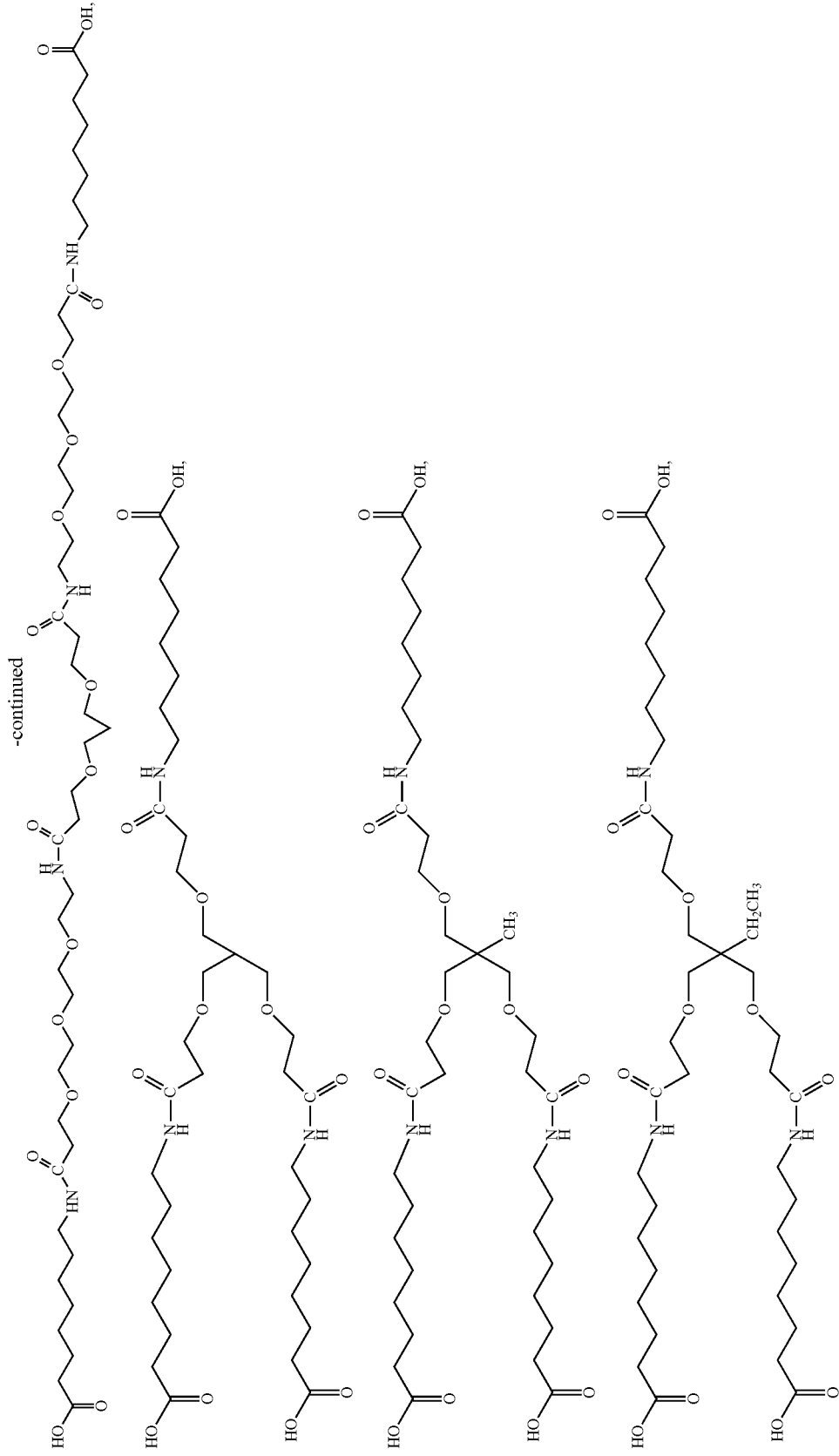

-continued
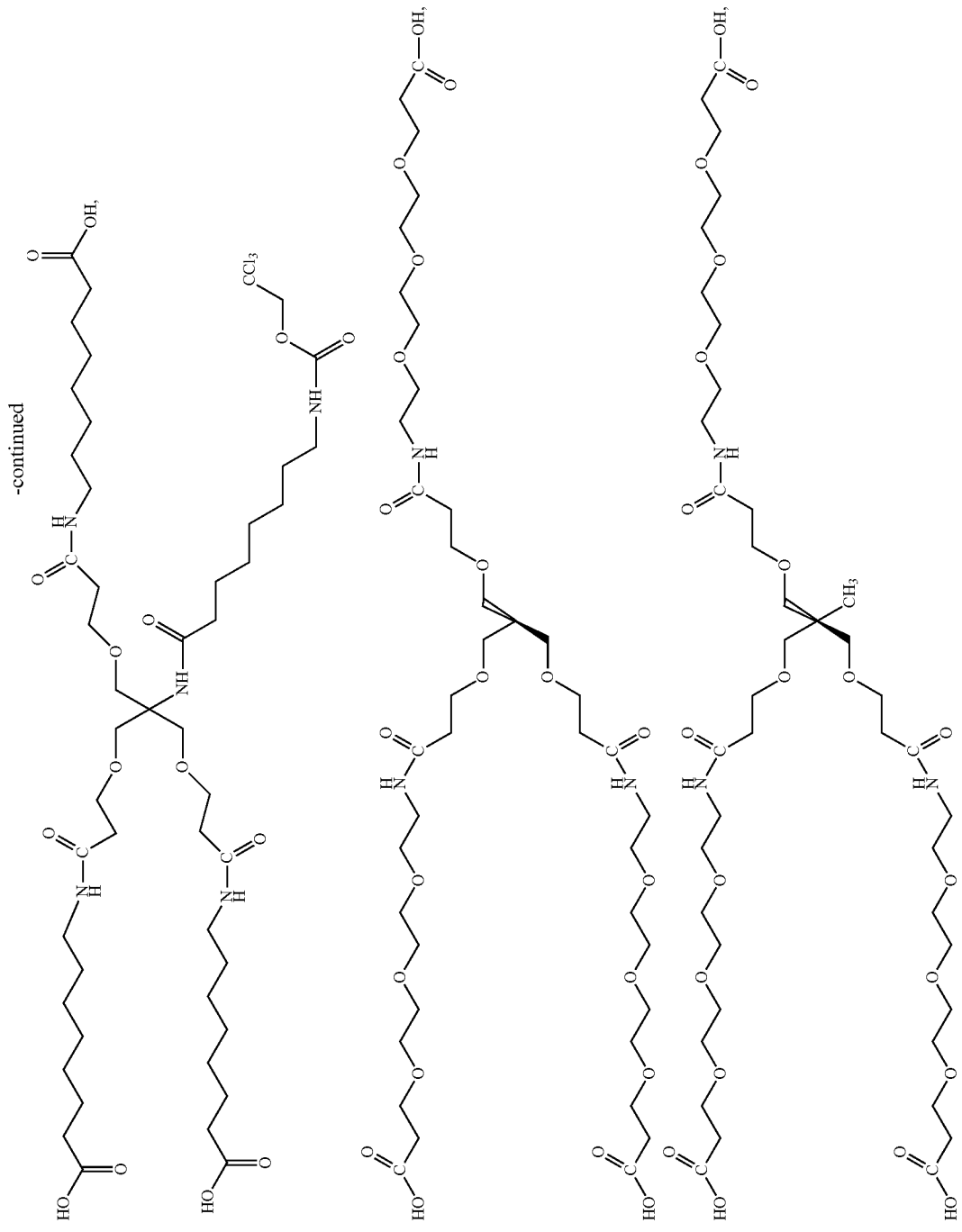

-continued
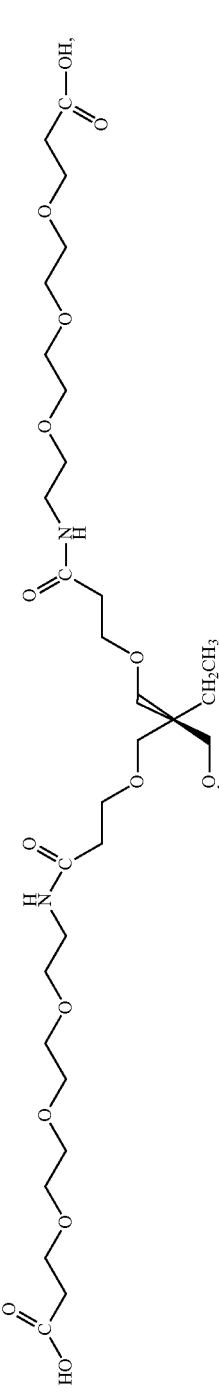 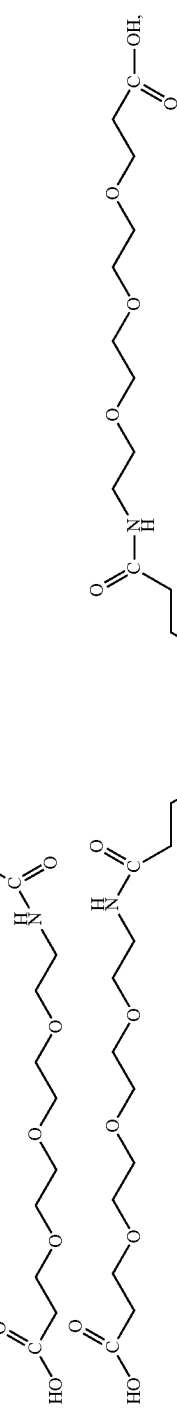 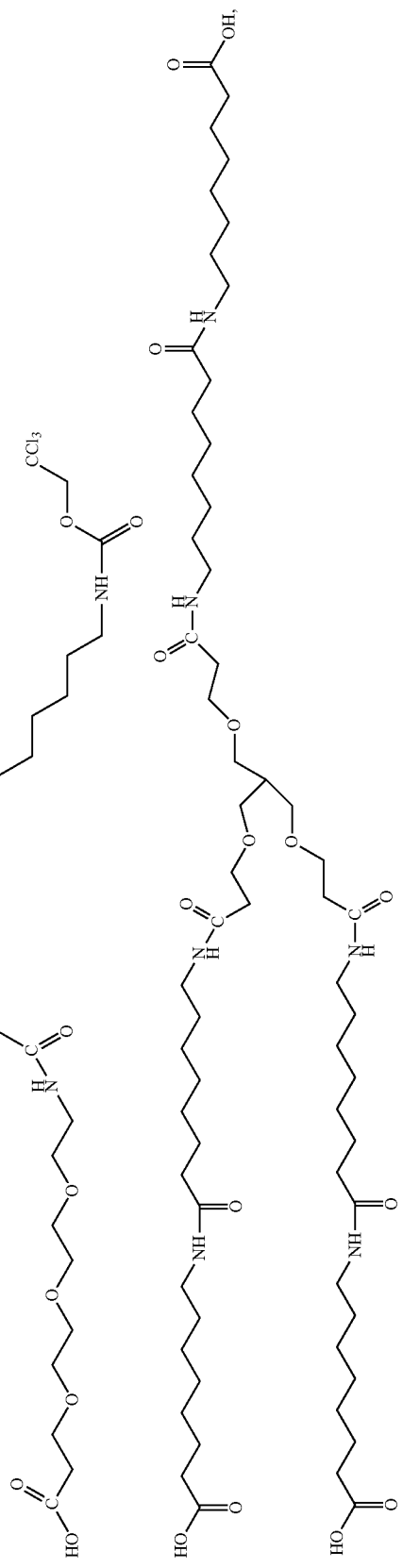

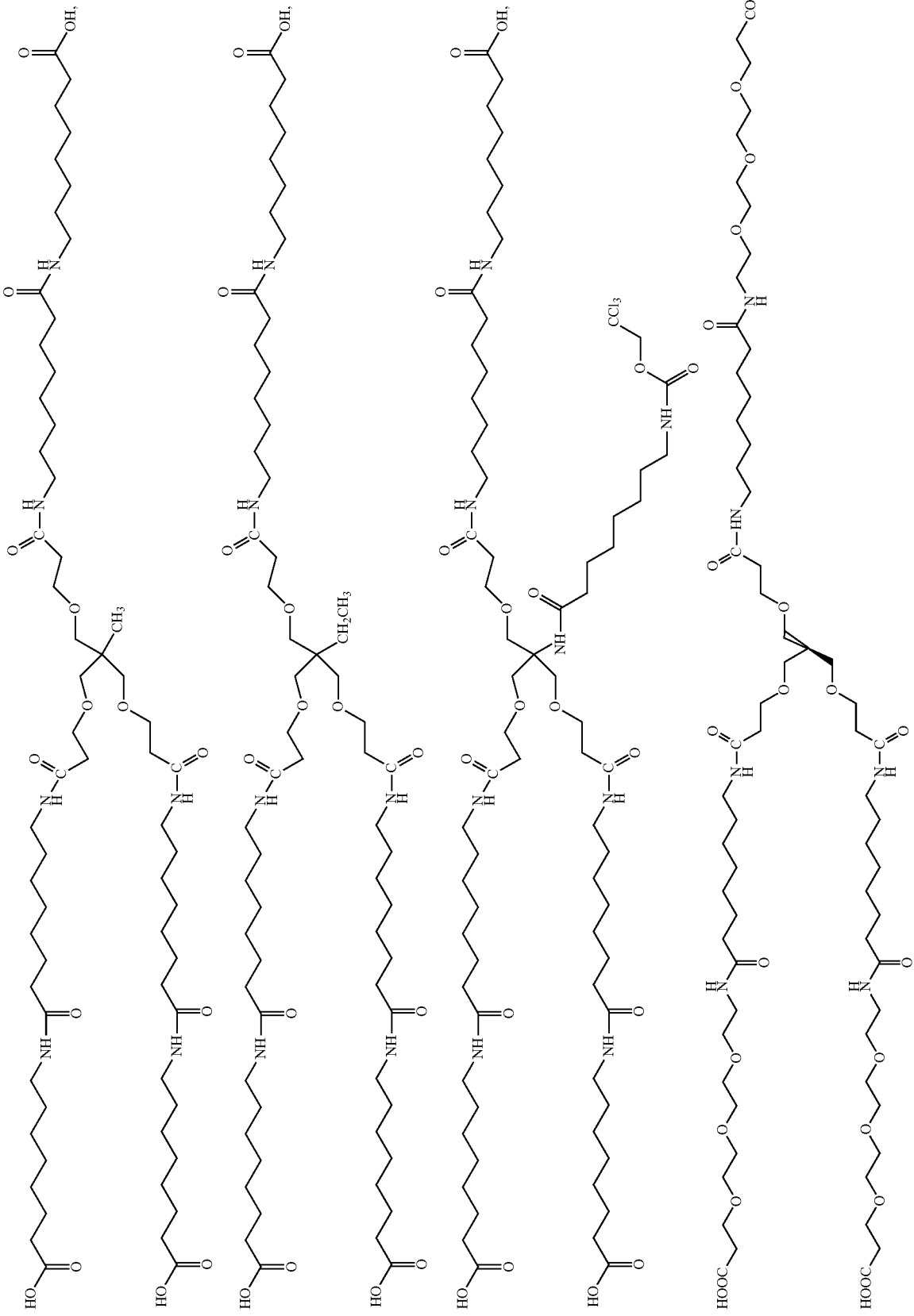

-continued
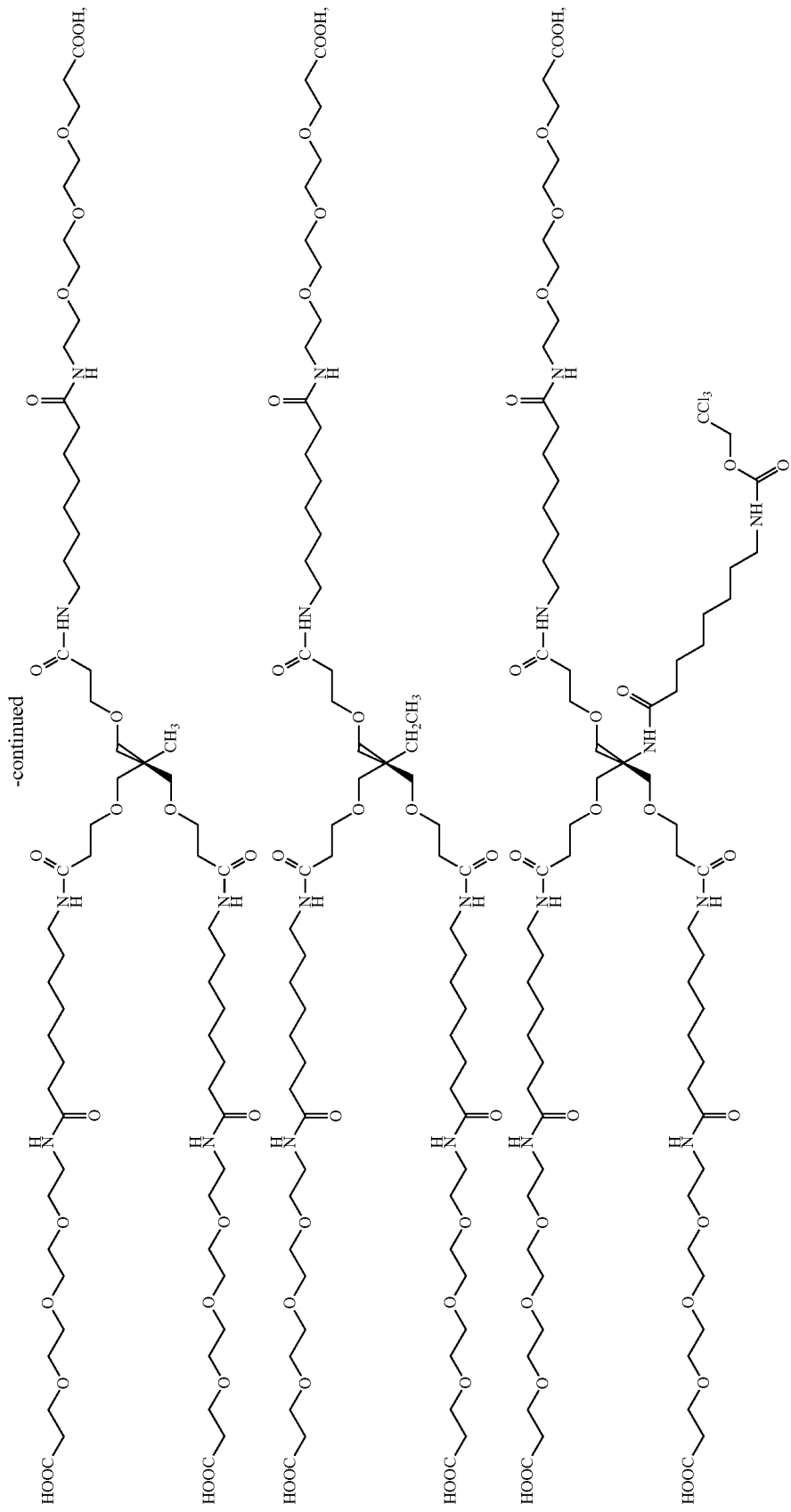

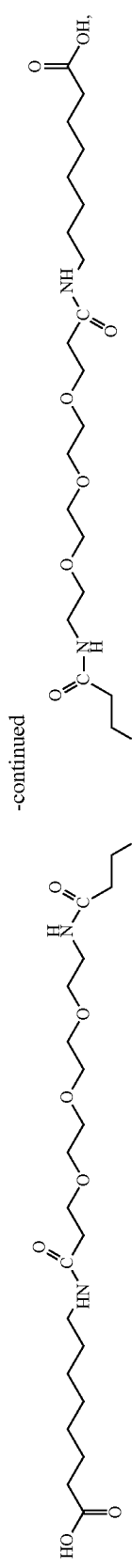
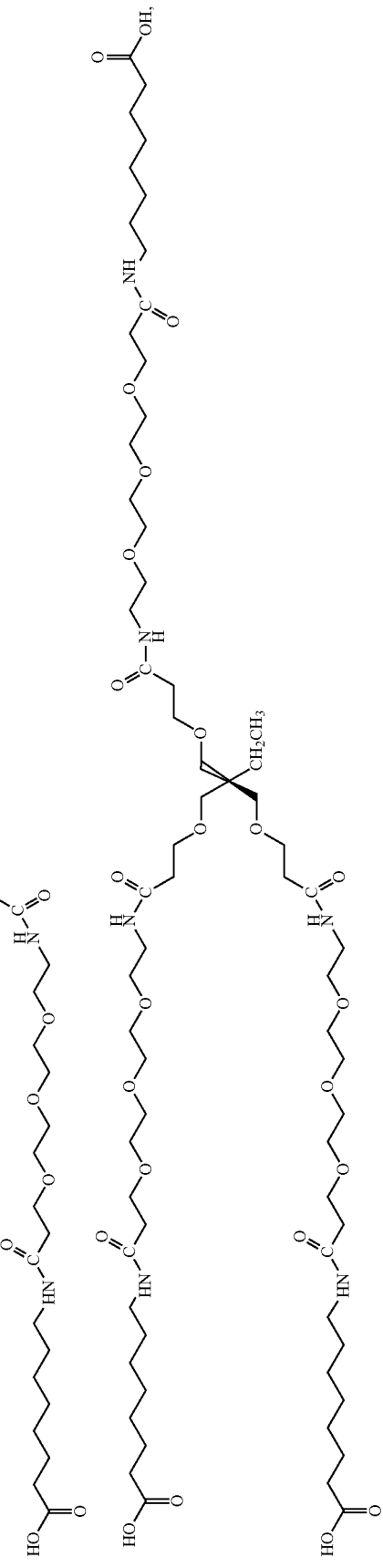

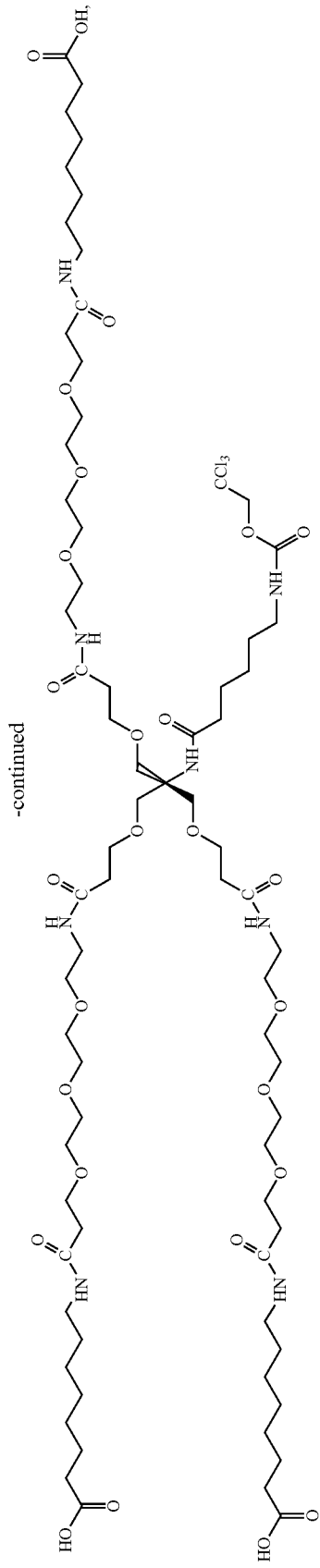
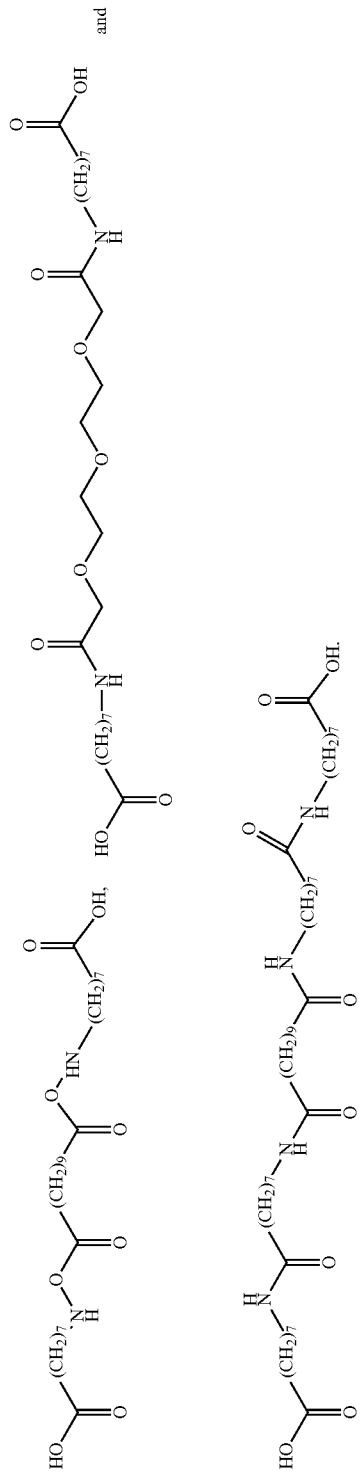

In another aspect, the invention provides a compound selected from the group consisting of:

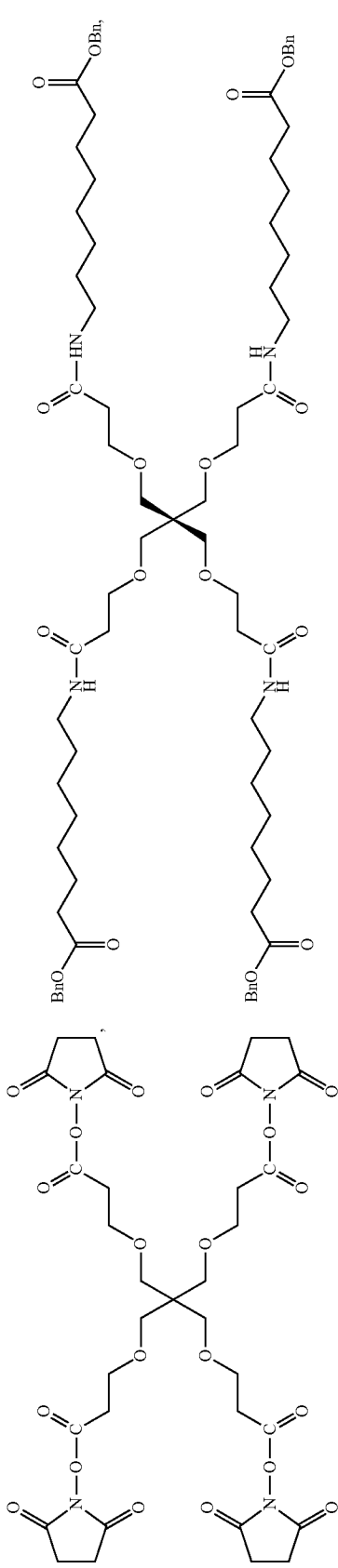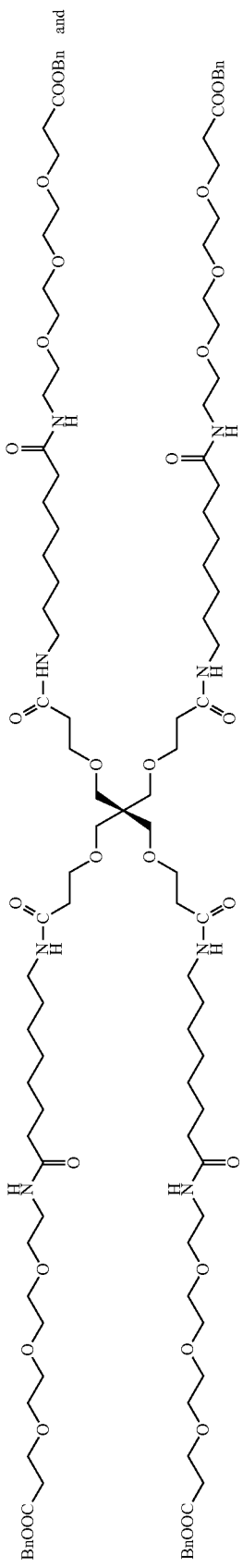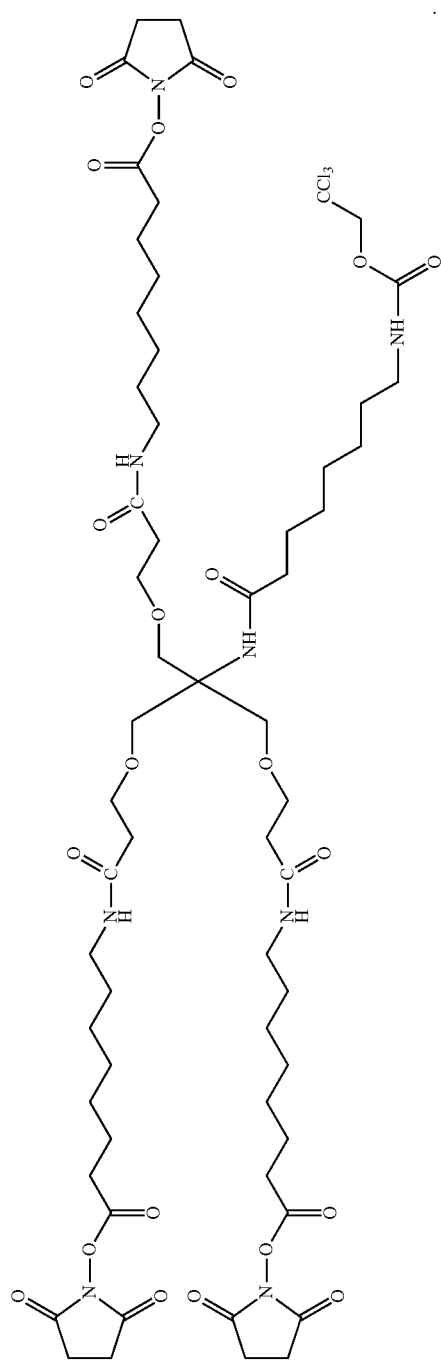

In another aspect, the invention provides the use of a compound of formula (I) as defined above for preparing a dendritic compound.

In still another aspect, the invention provides a method of preparing a dendritic compound, including the step of contacting a compound of formula (I) with a glycoside compound that contains a free amino group.

It will be appreciated that any of the sub-scopes disclosed herein, e.g. with respect to A, B, D, E, G, X, $R^1$, $R^2$, $R^3$, $R^4$, $R^5$, n, m, p t, u, w, x, T, Y and Z may be combined with any of the other sub-scopes disclosed herein to produce further sub-scopes.

DETAILED DESCRIPTION

Definitions

The term "$C_1$-$C_6$alkyl" means any saturated hydrocarbon radical having up to 6 carbon atoms and is intended to include both straight- and branched-chain alkyl groups. Examples of alkyl groups include: methyl group, ethyl group, n-propyl group, iso-propyl group, n-butyl group, iso-butyl group, sec-butyl group, t-butyl group, n-pentyl group, 1,1-dimethylpropyl group, 1,2-dimethylpropyl group, 2,2-dimethylpropyl group, 1-ethylpropyl group, 2-ethylpropyl group, n-hexyl group and 1-methyl-2-ethylpropyl group.

The term "acyl" means C(=O)R' group, where R' is a $C_1$-$C_{30}$alkyl group, where $C_1$-$C_{30}$alkyl means any saturated hydrocarbon radical having up to 30 carbon atoms, and is intended to include straight chain alkyl groups. Examples include acetyl group.

Compounds of the Invention

The compounds of the invention are simple, easy to use "star burst PET-PEG" dendritic cores.

They are useful for the preparation of dendrimers, thereby providing a facile route to well-defined cluster molecules, e.g. pharmaceutical cluster molecules, as single compounds. The compounds of the invention are two-, three- or four-directional short-armed and long-armed dendritic cores. Some compounds of the invention are "pre-activated" (e.g. those where $R^5$ is a succinimidyl group) so that they can be used, without coupling reagents, for synthesising dendritic compounds. The dendritic core "arms" can be elongated in a controlled manner with suitable linkers, such as 6-8-carbon linkers or PEG linkers (one or two generations), making the "arms" shorter or longer as desired. The linkers are flexible and the tetrahedral model of the core is stable. Compounds of the invention that are succinimidyl esters are, advantageously, crystalline compounds. They are therefore stable and can be easily stored. Conveniently, the compounds of the invention can be purified by flash chromatography. Because of their simplicity of design, the compounds provide a novel approach to reaching larger sized dendrimers, but employing fewer "arms" (2-4 "arms" instead of 32-64), thus simplifying the dendrimer product. Dendritic cores with long carbon or PEG chains can be considered to be mimics of carbohydrate chains, but they avoid the costs and synthetic challenges associated with preparing linear oligosaccharides.

The invention relates to:
1. A compound of formula (I)

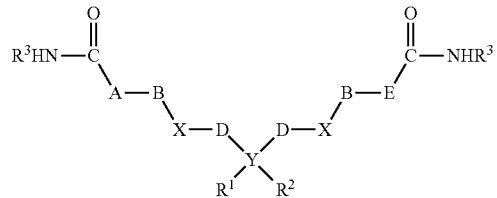

wherein:
Y is O;
B is O;
$R^1$ and $R^2$ are absent; and
either A, E, D and X are all $CH_2$; or A, D and X are all $CH_2$ and E is $(CH_2CH_2O)_t{}^\#CH_2$;
wherein # indicates a point of attachment of E to its adjacent carbonyl group;
t is an integer from 1 to 10;
or wherein:
Y is C;
$R^1$ and $R^2$ are both H; and
A, E, B and D are $CH_2$ and X is O;
or wherein:
Y is C;
A is $(CH_2)_u$
$R^1$ and $R^2$ are both H;
B, X, D and E are all absent; and
u is an integer from 1 to 10;
or wherein:
Y is C;
X is O;
B is $(CH_2)_p$;
A, E and D are all $CH_2$; and
$R^1$ is H, NHZ or $C_{1-6}$alkyl and $R^2$ is a radical of formula (i) or a radical of formula (ii)

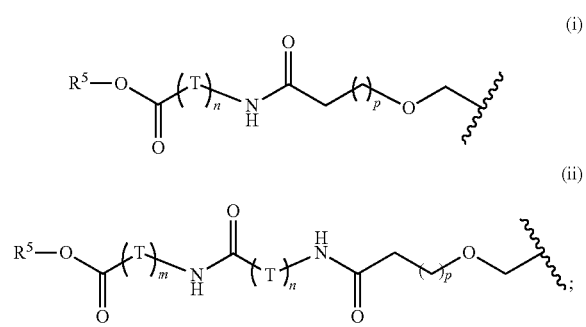

Z is H, acyl, $C(O)(CH_2)_wN(H)G$, *$CH_3$*C(O)— where *C denotes $^{13}$C or $^{14}$C, 4-carboxytetramethylrhodamine, resorcinolphthalein, 7-amino-4-methyl-6-sulfocoumarin-3-acetic acid, 4,4-difluoro-4-bora-3a,4a-diaza-s-indacene or 1-{3-{[4-(2-cyclooctyn-1-ylmethyl)benzoyl]amino}propyl}-4-{2-[4-(dimethylamino)phenyl]ethenyl}pyridinium hexafluorophosphate;
w is an integer from 1 to 11;
G is H, acyl, t-butoxycarbonyl, 2,2,2-trichloroethyloxycarbonyl, 9-fluorenylmethoxycarbonyl, benzyloxycarbonyl,*$CH_3$*CO— where *C denotes $^{13}$C or $^{14}$C, 4-carboxytetramethylrhodamine, resorcinolphthalein, 7-amino-4-methyl-6-sulfocoumarin-3-acetic acid, 4,4-difluoro-4-bora-3a,4a-diaza-s-indacene or 1-{3-{[4-(2- cyclooctyn-1-ylmethyl)benzoyl]amino}propyl}-4-{2-[4-(dimethylamino)phenyl]ethenyl}pyridinium hexafluorophosphate;
or wherein:
Y is C;
X is O;
B is $(CH_2)_p$;
A, E and D are all $CH_2$; and
$R^1$ and $R^2$, both the same, are a radical of formula (i) or a radical of formula (ii)

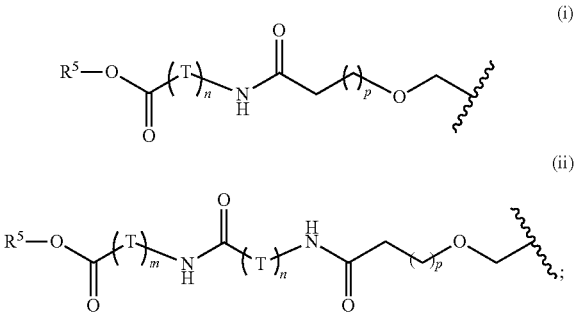

$R^3$ is a radical of formula (iii) or a radical of formula (iv)

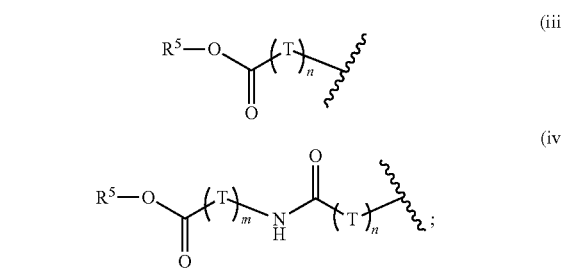

each T is independently selected from the group consisting of $(CH_2CH_2O)_xCH_2CH_2$ and $CH_2$;
each x is independently an integer from 1 to 12;
m is an integer from 1 to 11, provided that when T is $(CH_2CH_2O)_xCH_2CH_2$ then m is 1;
n is an integer from 1 to 11, provided that when T is $(CH_2CH_2O)_xCH_2CH_2$ then n is 1;
p is an integer from 1 to 5;
$R^5$ is H,

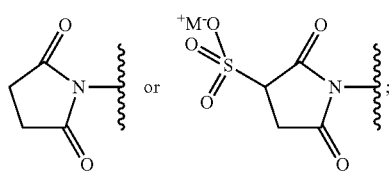

and
M is sodium or ammonium.

2. A compound as described in the above paragraph 1 wherein each T is $CH_2$.
3. A compound as described in the above paragraph 1 wherein at least one T is $(CH_2CH_2O)_xCH_2CH_2$.
4. A compound as described in the above paragraph 1 wherein m is an integer from 5 to 8.
5. A compound as described in the above paragraph 1 or 2 wherein n is an integer from 5 to 8.
6. A compound as described in any one of the above paragraphs 1 to 5 wherein Y is C.
7. A compound as described in any one of the above paragraphs 1 to 6 wherein $R^3$ is a radical of formula (iii)

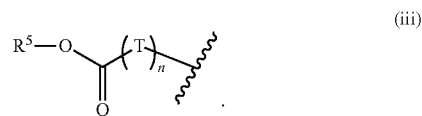

8. A compound as described in any one of the above paragraphs 1 to 6 wherein $R^3$ is a radical of formula (iv)

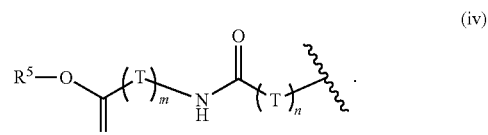

9. A compound as described in any one of the above paragraphs 1 to 8 wherein $R^1$ and $R^2$ are both a radical of formula (i)

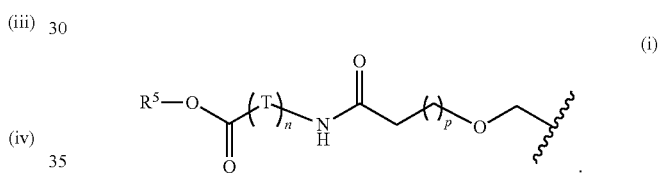

10. A compound as described in any one of the above paragraphs 1 to 8 wherein $R^1$ and $R^2$ are both a radical of formula (ii)

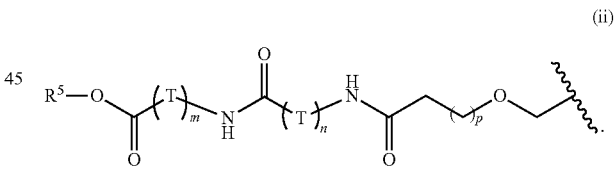

11. A compound as described in any one of the above paragraphs 1 to 8 wherein $R^1$ is H or $C_{1-6}$alkyl.
12. A compound as described in any one of the above paragraphs 1 to 8 wherein $R^1$ is $NH_2$.
13. A compound as described in any one of the above paragraphs 1 to 12 wherein $R^5$ is

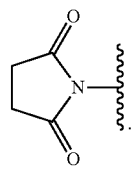

14. A compound as described in any one of the above paragraphs 1 to 5, 7 to 8 or 13 wherein Y is O; B is O; $R^1$ and $R^2$ are absent; and either A, E, D and X are all $CH_2$ or A, D and X are all $CH_2$ and E is $(CH_2CH_2O)_tCH_2$; and t is an integer from 1 to 10.

15. A compound as described in any one of the above paragraphs 1 to 8 or 13 wherein Y is C;

$R^1$ and $R^2$ are both H; A, E, B and D are $CH_2$ and X is O.

16. A compound as described in any one of the above paragraphs 1 to 8 or 13 wherein Y is C; A is $(CH_2)_u$; $R^1$ and $R^2$ are both H; B, X, D and E are all absent; and u is an integer from 1 to 10.

17. A compound as described in any one of the above paragraphs 1 to 8 or 13 wherein:

Y is C; X is O; A, E and D are all $CH_2$; B is $(CH_2)_p$;

$R^1$ is H, NHZ or $C_{1-6}$alkyl;

$R^2$ is a radical of formula (i) or a radical of formula (ii)

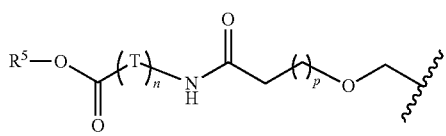
(i)

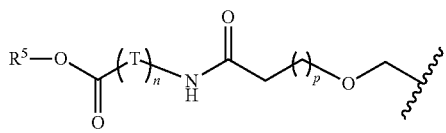
(ii)

Z is H, acyl, $C(O)(CH_2)_wNH(G)$, *$CH_3$*CO— where *C denotes $^{13}$C or $^{14}$C, 4 carboxytetramethylrhodamine, resorcinolphthalein, 7-amino-4-methyl-6-sulfocoumarin-3-acetic acid, 4,4-difluoro-4-bora-3a,4a-diaza-s-indacene or 1-{3-{[4-(2-cyclooctyn-1-ylmethyl)benzoyl]amino}propyl}-4-{2-[4-(dimethylamino)phenyl]ethenyl}pyridinium hexafluorophosphate;

w is an integer from 1 to 11;

G is H, acyl, t-butoxycarbonyl, 2,2,2-trichloroethyloxycarbonyl, 9-fluorenylmethoxycarbonyl, benzyloxycarbonyl, *$CH_3$*CO— where *C denotes $^{13}$C or $^{14}$C, 4-carboxytetramethylrhodamine, resorcinolphthalein, 7-amino-4-methyl-6-sulfocoumarin-3-acetic acid, 4,4-difluoro-4-bora-3a,4a-diaza-s-indacene or 1-{3-{[4-(2-cyclooctyn-1-ylmethyl)benzoyl]amino}propyl}-4-{2-[4-(dimethylamino)phenyl]ethenyl}pyridinium hexafluorophosphate.

18. A compound as described in any one of the above paragraphs 1 to 9 or 13 wherein, Y is C; X is O; A, E and D are all $CH_2$; B is $(CH_2)_p$; $R^1$ and $R^2$, both the same, are a radical of formula (i)

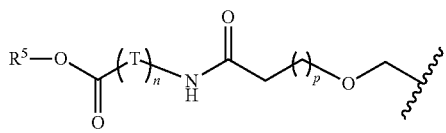
(i)

$R^3$ is a radical of formula (iii)

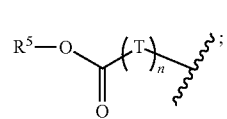
(iii)

and and p is 1.

19. A compound as described in any one of the above paragraphs 1 to 8 or 10 or 13 wherein Y is C; X is O; A, E and D are all $CH_2$; B is $(CH_2)_p$; $R^1$ and $R^2$, both the same, are a radical of formula (ii)

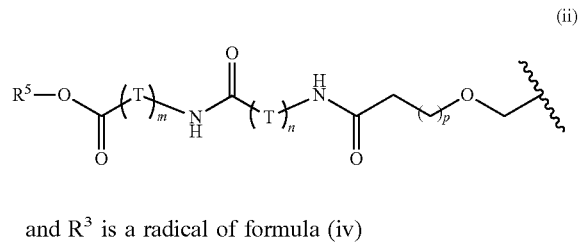
(ii)

and $R^3$ is a radical of formula (iv)

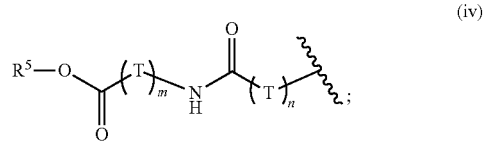
(iv)

and p is 1.

20. A compound as described in any one of the above paragraphs 1 to 8 or 13 or 15 wherein Y is C; $R^1$ and $R^2$ are both H; A, E, B and D are $CH_2$; X is O; and $R^3$ is a radical of formula (iii)

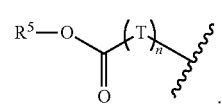
(iii)

21. A compound as described in any one of the above paragraphs 1 to 8 or 13 or 15 wherein Y is C; $R^1$ and $R^2$ are both H; A, E, B and D are $CH_2$; X is O; and $R^3$ is a radical of formula (iv)

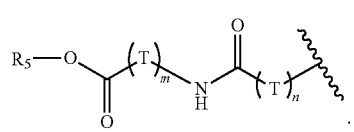
(iv)

22. A compound as described in any one of the above paragraphs 1 to 8 or 13 or 17 wherein Y is C; X is O; A, E and D are all $CH_2$; B is $(CH_2)_p$; $R^1$ is H; $R^2$ is a radical of formula (i)

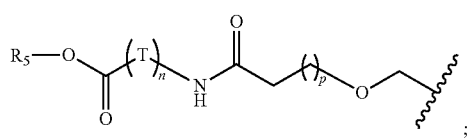

R³ is a radical of formula (iii)

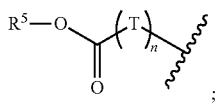

and p is 1.

23. A compound as described in any one of the above paragraphs 1 to 8 or 13 or 17 wherein Y is C; X is O; A, E and D are all CH₂; B is (CH₂)$_p$; R¹ is H; R² is a radical of formula (ii)

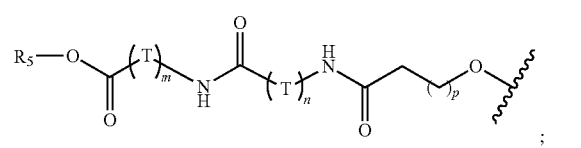

R³ is a radical of formula (iv)

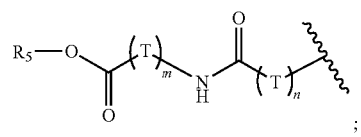

and p is 1.

24. A compound as described in any one of the above paragraphs 1 to 8 or 13 or 17 wherein Y is C; X is O; A, E and D are all CH₂; B is (CH₂)$_p$; R¹ is H; R² is a radical of formula (ii)

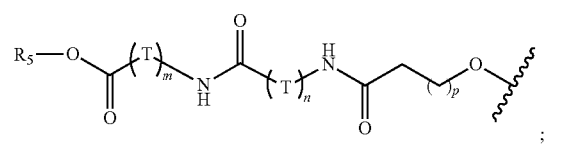

R³ is a radical of formula (iii)

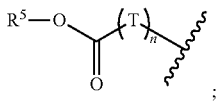

and p is 1.

25. A compound as described in any one of the above paragraphs 1 to 8 or 13 or 17 wherein Y is C; X is O; A, E and D are all CH₂; B is (CH₂)$_p$; R¹ is H; R² is a radical of formula (i)

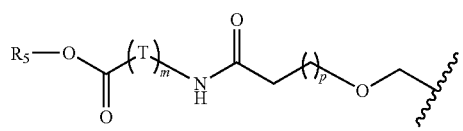

and R³ is a radical of formula (iv)

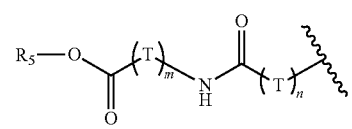

and p is 1.

26. A compound as described in any one of the above paragraphs 1 to 8 or 13 or 16 wherein Y is C; A is (CH₂)$_u$; R¹ and R² are both H; B, X, D and E are all absent; u is an integer from 1 to 10; and R³ is a radical of formula (iii)

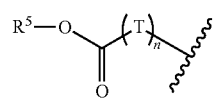

27. A compound as described in any one of the above paragraphs 1 to 8 or 13 or 16 wherein Y is C; A is (CH₂)$_u$; R¹ and R² are both H; B, X, D and E are all absent; u is an integer from 1 to 10; and R³ is a radical of formula (iv)

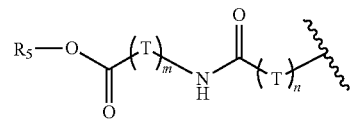

28. A compound as described in any one of the above paragraphs 1 to 8 or 13 or 14 wherein Y is O; B is O; R¹ and R² are absent; and either A, E, D and X are all CH₂ or A, D and X are all CH₂ and E is (CH₂CH₂O)$_t$CH₂; t is an integer from 1 to 2; and R³ is a radical of formula (iii)

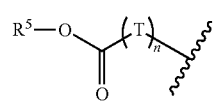

29. A compound as described in any one of the above paragraphs 1 to 8 or 13 or 14 wherein Y is O; B is O; R¹ and R² are absent; and either A, E, D and X are all CH₂ or A, D and X are all CH₂ and E is (CH₂CH₂O)$_t$CH₂; t is an integer from 1 to 2; and R³ is a radical of formula (iv)

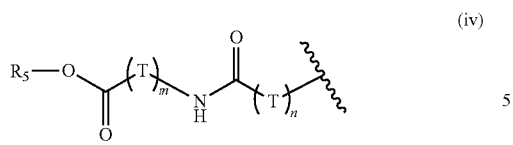
30. A compound as described in any one of the above paragraphs 1 to 10, 17 to 19 or 22 to 25 wherein p is 1.
31. A compound as described in any one of the above paragraphs 1 to 30 wherein M is sodium.
32. A compound as described in the above paragraph 1, selected from the group consisting of:

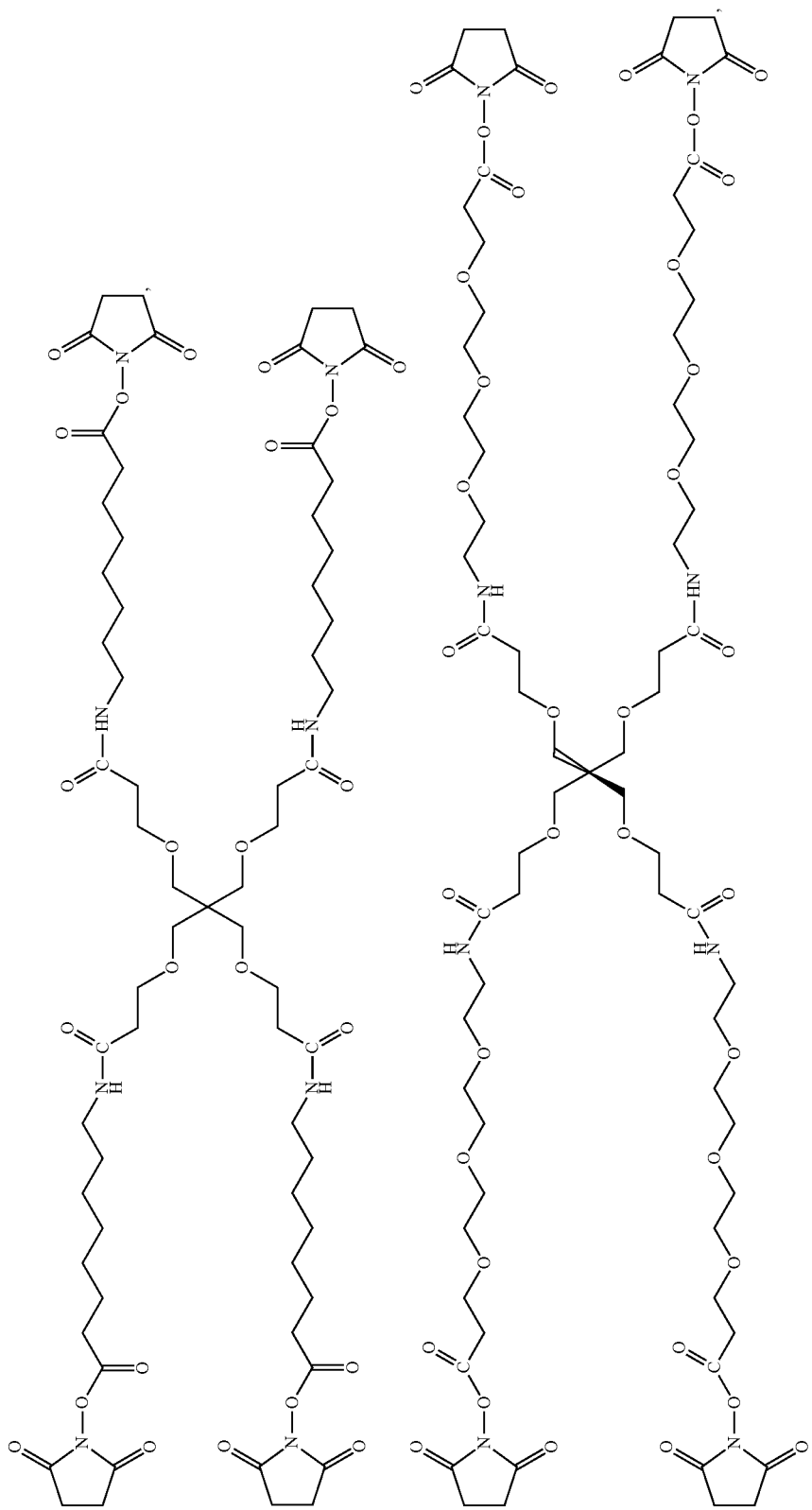

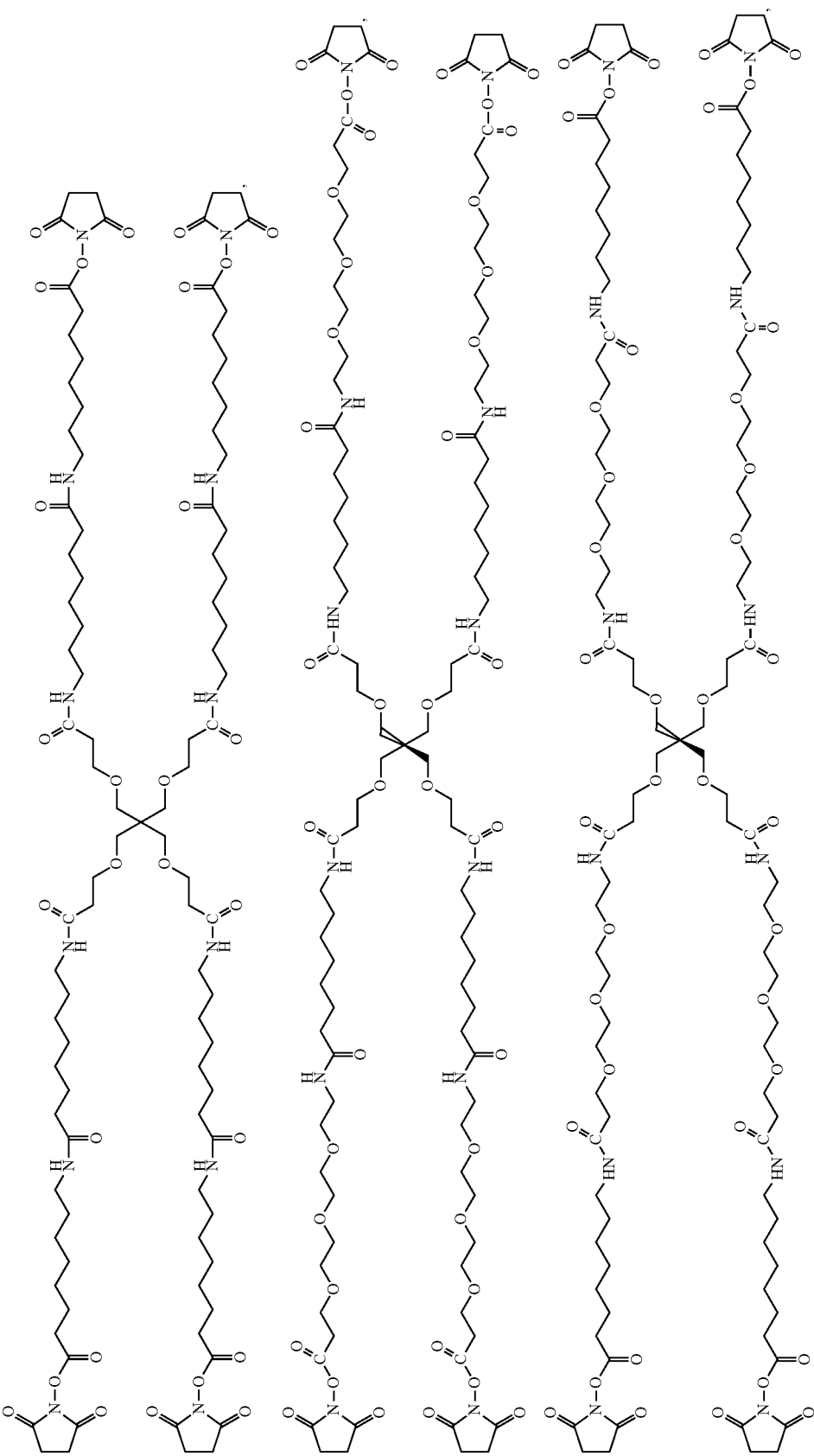

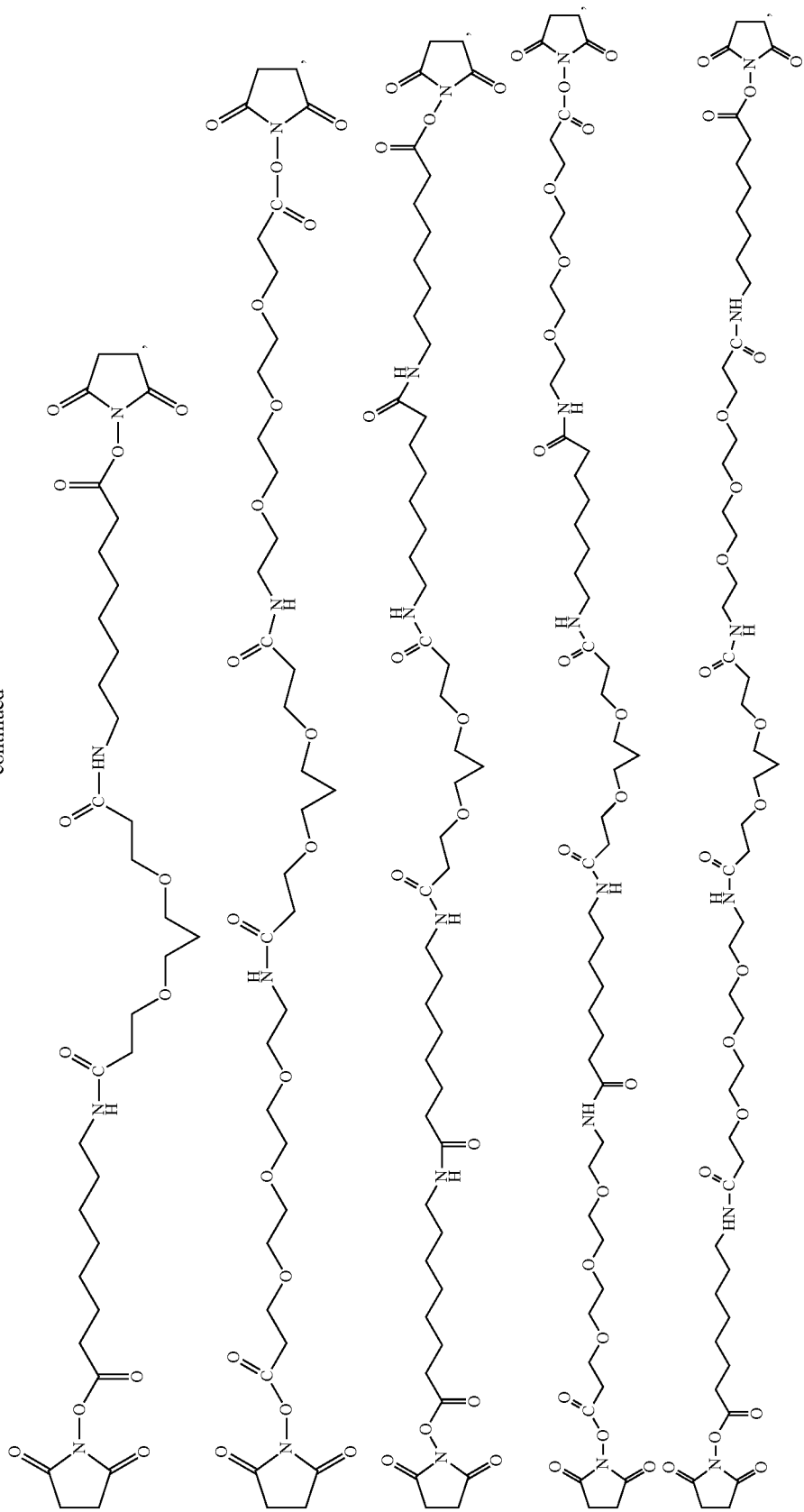

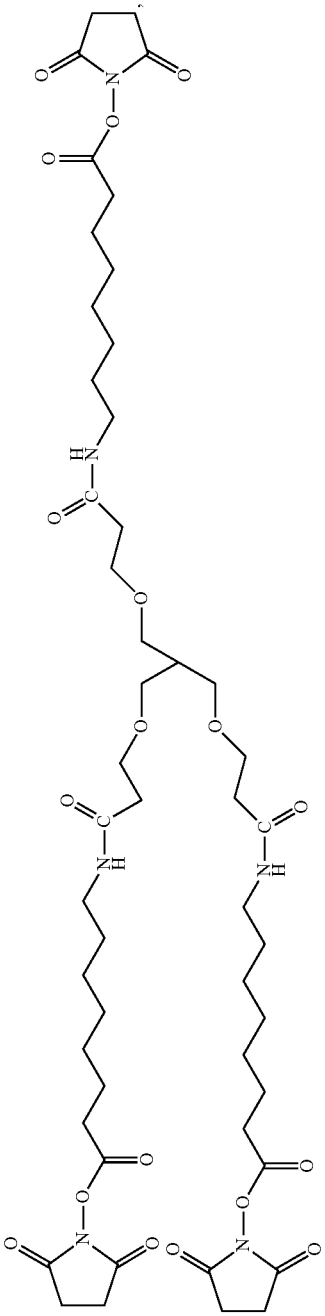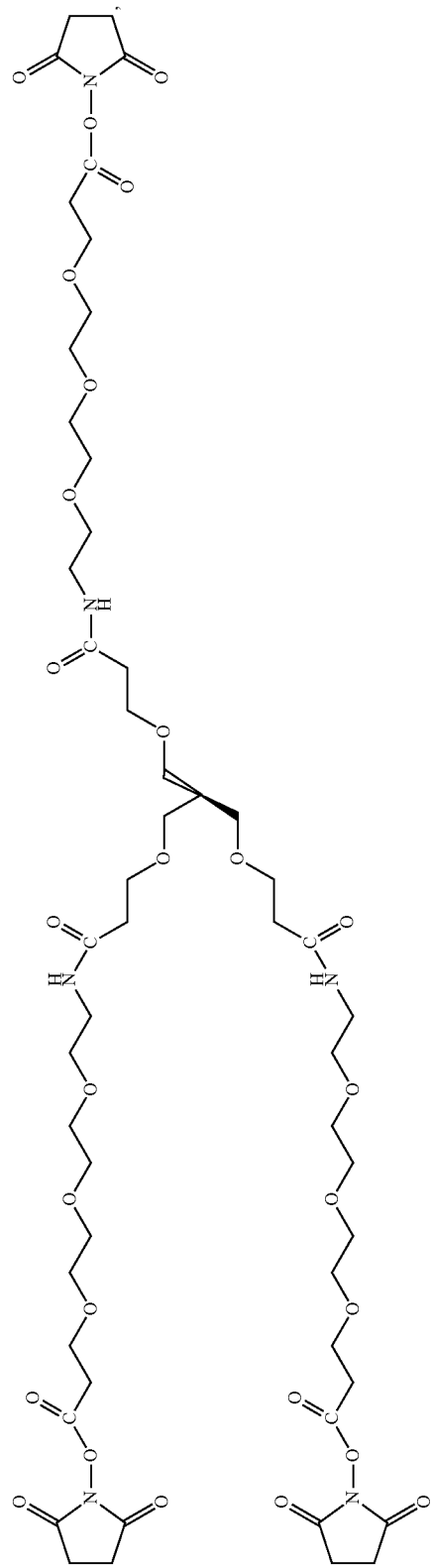

-continued
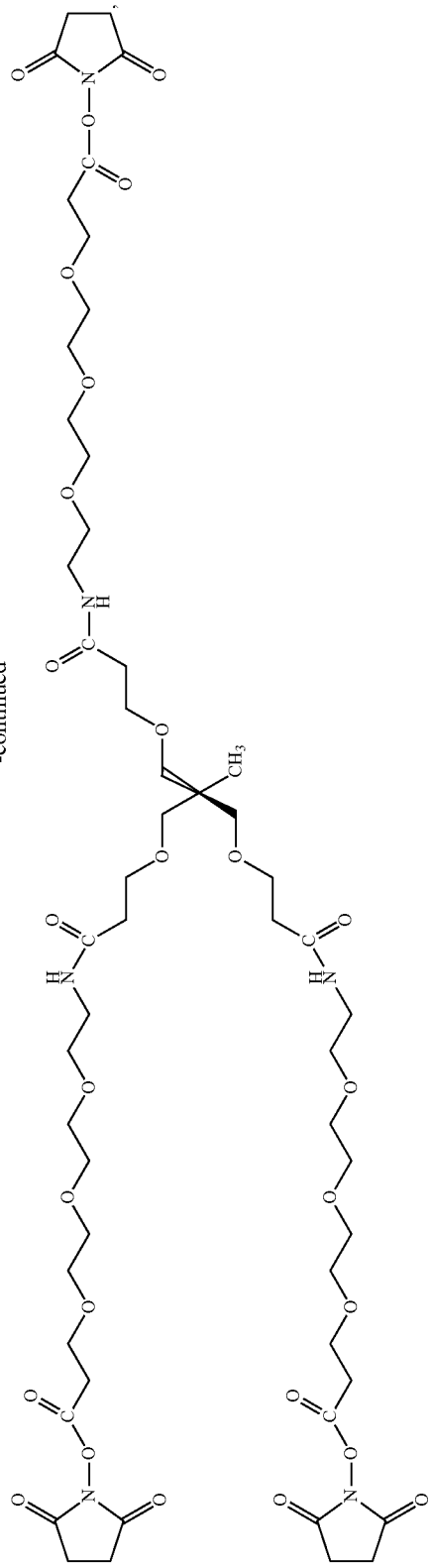
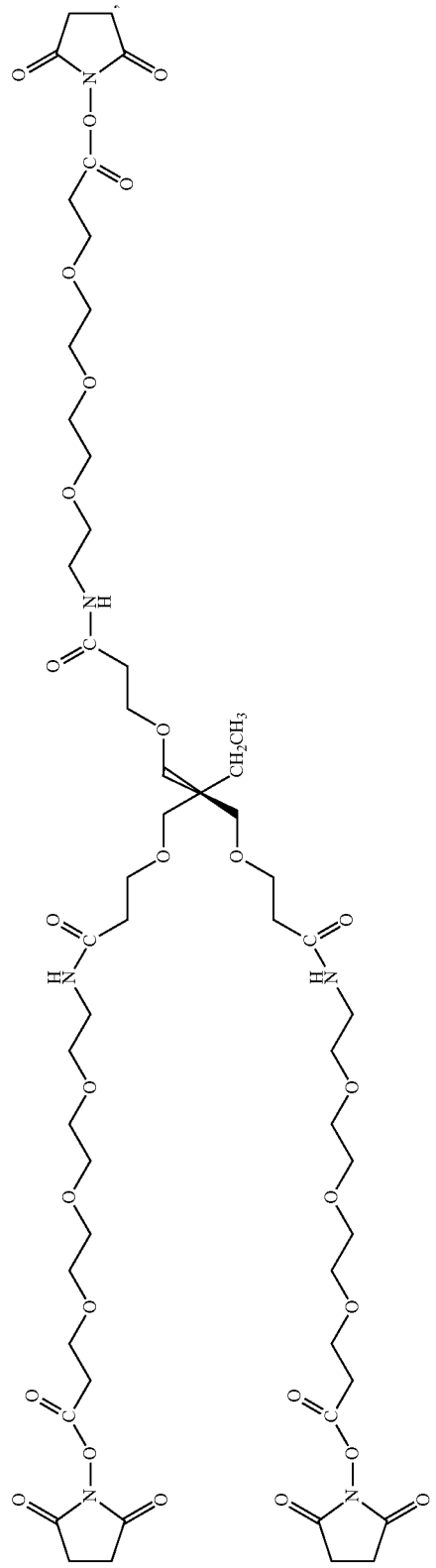

-continued
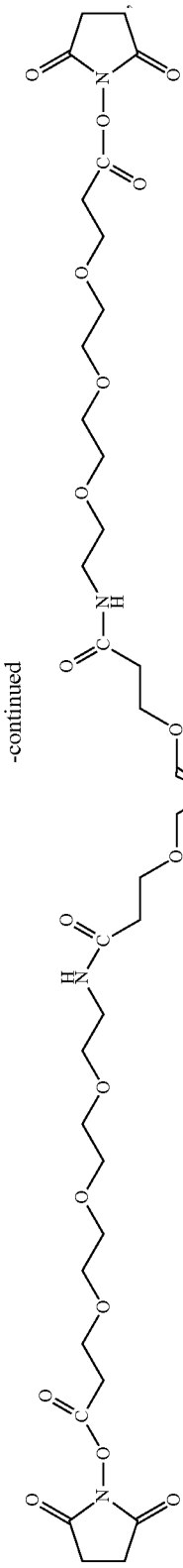
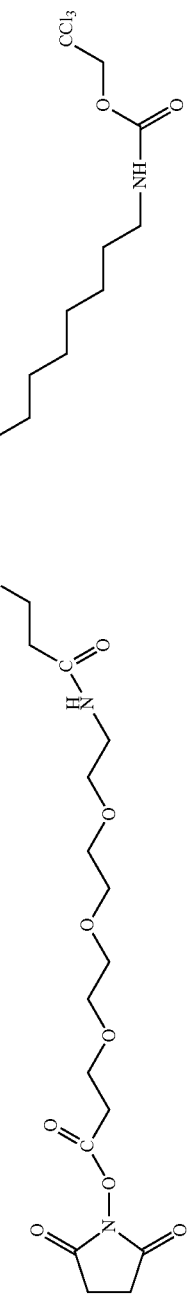
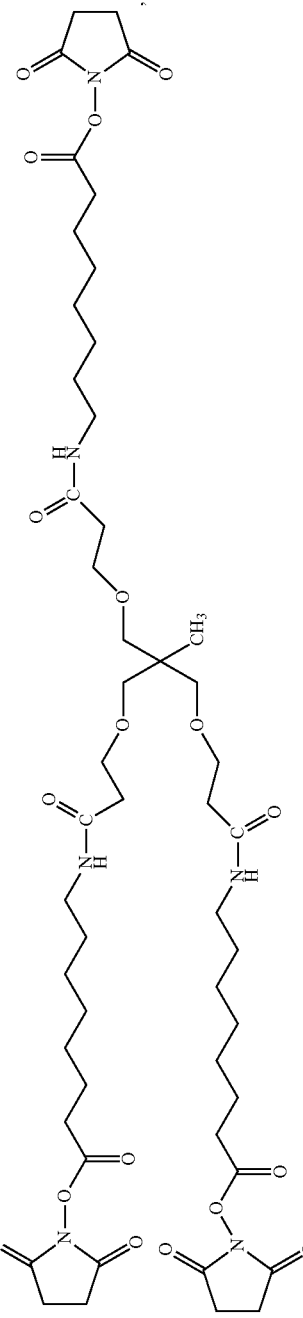
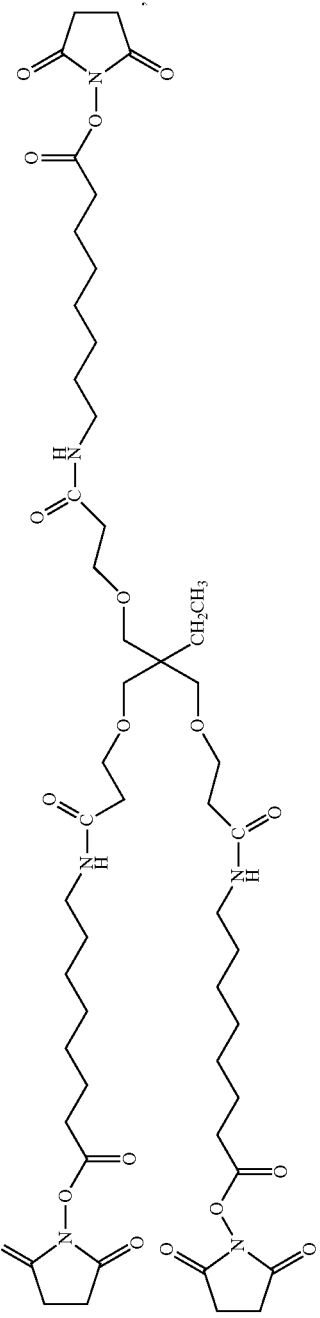

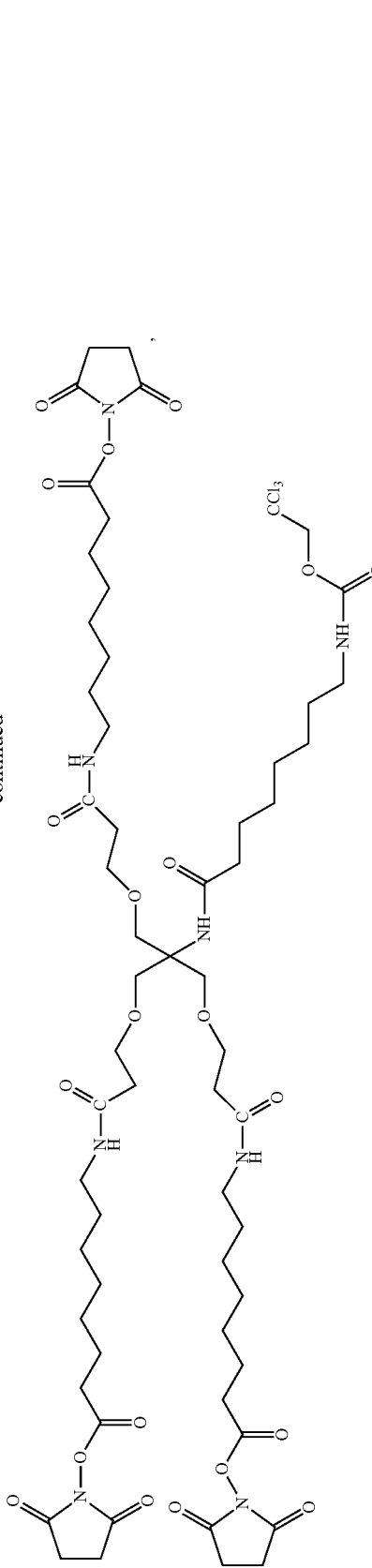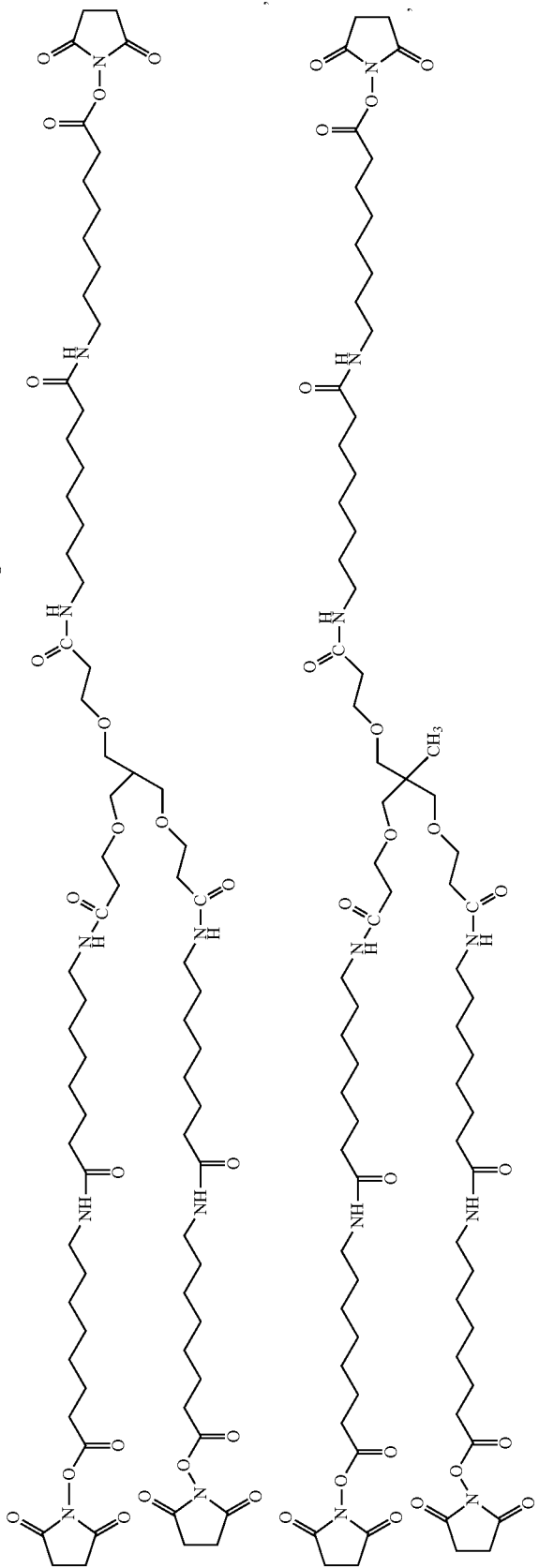

-continued
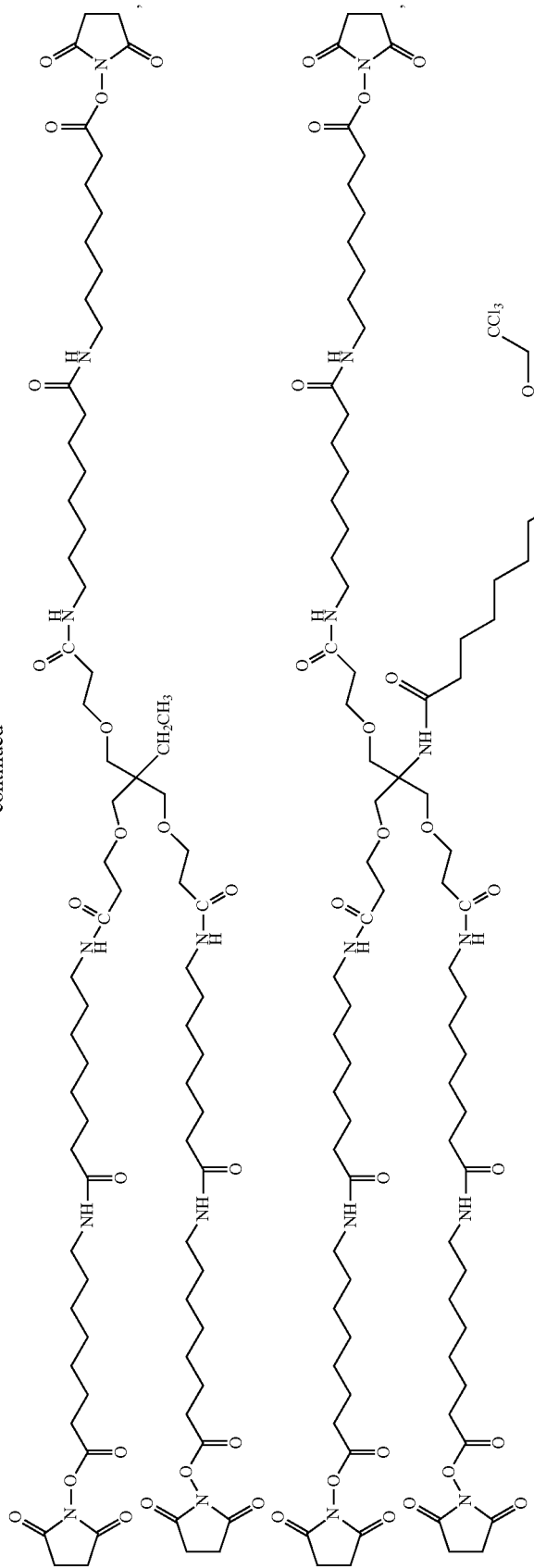
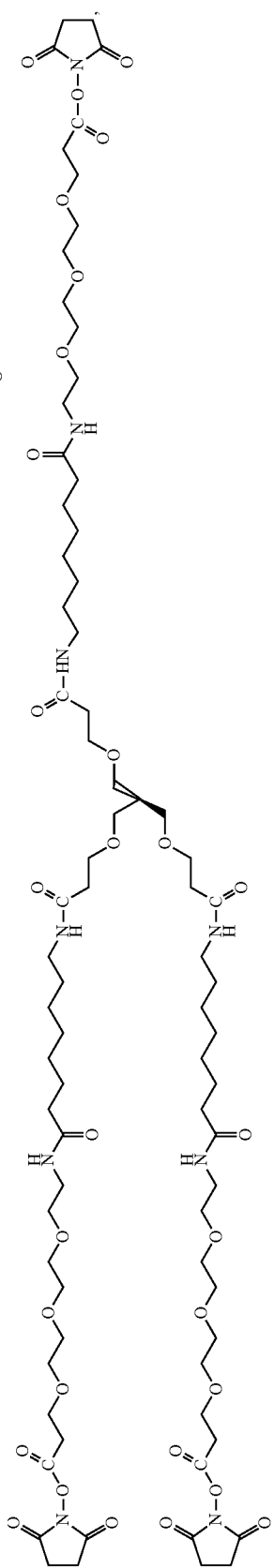

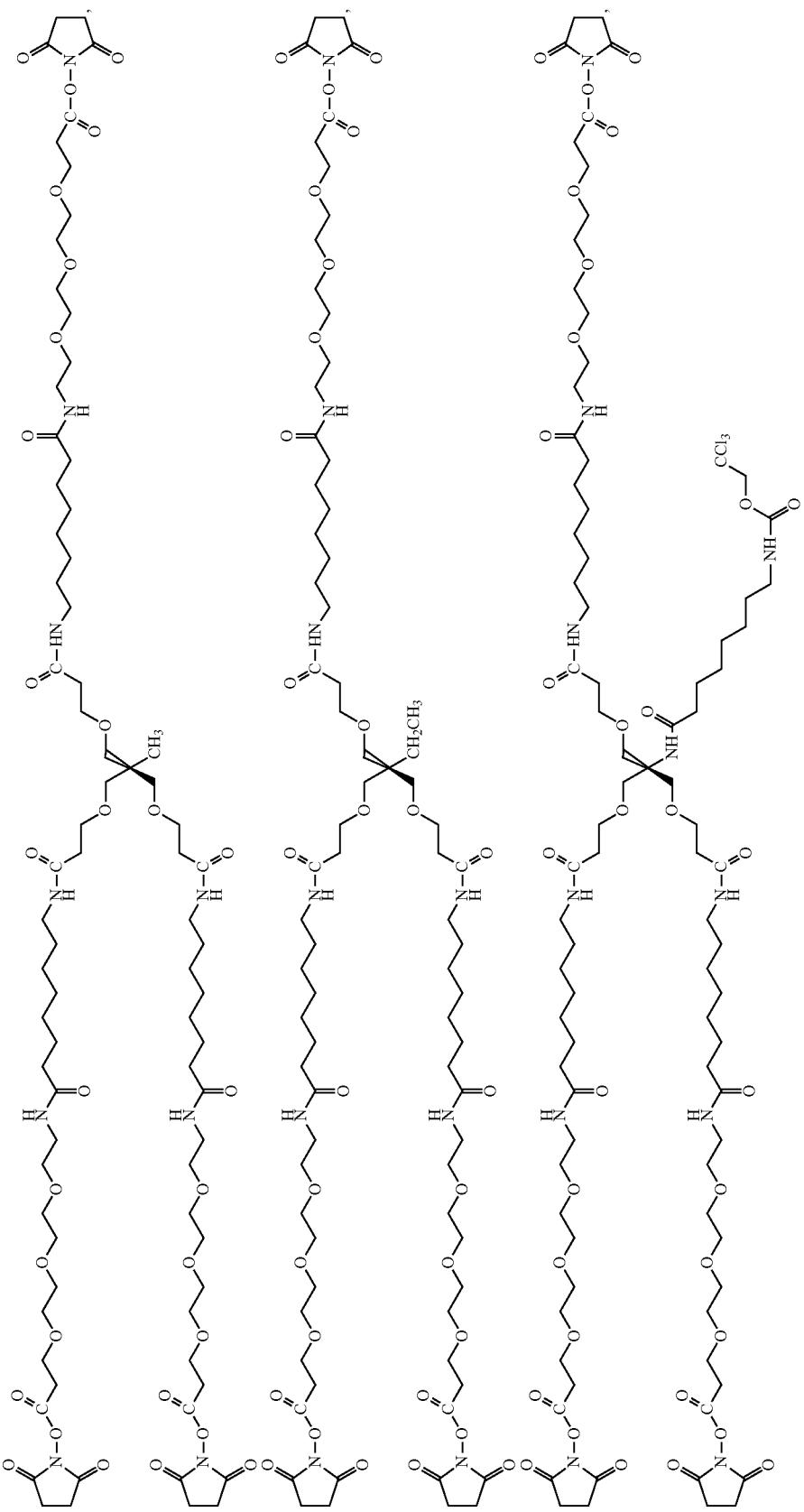

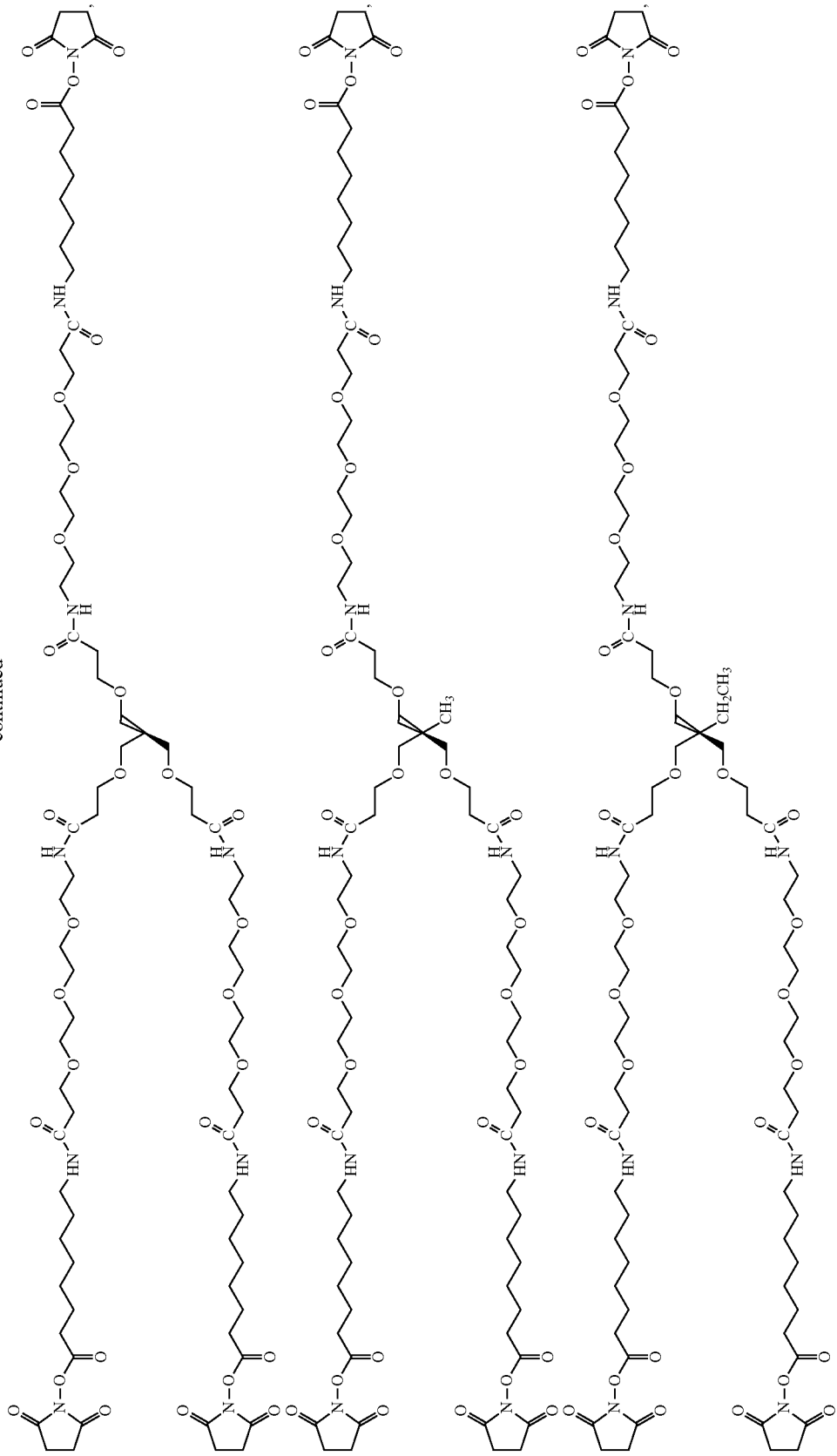

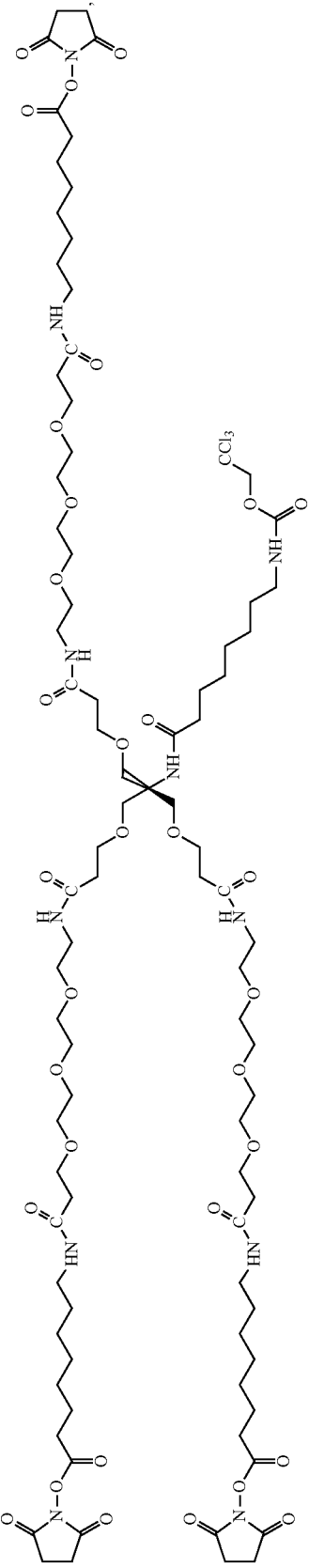
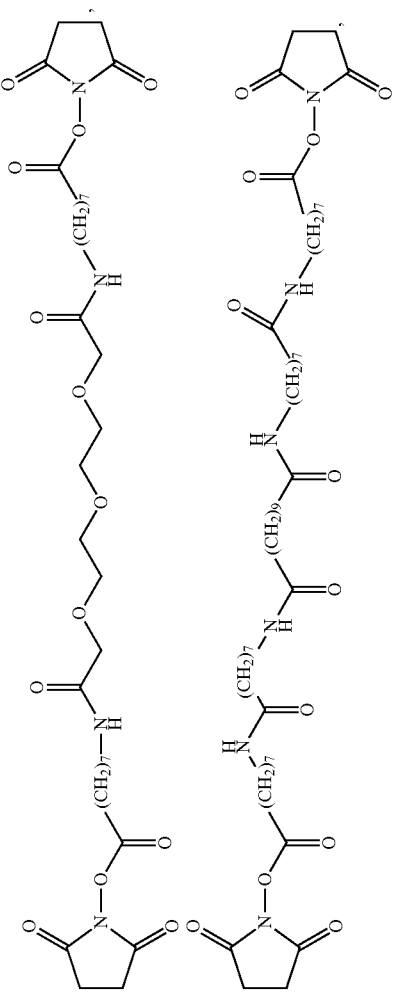

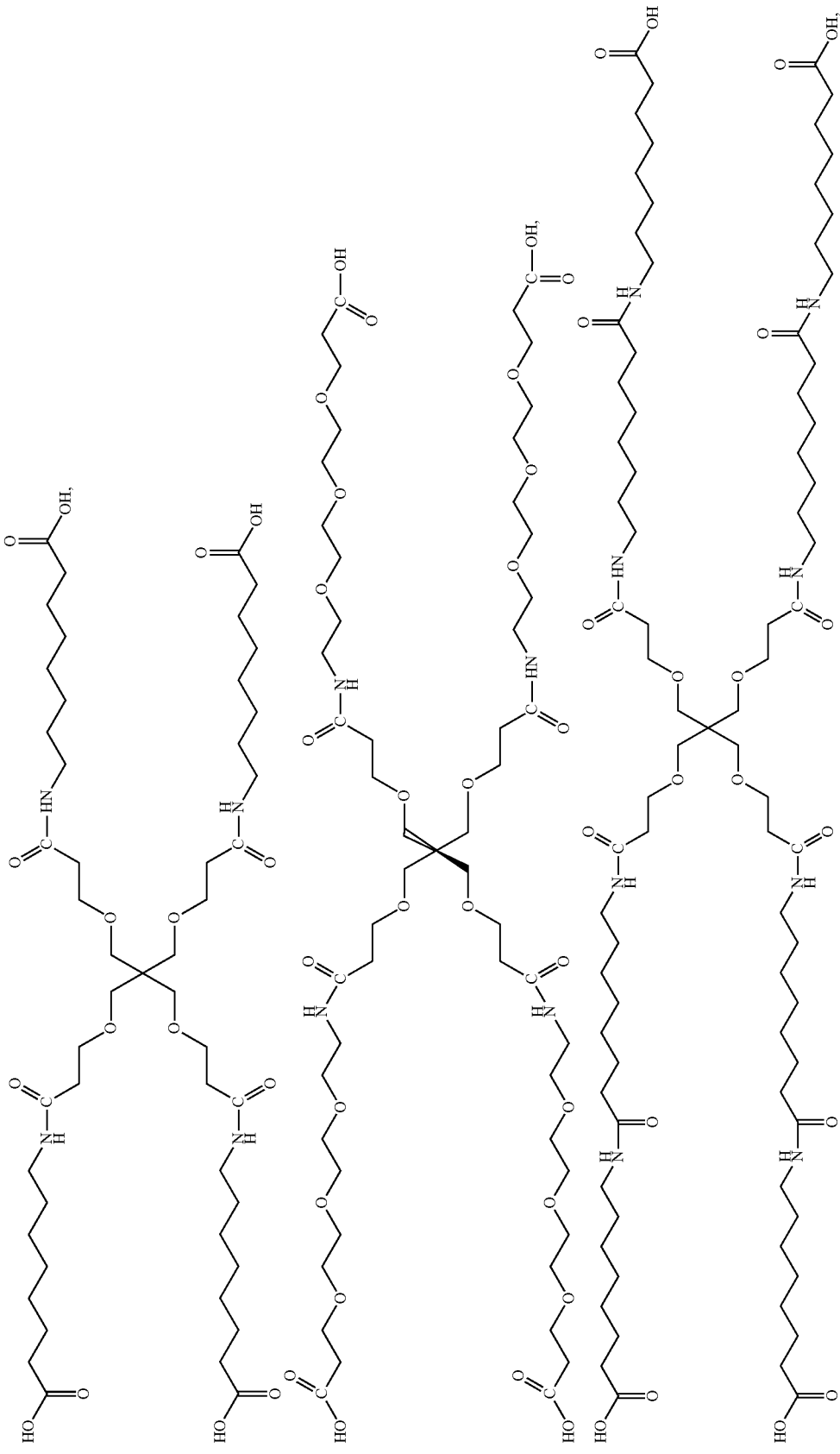

-continued
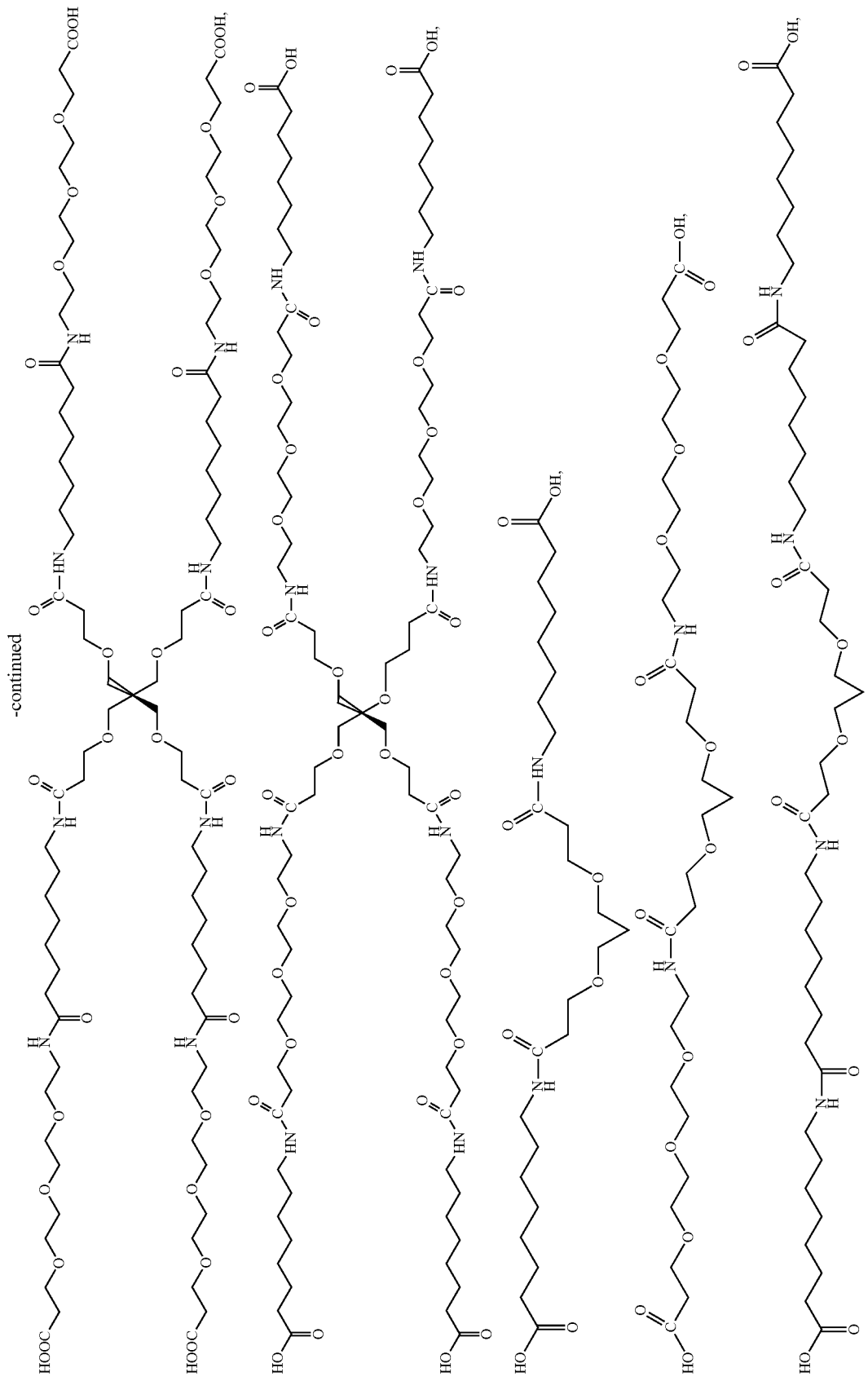

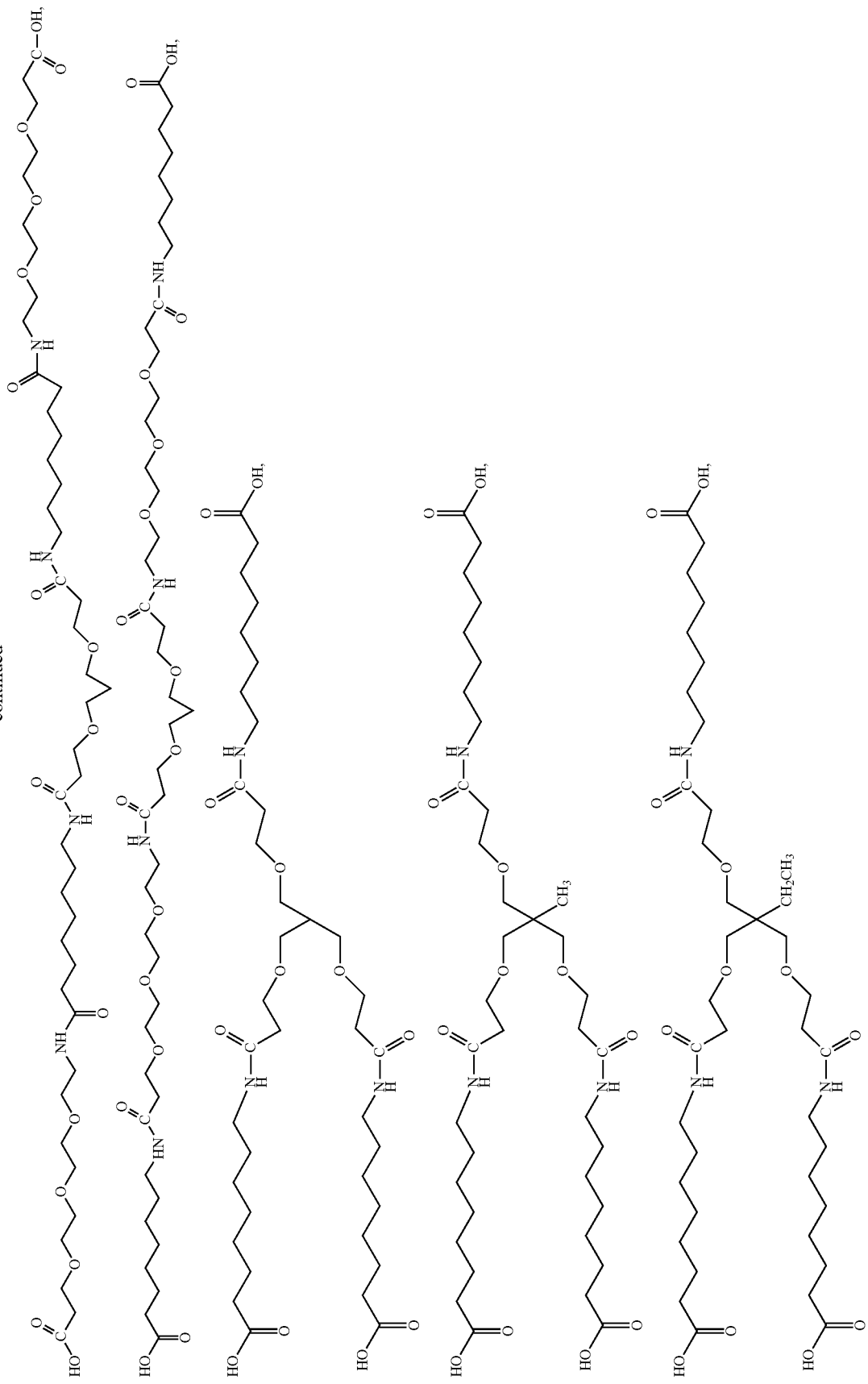

-continued
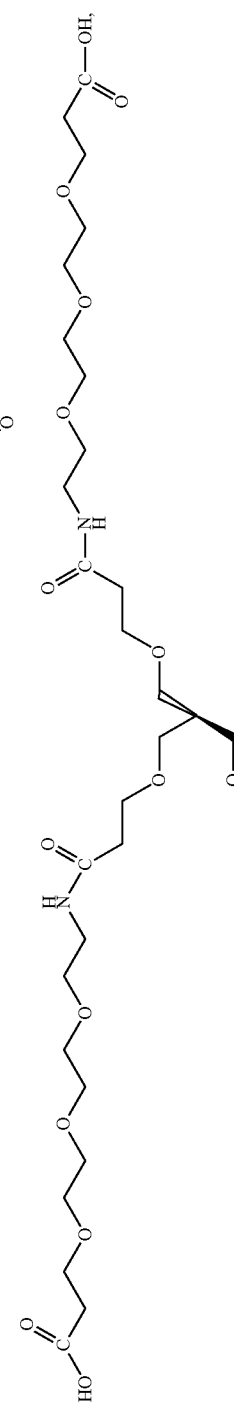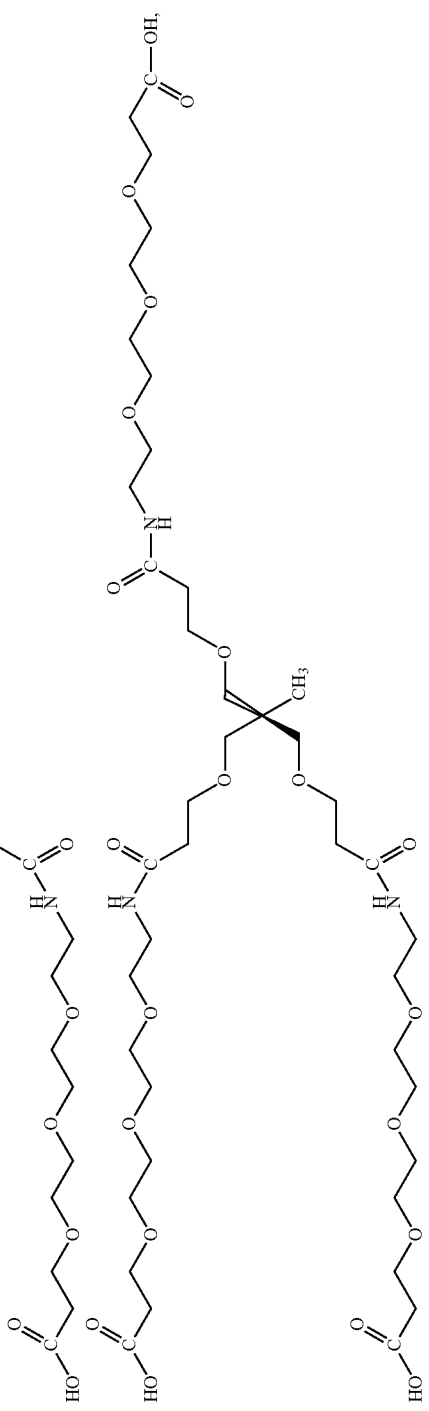

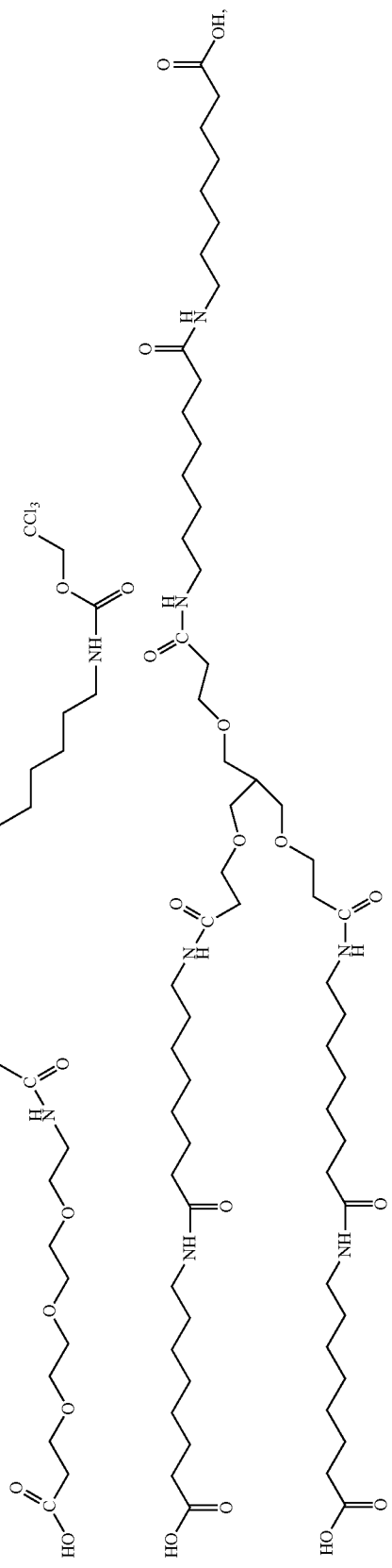

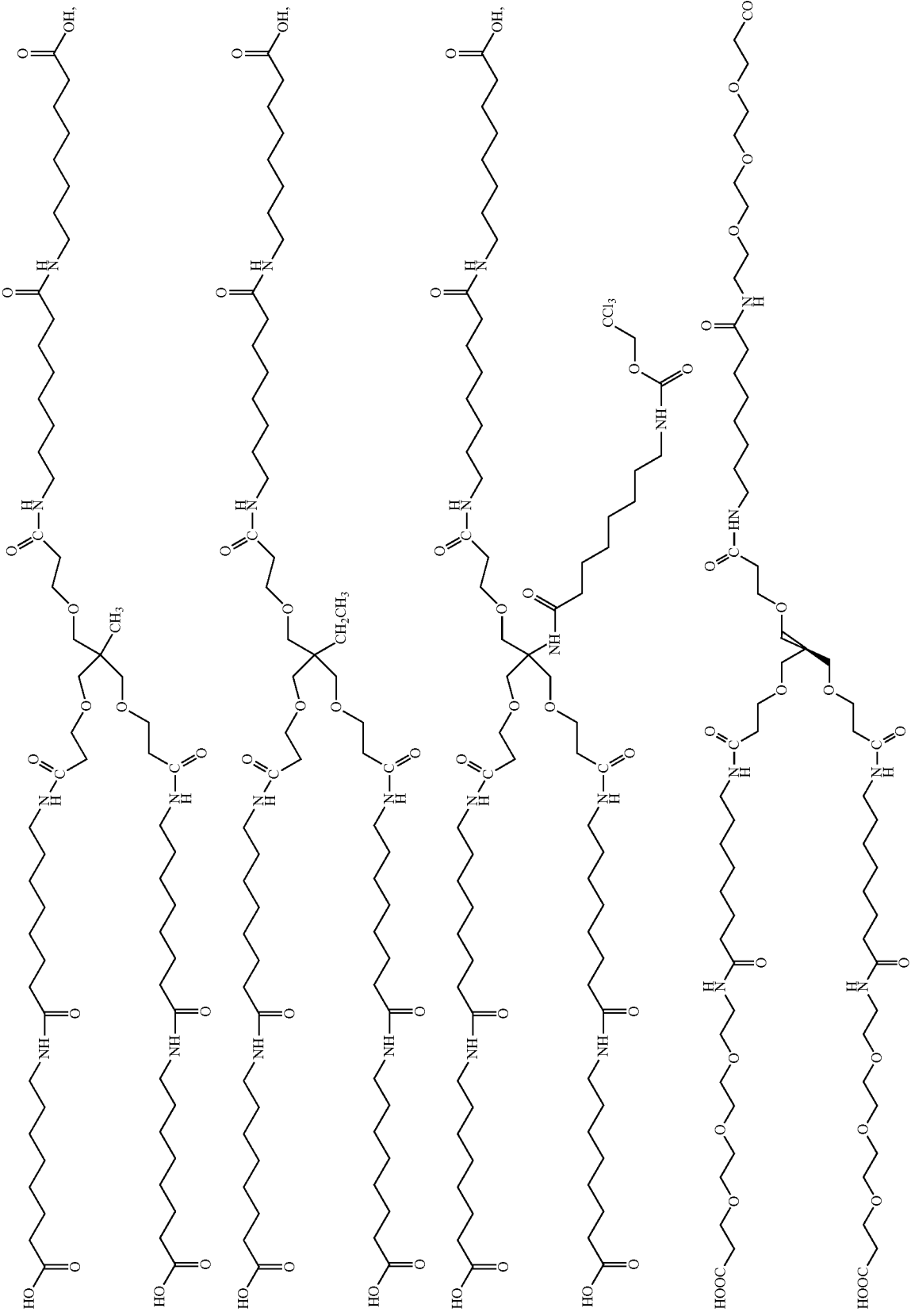

-continued
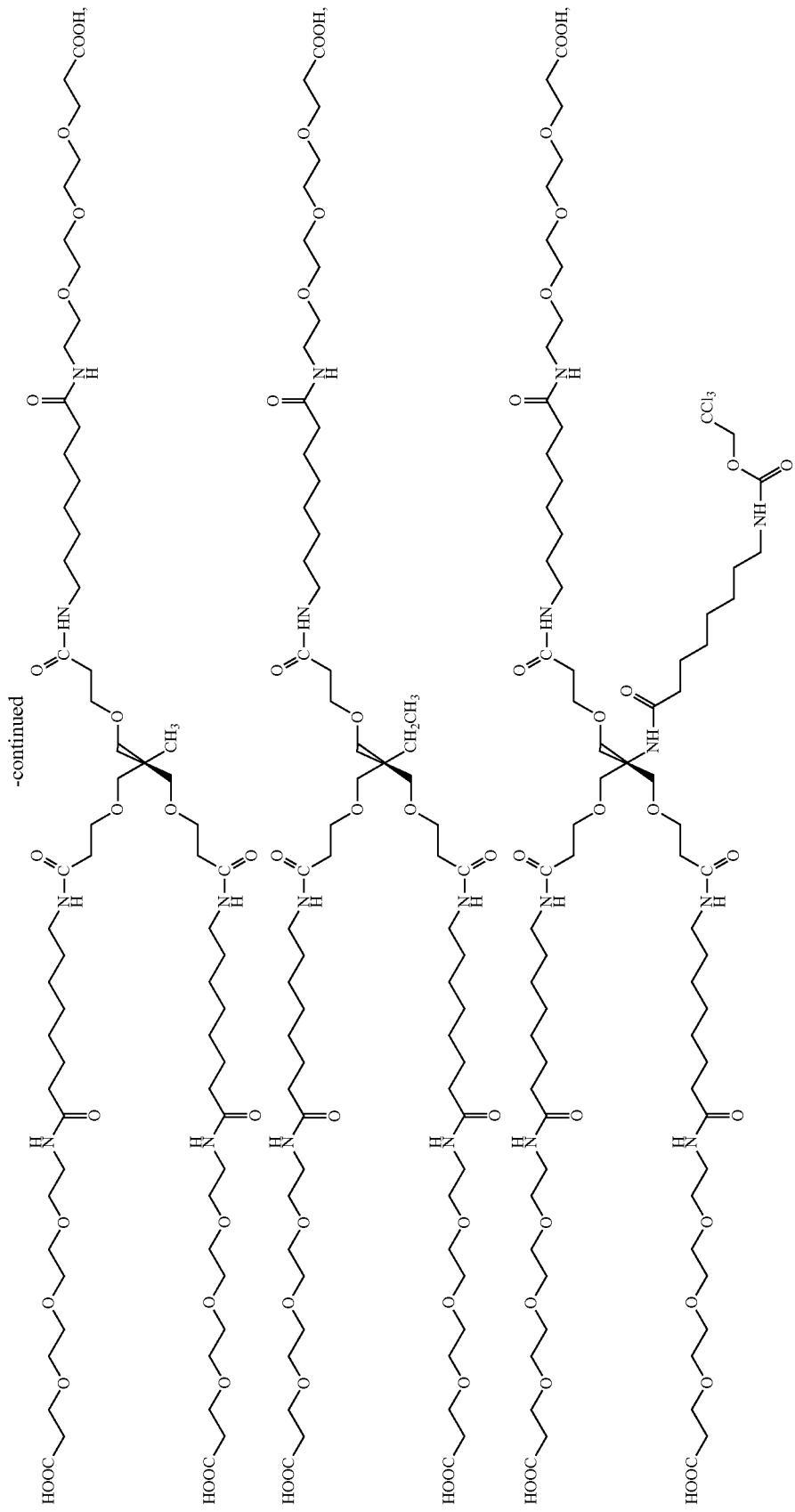

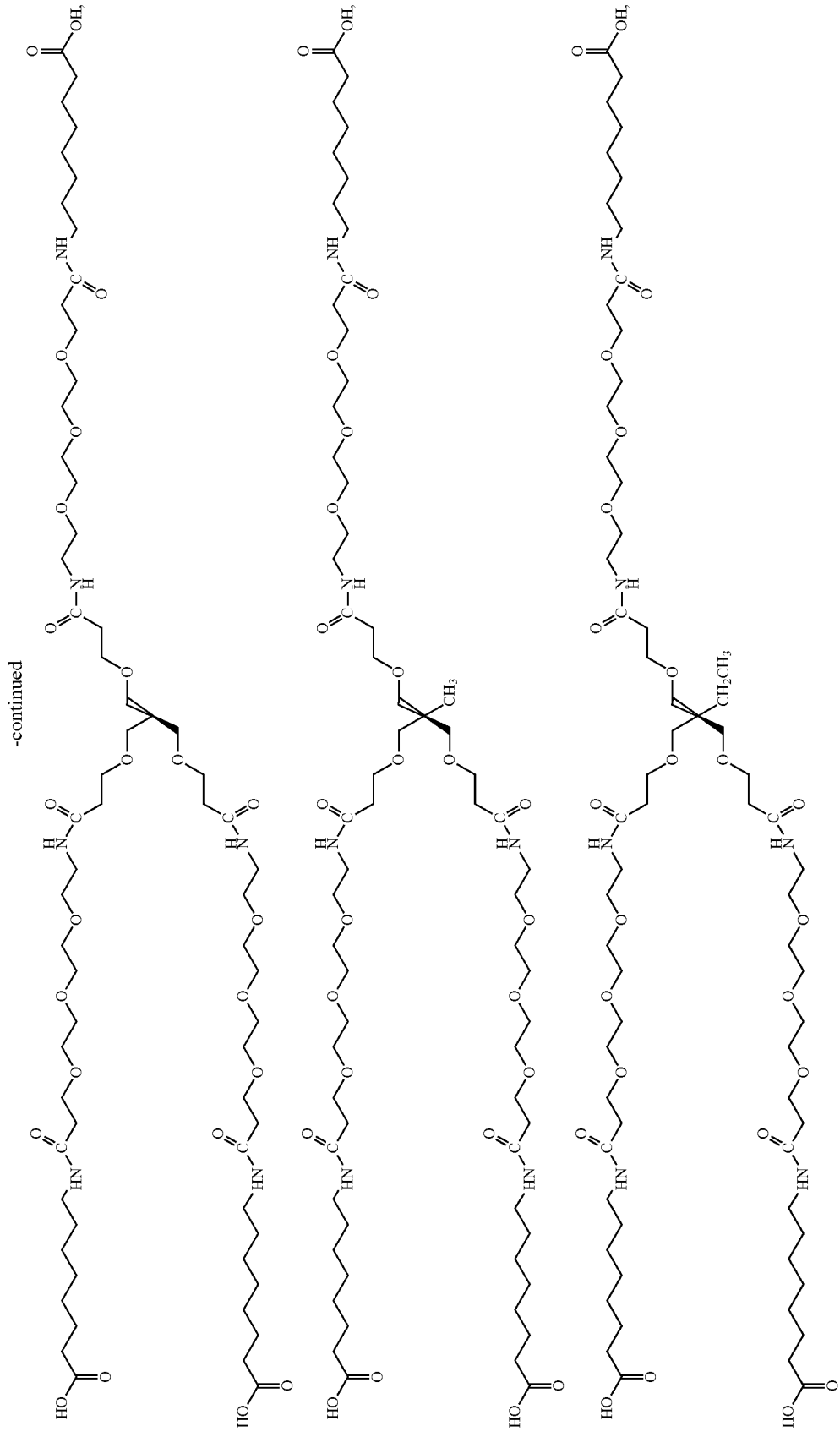

-continued
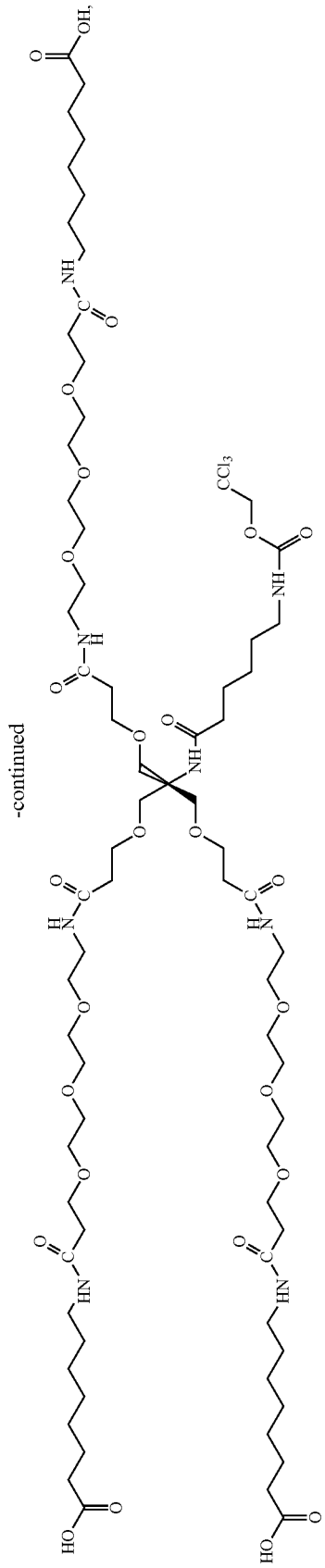
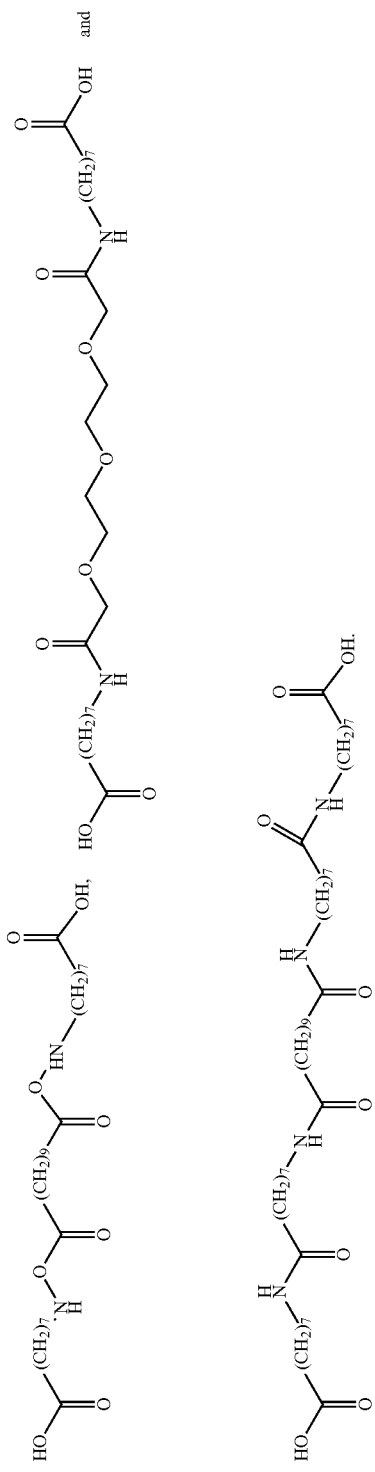

33. A compound selected from the group consisting of:

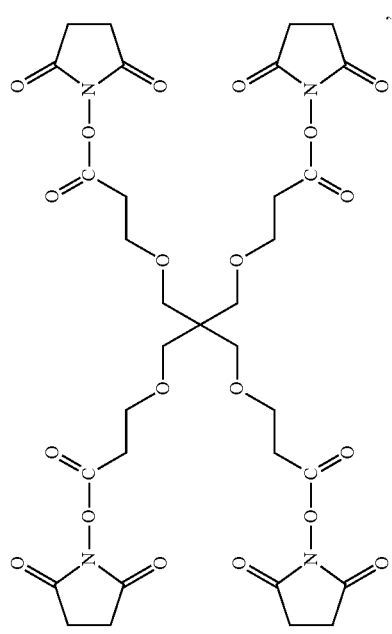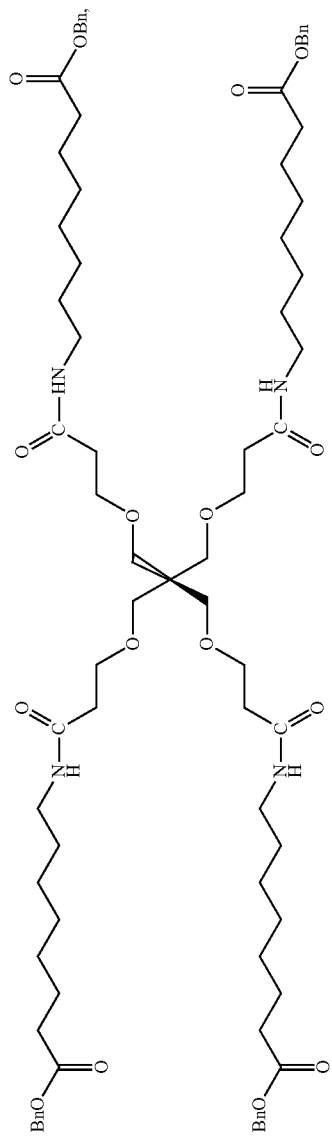

-continued
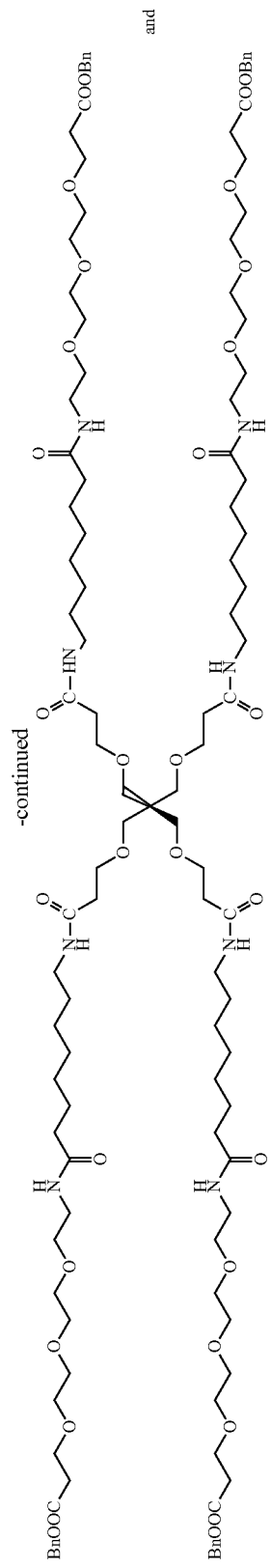
and
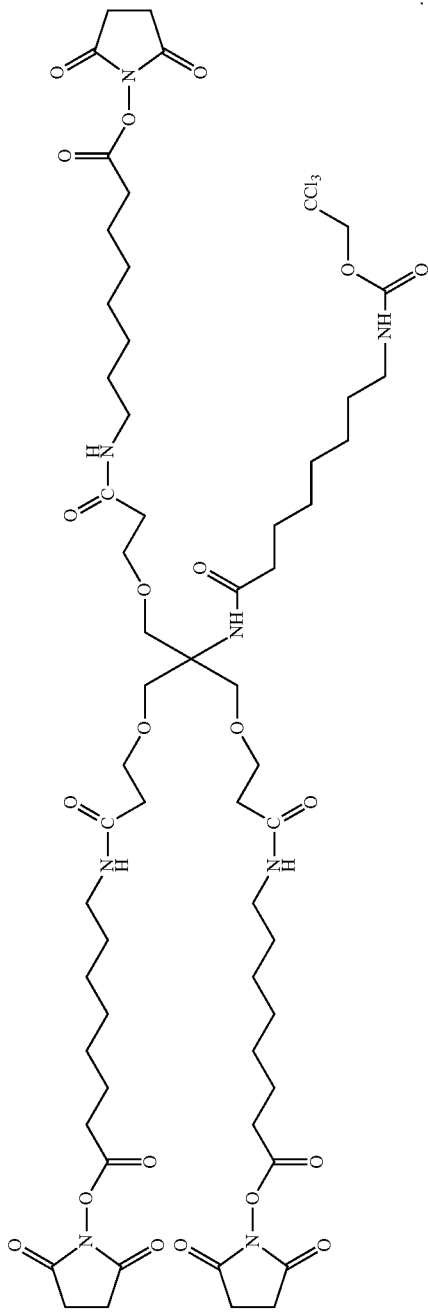

Synthesis of the Compounds of the Invention

The compounds of the invention may be prepared by a variety of different methods. The following are representative non-limiting general methods for synthesising compounds of the invention.

Those skilled in the art will realise that Schemes 2 to 7 below show compounds of the invention where $R^5$ is succinimidyl group. However, compounds of the invention where $R^5$ is other than succinimidyl can be prepared analogously. For example, compounds where $R^5$ is H can be prepared by treatment of the OBn precursors (e.g. Schemes 2-7, below) with palladium on carbon or palladium hydroxide on carbon or platinum on carbon catalysts in solvents such as aqueous THF, methanol, ethanol, ethyl acetate, stirred under a hydrogen atmosphere at ambient temperature and pressure or at 5-50 psi, preferably at 5-25 psi.

"Tetrameric" dendritic core compounds of the invention (where $R^1$ and $R^2$ are both a radical of formula (i) or a radical of formula (ii)) are prepared from compound 1, which is synthesised in three steps from pentaerythritol (Scheme 1).

Scheme 1

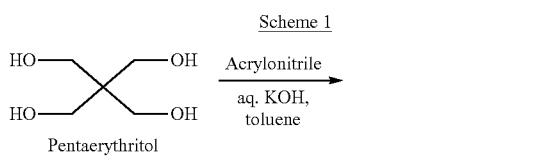

Pentaerythritol

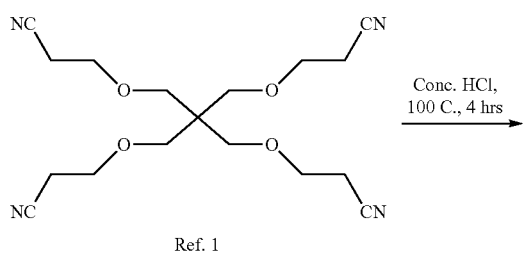

Ref. 1

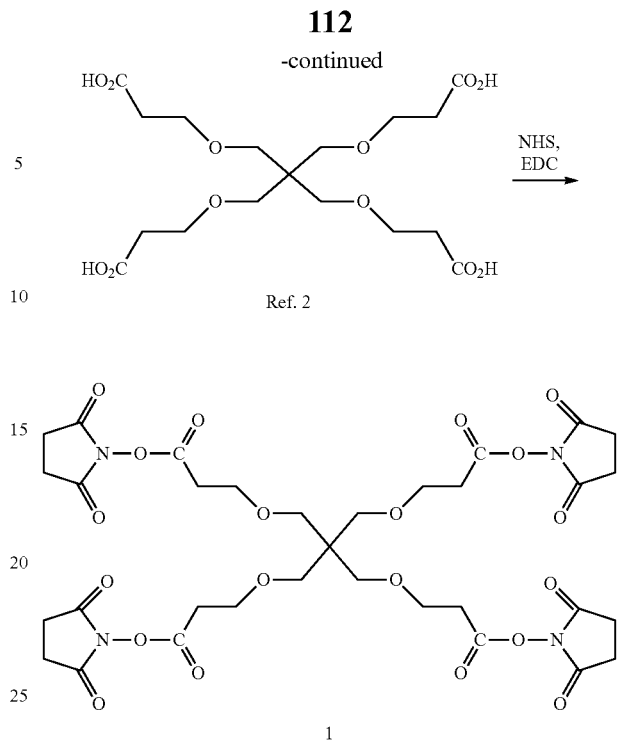

(Ref.1, Hukkämaki, J.; Pakkanen, T. T. *Journal of Molecular Catalysis A: Chemical* 2001, 174, 205-211; Ref. 2, Newcombe, G. R.; Mishra, A; Moorfield, C. N. *J. Org. Chem.* 2002, 67, 3957-3960).

Compound 1 is then converted to compounds of formula (I) via reaction with a suitable amino-substituted carboxylic acid, such as 3-aminopropanoic acid, 4-aminobutanoic acid, 5-aminopentanoic acid, 6-aminohexanoic acid, 7-aminoheptanoic acid, 8-aminooctanoic acid, 9-aminononanoic acid, 10-aminodecanoic acid, 11-aminoundecanoic acid or 12-aminododecanoic acid (Scheme 2).

Scheme 2

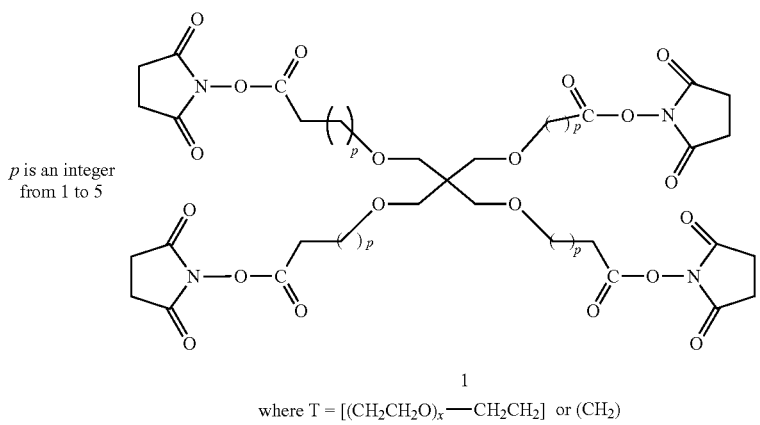

where T = [(CH$_2$CH$_2$O)$_x$—CH$_2$CH$_2$] or (CH$_2$)

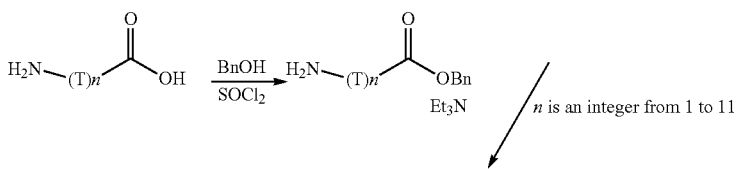

n is an integer from 1 to 11

-continued
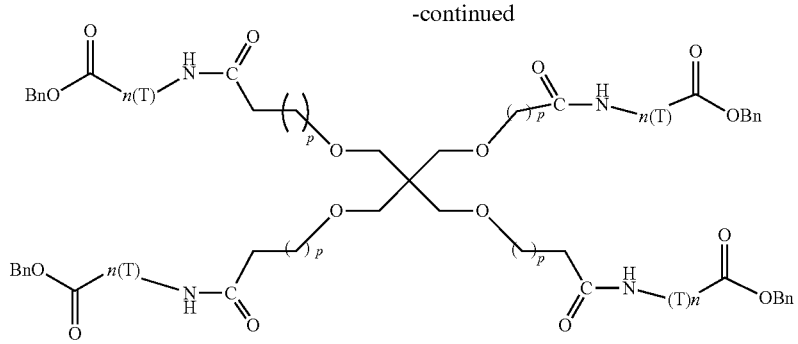
Pd/C/H₂
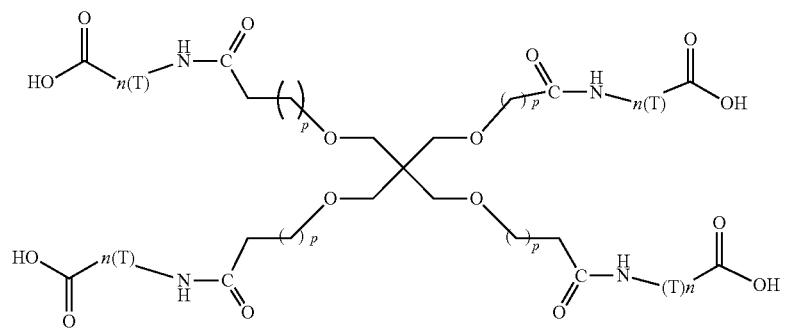
NHS, EDC
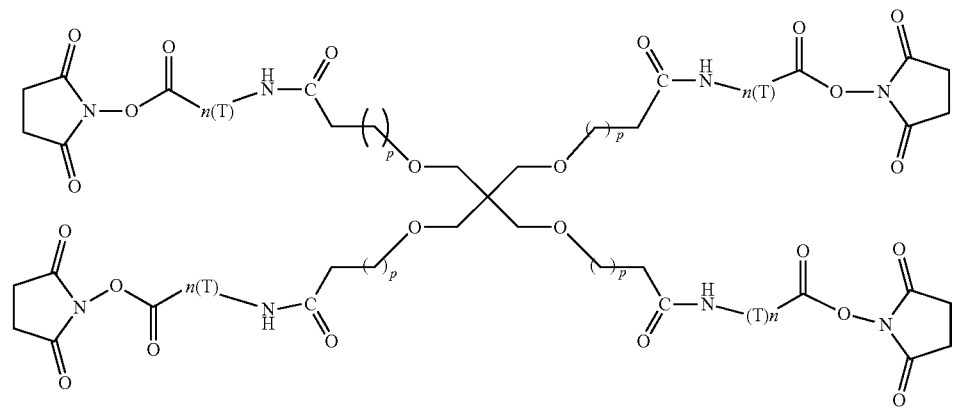
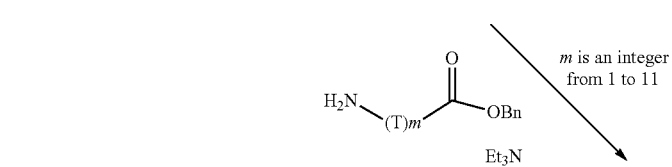
Et₃N
*m* is an integer from 1 to 11

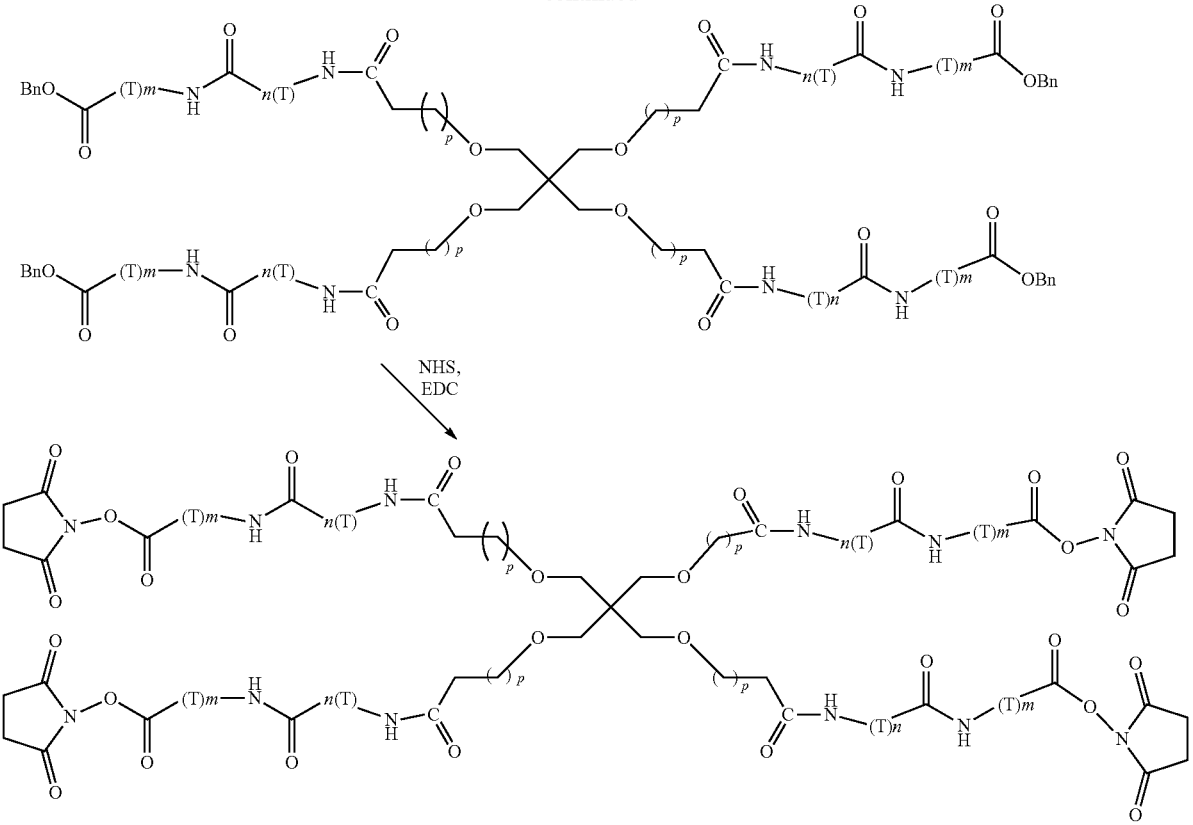

"Dimeric" dendritic core compounds of the invention where Y is C and $R^1$ and $R^2$ are both H are prepared from 3,3'-(propane-1,3-diylbis(oxy)dipropanoic acid, using a suitable amino-substituted carboxylic acid, such as 3-aminopropanoic acid, 4-aminobutanoic acid, 5-aminopentanoic acid, 6-aminohexanoic acid, 7-aminoheptanoic acid, 8-aminooctanoic acid, 9-aminononanoic acid, 10-aminodecanoic acid, 11-aminoundecanoic acid or 12-aminododecanoic acid (Scheme 3).

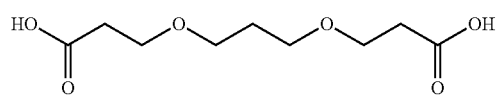

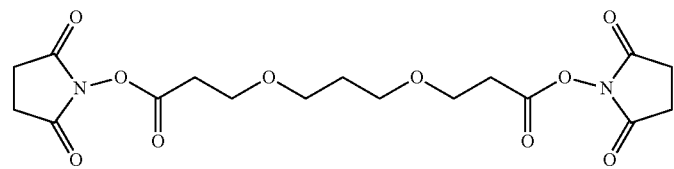

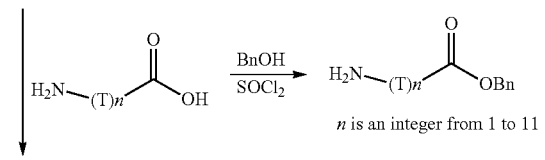

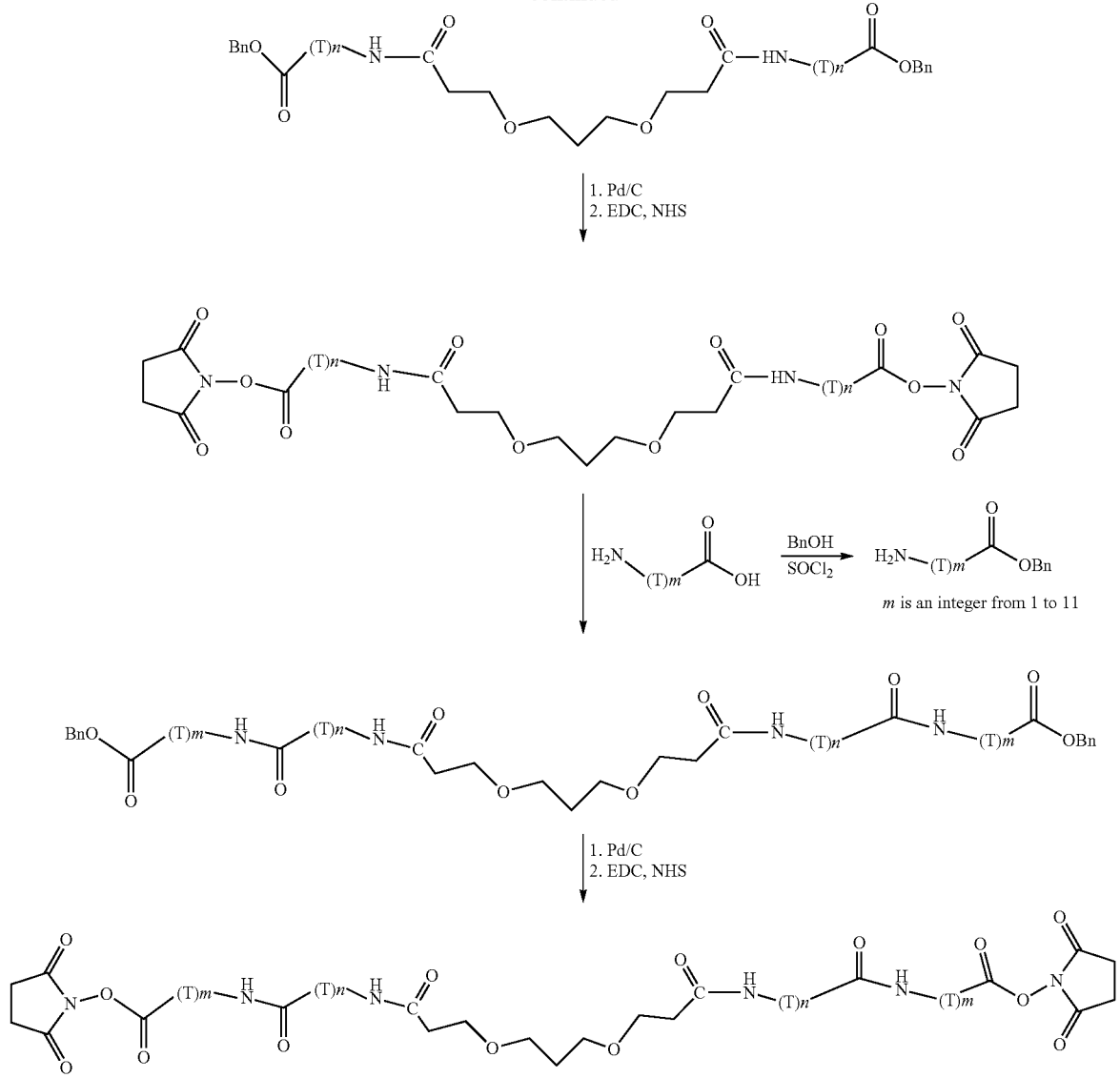
"Dimeric" dendritic core compounds of the invention where Y is C; A is $(CH_2)_u$; and $R^1$ and $R^2$ are both H are prepared from a suitable diacid, as shown in Scheme 4.
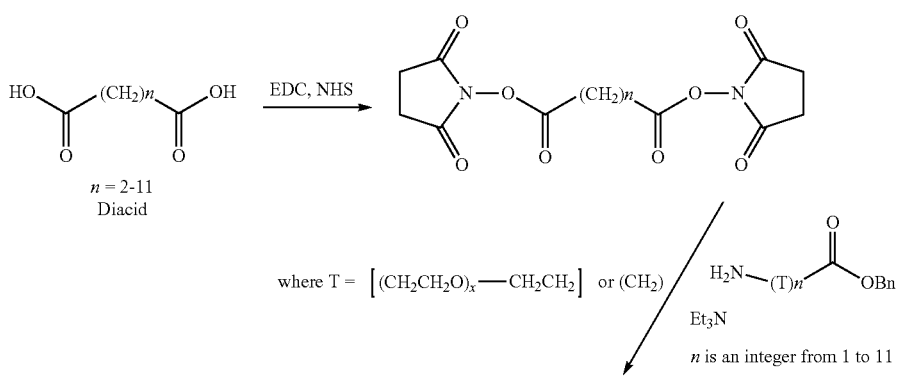

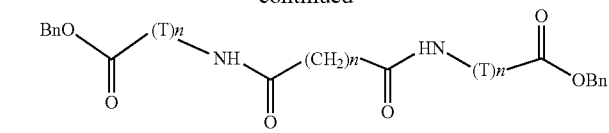
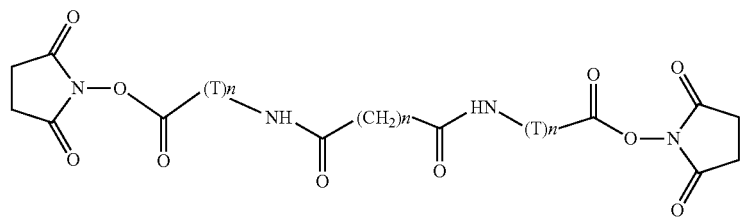
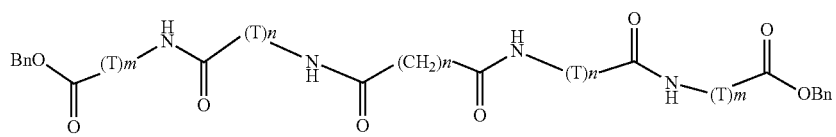
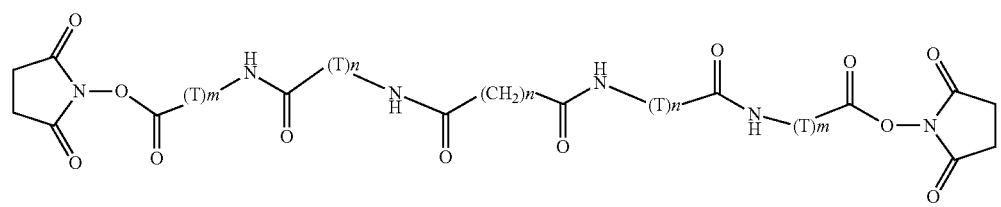
"Dimeric" dendritic core compounds of the invention where Y is O and E is (CH$_2$CH$_2$O)$_x$CH$_2$ are prepared as shown in Scheme 5. Suitable starting materials include, for example, 3,6,9-trioxaundecanedioic acid, 3,6,9,12-tetraoxatetradecanedioic acid or 3,6,9,12,15-pentaoxaheptadecanedioic acid.
Scheme 5
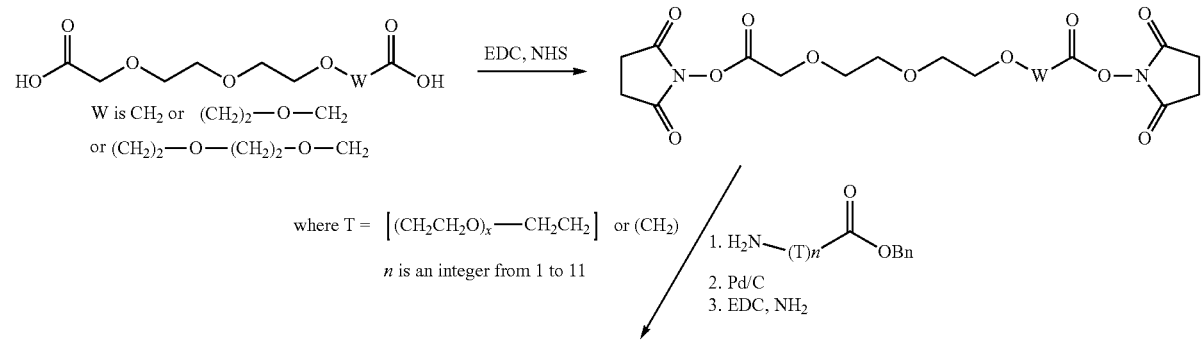

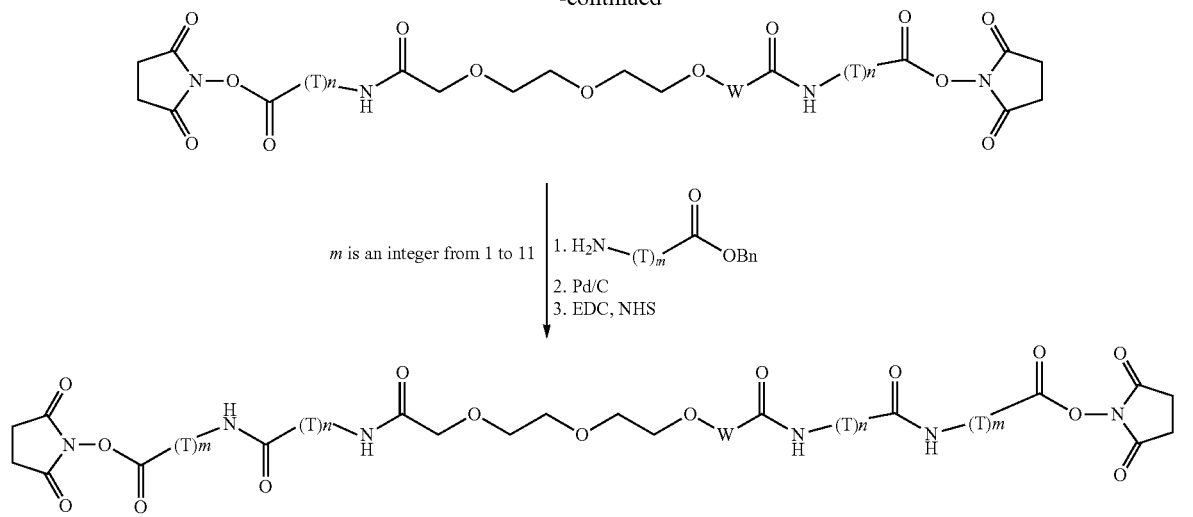

m is an integer from 1 to 11

1. H₂N—(T)ₘ—OBn
2. Pd/C
3. EDC, NHS

"Trimeric" dendritic core compounds of the invention where Y is C and $R^1$ is NHZ are prepared from 2-amino-2-hydroxymethyl-propane-1,3-diol, as shown in Scheme 6. Those skilled in the art will appreciate that trimeric dendritic core compounds where $R^1$ is NH₂ can be used to further elaborate the substitution at the $R^1$ position. For example, such compounds can be linked to radio- or fluorescent labels or the amino functionality can be converted to other functional groups.

Scheme 6

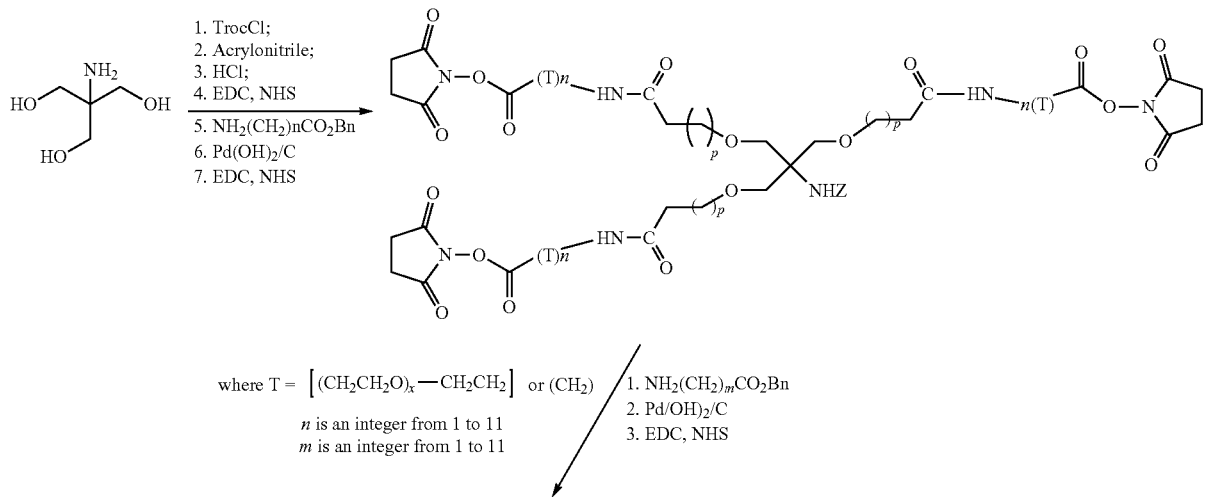

where T = [(CH₂CH₂O)ₓ—CH₂CH₂] or (CH₂)

n is an integer from 1 to 11
m is an integer from 1 to 11

1. TrocCl;
2. Acrylonitrile;
3. HCl;
4. EDC, NHS
5. NH₂(CH₂)nCO₂Bn
6. Pd(OH)₂/C
7. EDC, NHS 1. NH₂(CH₂)ₘCO₂Bn
2. Pd(OH)₂/C
3. EDC, NHS

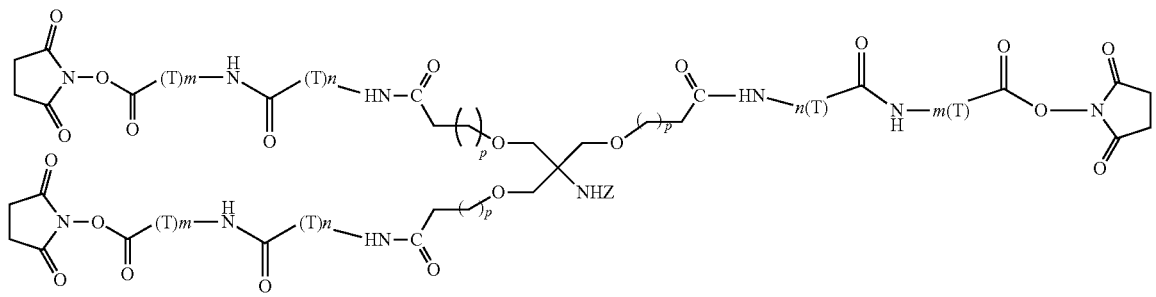

"Trimeric" dendritic core compounds of the invention where Y is C and $R^1$ is H, $CH_3$ or $CH_2CH_3$ are prepared from 2-hydroxymethyl-propane-1,3-diol, 1,1,1-tris(hydroxymethyl)ethane or 1,1,1-tris(hydroxymethyl)propane, respectively (Scheme 7).

2.2 equivalents of glycoside are used for coupling with dimeric compounds of the invention, at least about 3 equivalents of glycoside, e.g. about 3.3 equivalents of glycoside are used for coupling with trimeric compounds of the invention and at least about 4 equivalents of glycoside e.g. about 4.4

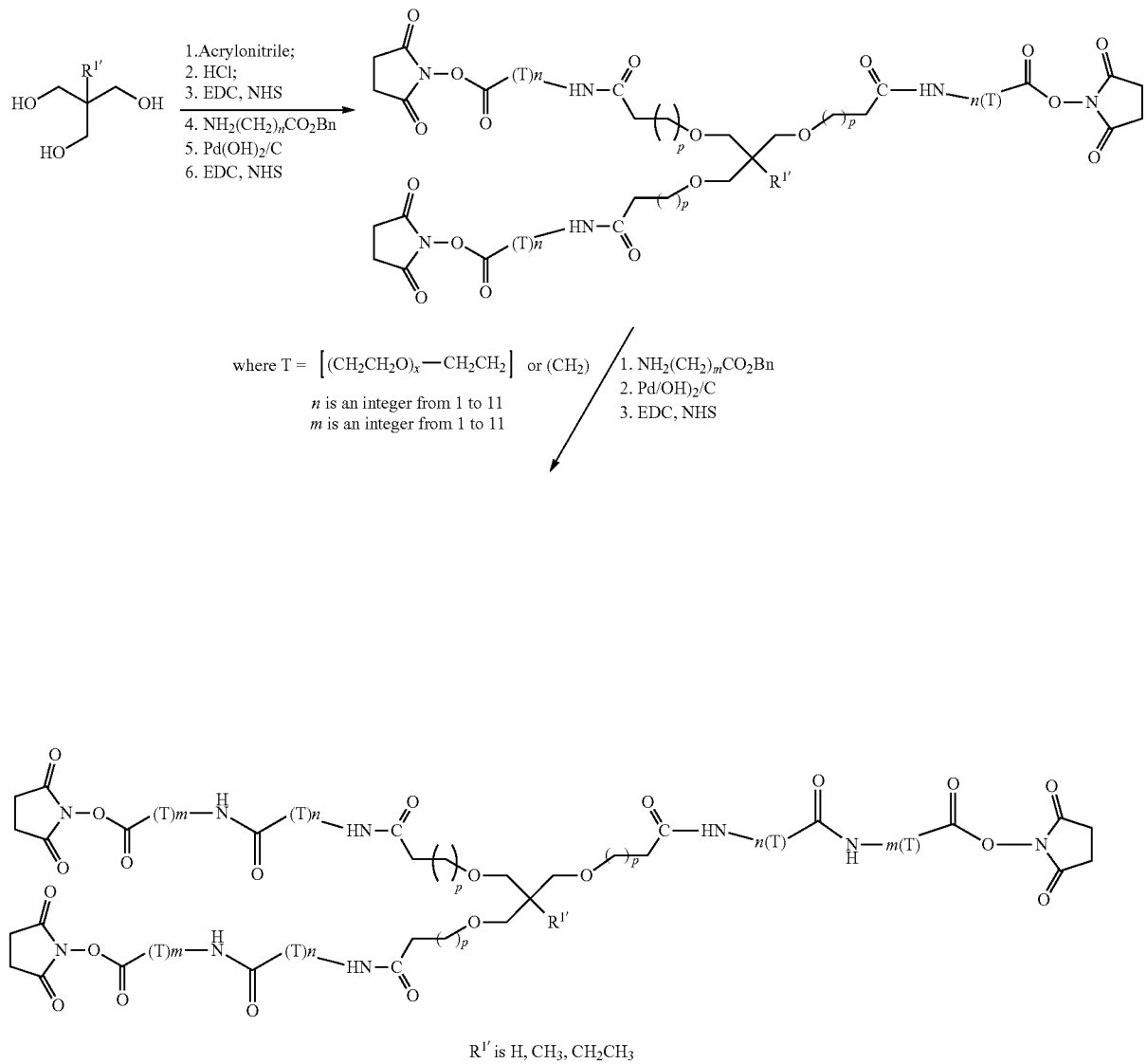

Use of the Compounds of the Invention for Preparing Dendrimers

The compounds of the invention are useful for the preparation of dendritic compounds. Conveniently, the compounds of the invention allow for facile synthesis of dendrimers.

Advantageously, with some compounds of the invention there is no need to use coupling reagents and then to remove an excess of reagents from the dendritic products. The coupling procedure is simple and requires a suitable solvent (DMF, DMSO, water, for example), a small amount of base, e.g. triethylamine, and any glycoside with a free amino group (at least about 2 equivalents of glycoside, e.g. about equivalents of glycoside are used for coupling with tetrameric compounds of the invention).

Using this method, it is possible to attach a variety of carbohydrate fragments (e.g. heparan sulfates, sulfated monosaccharides, oligosaccharides, amino acids, radioligands, imaging agents, fluorescent probes, antibiotics, cytostatic drugs (chemotherapy), veterinary pharmaceuticals, proton and pH sensors, metal ions and ferrocene) with various linkers to the dendritic cores. By way of example, Scheme 8 shows how a "star burst PET-PEG" dendritic cluster glycomimetic of heparan sulfate can be synthesised from a dendritic core of the present invention. This heparan sulfate mimetic is useful as an inhibitor of Alzheimer's β-secretase.

Scheme 8
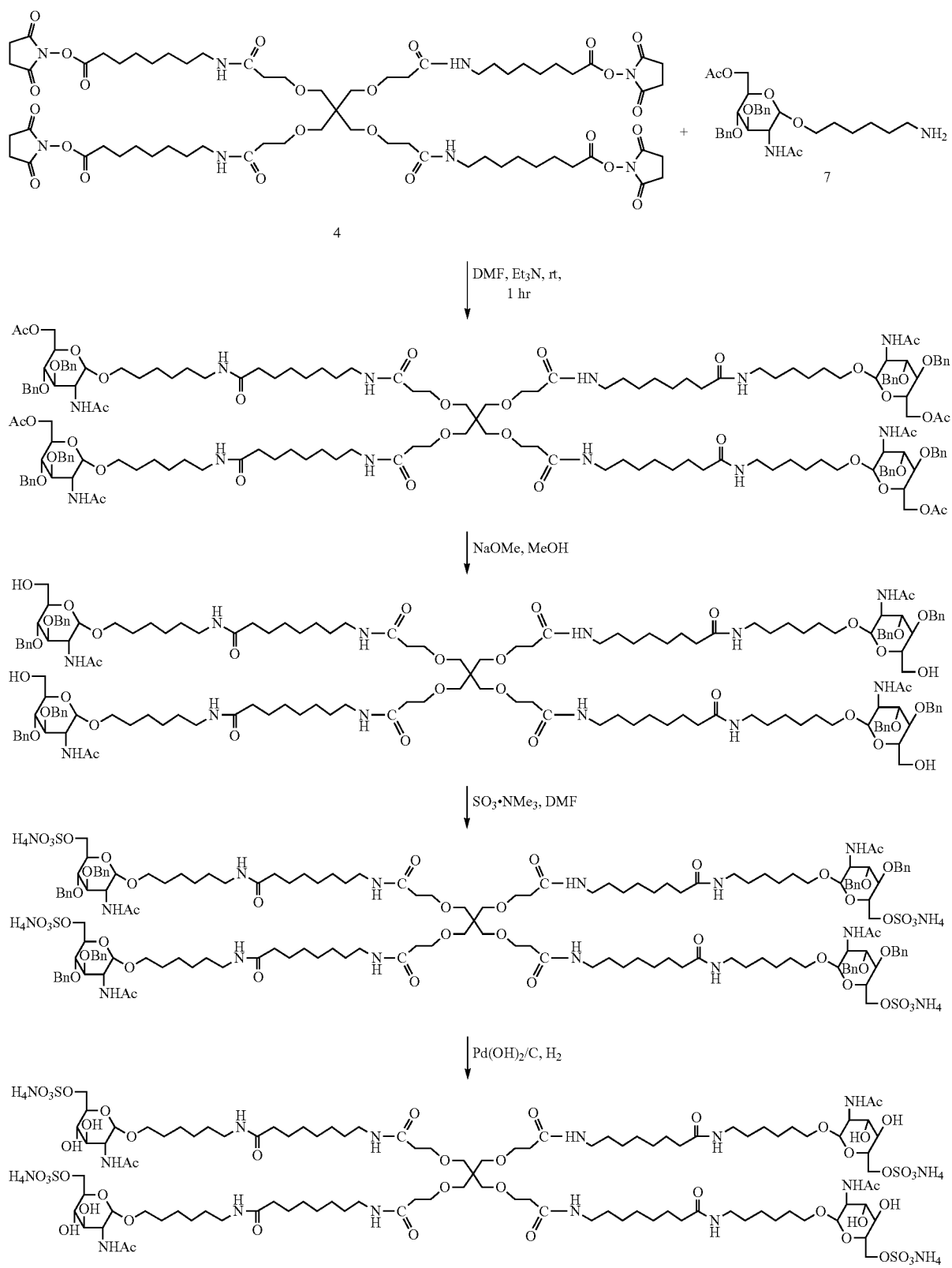
Those skilled in the art will appreciated that, using the tetrameric compounds of the invention, it is possible to achieve dendrimers that are similar size to 16-mer and 32-mer ball-clusters, but which have fewer copies of glycosides attached. Typically, when the use of 16-, 32- and 64-mer dendritic cores is reported, the dendrimer products are described as mixtures with only partial capping of attachment points due to electrostatic repulsion and steric crowding effects. Using the compounds of the invention, with fewer linkers, the glycosides are well separated in space so the capping leads to fully substituted dendrimers. This is advantageous, for example, in the field of pharmaceuticals where it is desirable to produce discrete, well-characterised chemical compounds, rather than mixtures.

ABBREVIATIONS

NMR Nuclear magnetic resonance
HRMS High resolution mass spectrometry
DCM Dichloromethane
DMF N,N-Dimethylformamide
EtOH Ethanol
MeOH Methanol
THF Tetrahydrofuran
EtOAc Ethyl acetate
RT Room temperature
TAMRA 4-Carboxytetramethylrhodamine N-succinimidyl ester
BODIPY 4,4-Difluoro-4-bora-3a,4a-diaza-s-indacene
EDC 1-Ethyl-3-[3-dimethylaminopropyl]carbodiimide hydrochloride
NHS N-Hydroxysuccinimide

EXAMPLES

The following examples further illustrate the invention. It is to be appreciated that the invention is not limited to the examples.

Example 1: Synthesis of Compounds of the Invention

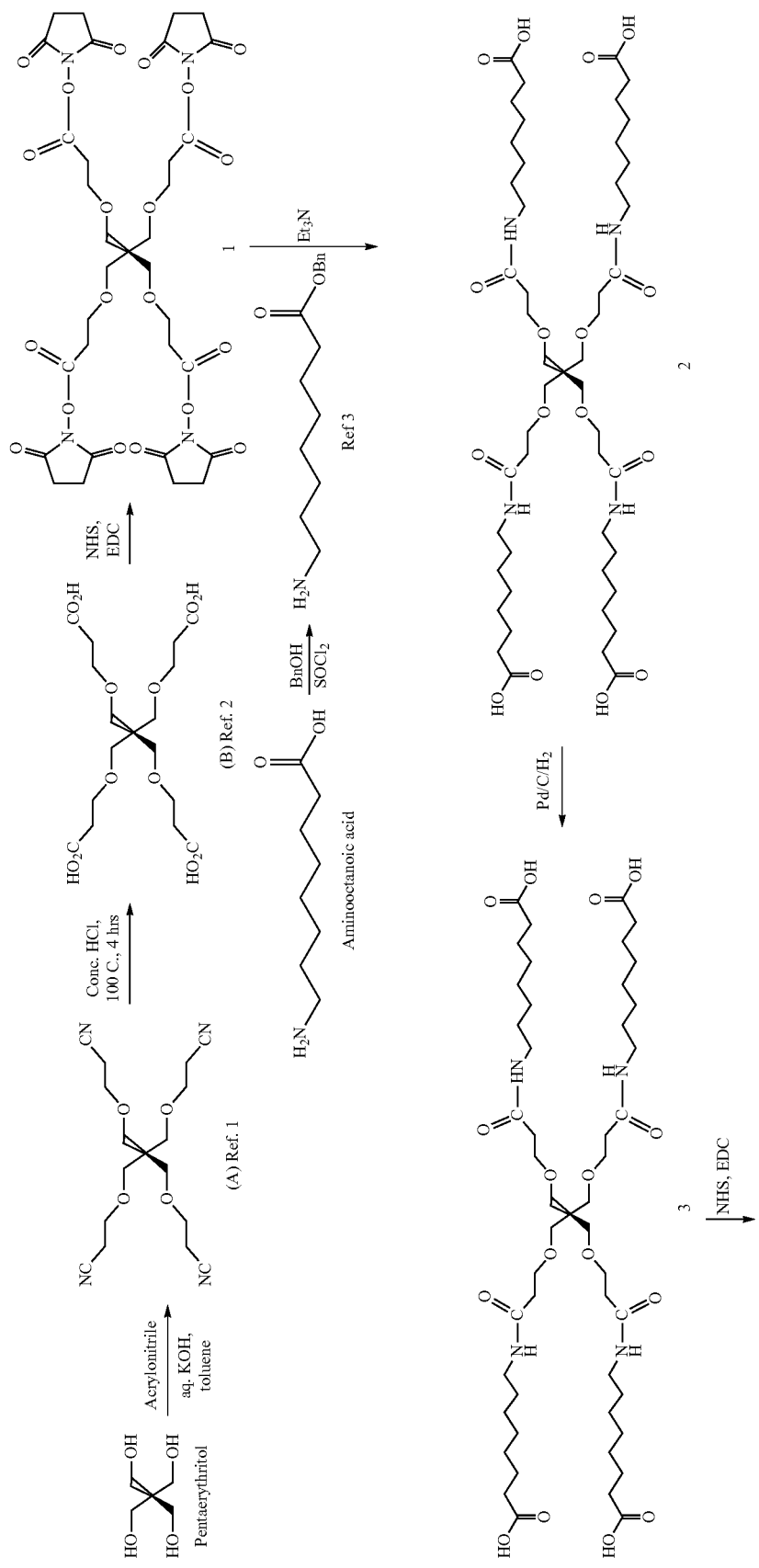

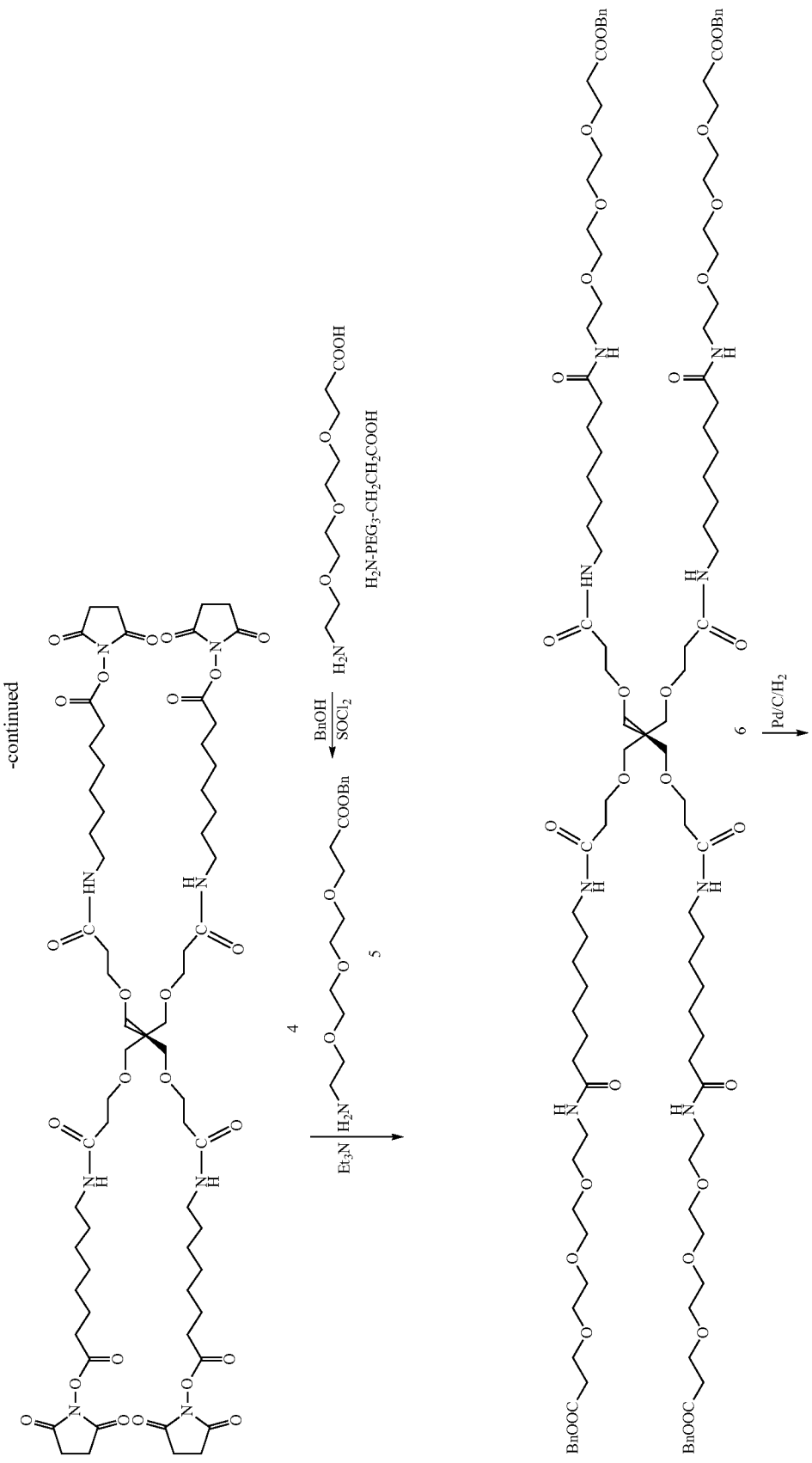

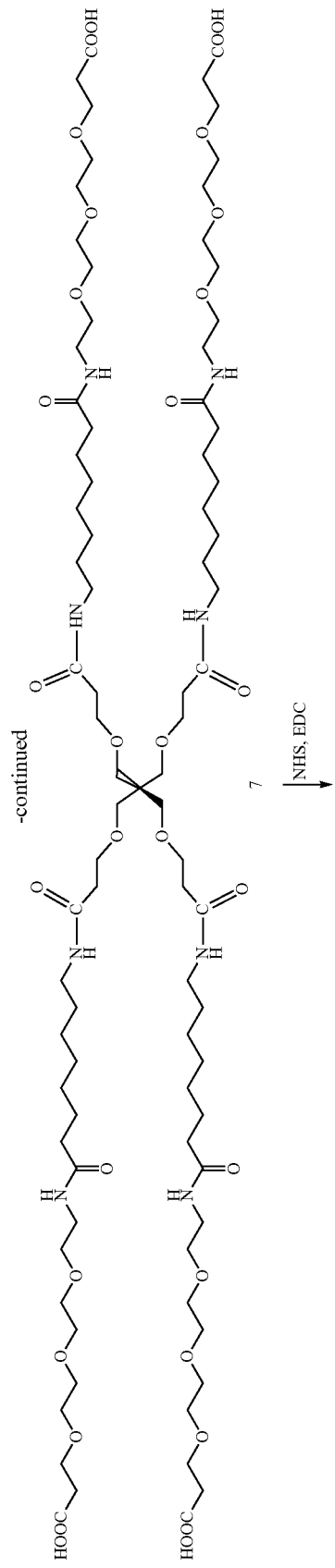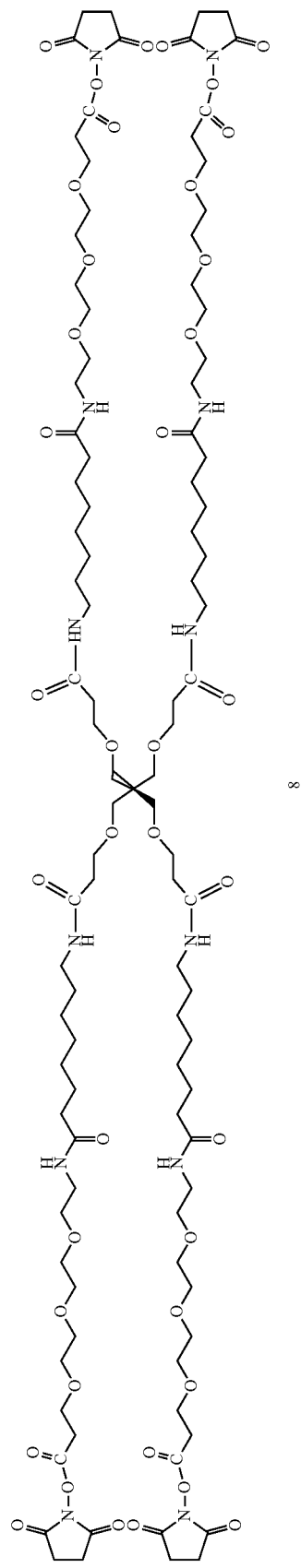

Preparation of 1

Tetranitrile precursor (Ref. 1, Hukkamaki, J.; Pakkanen, T. T. *Journal of Molecular Catalysis A: Chemical* 2001, 174, 205-211) is prepared via Michael-type addition of acrylonitrile to pentaerythritol. Acidic hydrolysis of tetranitrile (Ref. 2, Newcombe, G. R.; Mishra, A; Moorfield, C. N. *J. Org. Chem.* 2002, 67, 3957-3960) furnishes the tetraacid. Tetraacid (1.0 g, 2.35 mmol) is dissolved in dry DMF (15 mL). N-Hydroxysuccinimide (1.62 g, 14.14 mmol) and 1-ethyl-3-[3-dimethylaminopropyl]carbodiimide hydrochloride (EDC, 2.71 g, 14.14 mmol) are added to the reaction mixture at room temperature and stirring continued for 24 hrs. The mixture is diluted with DCM and washed with water, then with diluted HCl and water, dried over magnesium sulfate and concentrated. The residue is purified by flash chromatography on silica gel eluting with EtOAc followed by EtOAc:MeOH, 19:1→9:1→7:1→4:1 to give the tetra-succinimidyl ester (1, 1.2 g, 1.48 mmol, 63%). $R_f$=0.25 (Ethyl Acetate:MeOH, 9:1). $^{13}$C-NMR (125 MHz, DMSO-$D_6$) δ 170.7, 170.1, 68.7, 65.5, 44.9, 31.5, 25.7. HRMS calcd for $C_{33}H_{40}N_4O_{20}Na$ (M+Na)$^+$ m/z 835.2134. found 835.2128.

Preparation of 2

Aminooctanoic acid is treated with benzyl alcohol in the presence of thionyl chloride (Ref. 3, Patel, R. P; Price, S. *J. Org Chem.* 1965, 30 (10), 3575-3576) to give a tetra benzyl ester (2 g, 8.12 mmol). This and tetra-succinimidyl ester (1, 1.1 g, 1.35 mmol) are dissolved in a mixture of dry THF (55 mL) and dry DMF (3 mL) and treated with triethylamine (1.5 mL, 10.83 mmol). After stirring for 24 hrs the mixture is diluted with ethyl acetate and washed with water twice, dried over magnesium sulfate and concentrated. The residue is dissolved in hot EtOAc, the crystals are filtered off and discharged. The mother liquor is concentrated and the residue is purified by flash chromatography on silica gel eluting with Chloroform: EtOAc: MeOH, 5:2:0.5 to afford the tetra-benzyl ester (2, 1.7 g, 1.26 mmol, 93%). $R_f$=0.3 (Chloroform:Ethyl Acetate: MeOH, 5:2:1). $^{13}$C-NMR (125 MHz, CDCl$_3$) δ 173.5, 171.2, 136.1, 128.5, 128.2, 128.1, 69.1, 67.4, 66.1, 45.3, 39.5, 36.9, 34.2, 29.6, 29.4, 28.9, 26.7, 26.6, 24.8. HRMS calcd for $C_{77}H_{112}N_4O_{16}Na$ (M+Na)$^+$ m/z 1371.7971. found 1371.7977.

Preparation of 3

Tetra benzyl ester (2, 0.595 g, 441 µmol) is dissolved in dry THF (16 mL). Water (4 mL) and glacial acetic acid (5 drops) are added. The reaction mixture is treated with palladium hydroxide on carbon (20% Pd, 1 g) and stirred for 3 hours under hydrogen at ambient temperature and pressure. The catalyst is filtered off and washed with 50% aqueous EtOH. The solution is concentrated to dryness to give a "long-armed" tetraacid (3, 0.42 g, 429 µmol, 97%). The product is used in the next step without further purification. $R_f$=0.0 (base line, Chloroform:Ethyl Acetate: MeOH, 5:2:1). $^{13}$C-NMR (125 MHz, DMSO-$D_6$) δ 174.5, 169.9, 68.8, 67.3, 45.0, 39.0, 38.4, 36.1, 33.8, 29.1, 28.5, 38.4, 26.3, 25.2, 24.5. HRMS calcd for $C_{49}H_{87}N_4O_{16}$ (M−H)$^−$ m/z 987.6117. found 987.6110.

Preparation of 4

"Long-armed" tetraacid (3, 424 mg, 429 µmol) is dissolved in dry DMF (7 mL). N-Hydroxysuccinimide (296 mg, 2.57 mmol) and 1-ethyl-3-[3-dimethylaminopropyl]carbodiimide hydrochloride (EDC, 493 mg, 2.57 mmol) are added to the reaction mixture at room temperature and stirring continued for 24 hrs. The mixture is diluted with DCM and washed with water, then with diluted HCl and water, dried over magnesium sulfate and concentrated. The residue is purified by flash chromatography on silica gel eluting with Chloroform:Ethyl Acetate:MeOH, 5:2:0.5→5: 4:1 to give the "long-armed" tetra-succinimidyl ester (4, 415 mg, 301 µmol, 70.3%). $R_f$=0.25 (DCM:MeOH, 9:1). $^{13}$C-NMR (125 MHz, CDCl$_3$) δ 171.5, 169.4, 168.6, 68.9, 67.4, 45.3, 39.4, 36.7, 30.8, 29.5, 29.4, 28.6, 28.5, 26.6, 25.5, 25.4, 24.4. HRMS calcd for $C_{65}H_{100}N_8O_{24}Na$ (M+Na)$^+$ m/z 1399.6748. found 1399.6737.

Preparation of 5

$H_2N(PEG)_3CH_2CH_2COOH$ (or PEG aminoacid) (1.0 g, 4.52 mmol) is dissolved in benzyl alcohol (30 mL, 287 mmol) and cooled to 0° C. Thionyl chloride (6 mL, 82.2 mmol) is added slowly dropwise. The reaction mixture is stirred at 0° C. for 15 min followed by heating at 100° C. for 5 hours. Then this is diluted with diethyl ether and the oily residue is collected and purified by flash chromatography on silica gel eluting with Dichloromethane: MeOH, 9:1→1:1 to afford the benzyl ester (5, 1.2 g, 3.9 mmol, 85%). $R_f$=0.15 (Dichloromethane: MeOH, 9:1). $^{13}$C-NMR (125 MHz, CDCl$_3$) δ 171.6, 135.8, 128.5, 128.2, 128.1, 70.2, 70.14, 70.13, 69.9, 66.7, 66.4, 66.3, 50.0, 39.7, 35.0. HRMS calcd for $C_{1-6}H_{26}NO_5$ (M+H)$^+$ m/z 312.1811. found 312.1806.

Preparation of 6

The benzyl ester 5 (65 mg, 210 µmol) and tetra-succinimidyl ester (4, 58 mg, 42.1 µmol) are dissolved in dry DMF (2 mL) and treated with triethylamine (47 µL, 336 µmol). After stirring for 24 hrs the mixture is diluted with ethyl acetate and washed with water twice, dried over magnesium sulfate and concentrated. The residue is dissolved in hot EtOAc, the crystals are filtered off and discharged. The mother liquor is concentrated and the residue is purified by flash chromatography on silica gel eluting with Chloroform: EtOAc:MeOH, 5:2:0.5 to afford the tetra-benzyl ester (6, 71 mg, 32.8 µmol, 78%). $R_f$=0.3 (Chloroform:Ethyl Acetate: MeOH, 5:2:1). $^{13}$C-NMR (125 MHz, CDCl$_3$) δ 173.2, 171.3, 135.8, 128.5, 128.2, 128.1, 70.5, 704, 70.2, 69.9, 69.2, 67.5, 66.5, 66.3, 45.3, 39.4, 39.1, 36.9, 36.5, 35.1, 29.6, 29.1, 29.0, 26.7, 25.5.

Preparation of 7

Tetra benzyl ester (6, 16 mg, 7.21 µmol) is dissolved in dry THF (4 mL). Water (1 mL) and glacial acetic acid (2 drops) are added. The reaction mixture is treated with palladium hydroxide on carbon (20% Pd, 20 mg) and stirred for 3 hours under hydrogen at ambient temperature and pressure. The catalyst is filtered off and washed with 50% aqueous EtOH. The solution is concentrated to dryness to give a "long-armed" PEG tetraacid (7, 13 mg, 7.21 µmol, 97%). The product is used in the next step without further purification. $R_f$=0.0 (base line, Chloroform:Ethyl Acetate: MeOH, 5:2:1). $^{13}$C-NMR (125 MHz, MeOD) δ 176.7, 174.2, 71.4, 71.3, 71.2, 70.6, 68.8, 67.8, 62.8, 48.5, 40.6, 40.3, 37.8, 37.1, 35.8, 30.4, 30.2, 30.1, 30.0, 27.9, 26.9.

Preparation of 8

"Long-armed" PEG tetraacid (7, 13 mg, 7.21 µmol) is dissolved in dry DMF (1 mL). N-Hydroxysuccinimide (5.1 mg, 43.2 µmol), DIPEA (7.6 µL, 43.2 µmol) and 1-ethyl-3-[3-dimethylaminopropyl]carbodiimide hydrochloride (EDC, 8.3 mg, 43.2 µmol) are added to the reaction mixture at room temperature and stirring continued for 24 hrs. The mixture is diluted with DCM and washed with water, then with diluted HCl and water, dried over magnesium sulfate and concentrated. The residue is purified by flash chromatography on silica gel eluting with Chloroform:Ethyl Acetate: MeOH, 5:2:0.5→5:4:1 to give the "long-armed" PEG tetra-succinimidyl ester (8, 15 mg, 6.85 µmol, 94%). $R_f$=0.25 (DCM:MeOH, 9:1).

Scheme 10
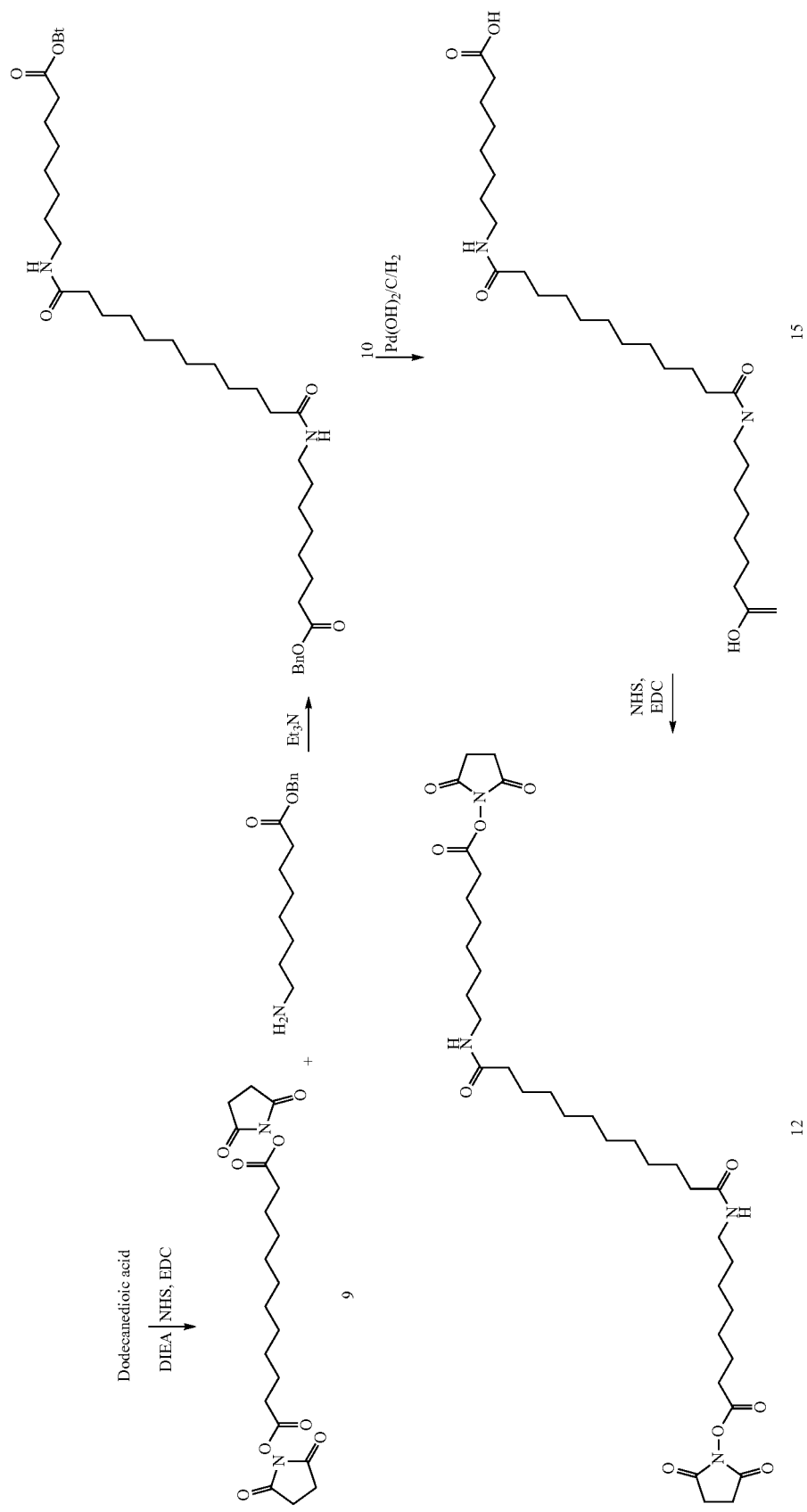

Preparation of 9

Dodecanedioic acid (1.0 g, 4.34 mmol) is dissolved in dry DMF (10 mL). N-Hydroxysuccinimide (1.51 g, 13.0 mmol, 3 eq.) and 1-ethyl-3-[3-dimethylaminopropyl]carbodiimide hydrochloride (EDC, 2.55 g, 13.0 mmol, 3 eq.) and N,N-diisopropylethylamine (1.53 mL, 8.68 mmol) are added to the reaction mixture at room temperature and stirring continued for 24 hrs. The mixture is diluted with DCM and washed with water, then with diluted HCl and water, dried over magnesium sulfate and concentrated. The residue is re-crystalized from hot EtOAc to give the di-succinimidyl ester (9, 1.84 g, 4.2 mmol, 98%). $^{13}$C-NMR (125 MHz, DMSO-D$_6$) δ 170.2, 168.9, 30.2, 28.7, 28.4, 27.9, 25.4, 24.2. HRMS calcd for $C_{20}H_{28}N_2O_8Na$ (M+Na)$^+$ m/z 447.1743. found 447.1743.

Preparation of 10

Di-succinimidyl ester (9, 500 mg, 1.18 mmol) and an amino benzyl ester (881 mg, 3.53 mmol, 3 eq.) are dissolved in dry DMF (8 mL) and treated with triethylamine (0.66 mL, 4.71 mmol, 4 eq.). After stirring for 24 hrs the mixture is concentrated. The residue is dissolved in hot MeOH, a few drop of chloroform added, the crystals are filtered off and dried to afford the di-benzyl ester (10, 0.75 g, 1.1 mmol, 92%). $^{13}$C-NMR (125 MHz, MeOD) δ 176.2, 175.5, 137.4, 129.8, 129.4, 129.4, 67.5, 40.6, 37.6, 35.5, 30.7, 30.6, 30.5, 30.2, 30.1, 27.9, 27.2, 26.1. HRMS calcd for $C_{42}H_{64}N_2O_6Na$ (M+Na)$^+$ m/z 715.4662. found 715.4664.

Scheme 11
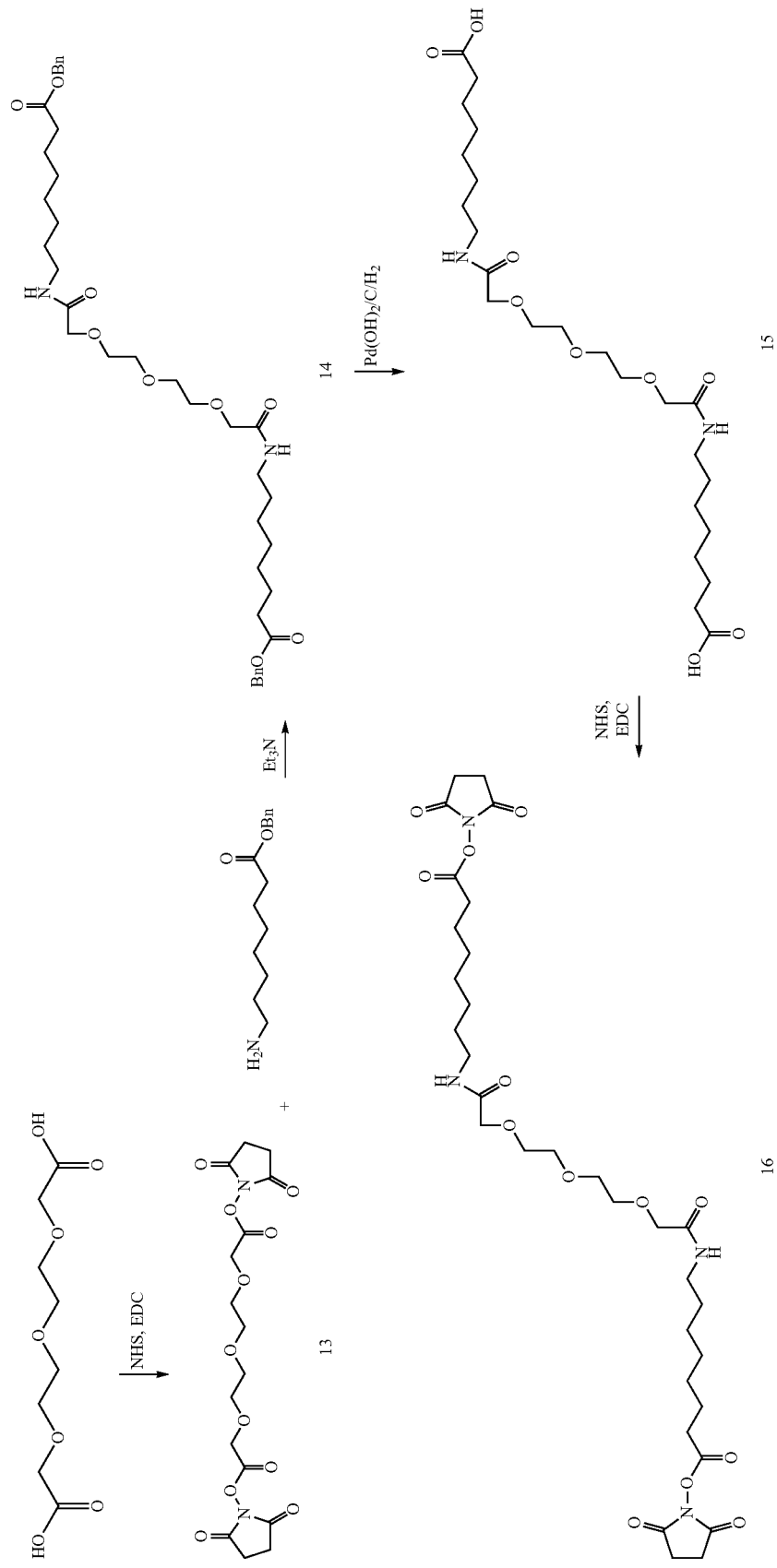

Preparation of 14

3,6,9-Trioxaundecanedioic acid (500 mg, 2.25 mmol) is dissolved in dry DMF (10 mL). N-Hydroxysuccinimide (785 mg, 6.75 mmol, 3 eq.), 1-ethyl-3-[3-dimethylaminopropyl]carbodiimide hydrochloride (EDC, 1.32 g, 6.75 mmol, 3 eq.) and N,N-diisopropylethylamine (2.38 mL, 13.5 mmol) followed by benzyl 8-aminooctanate (1.68 g, 6.75 mmol, 3 eq.) are added to the reaction mixture at room temperature and stirring continued for 4 hrs. The mixture is diluted with DCM and washed with water, then with diluted HCl and water, dried over magnesium sulfate and concentrated. The residue is dissolved in hot EtOAc, the crystals are filtered off and discharged. The mother liquor is concentrated and the residue is purified by flash chromatography on silica gel eluting with Chloroform: EtOAc: MeOH, 5:2:0.3 to afford the di-benzyl ester (14, 1.1 g, 1.61 mmol, 71%). $^{13}$C-NMR (125 MHz, CDCl$_3$) δ 173.4, 169.9, 136.1, 128.4, 128.3, 128.1, 127.8, 127.7, 65.9, 63.9, 60.3, 39.5, 36.8, 31.9, 30.9, 29.3, 28.8, 26.6, 25.3, 24.7, 24.4, 21.2, 20.9. HRMS calcd for C$_{38}$H$_{56}$N$_2$O$_9$Na (M+Na)$^+$ m/z 707.3884. found 707.3876.

Preparation of 15

Di-benzyl ester (14, 204 mg, 297 μmol) is dissolved in dry THF (8 mL). Water (2 mL) and glacial acetic acid (3 drops) are added. The reaction mixture is treated with palladium hydroxide on carbon (20% Pd, 0.5 g) and stirred for 3 hours under hydrogen at ambient temperature and pressure. The catalyst is filtered off and washed with 50% aqueous EtOH. The solution is concentrated to dryness to give a "long-armed" diacid (15, 150 mg, 297 μmol, 99.8%). The product is used in the next step without further purification. R$_f$=0.0 (base line, Chloroform:Ethyl Acetate: MeOH, 5:2:1). $^{13}$C-NMR (125 MHz, MeOD) δ 178.1, 175.3, 172.9, 72.3, 71.7, 71.6, 40.4, 35.5, 30.9, 30.6, 30.5, 28.3, 26.5. HRMS calcd for C$_{24}$H$_{44}$N$_2$O$_9$Na (M+Na)$^+$ m/z 527.2945. found 527.2943.

Preparation of 16

"Long-armed" diacid (15, 150 mg, 297 μmol) is dissolved in dry DMF (4 mL). N-Hydroxysuccinimide (104 mg, 892 μmol), 1-ethyl-3-[3-dimethylaminopropyl]carbodiimide hydrochloride (EDC, 174 mg, 892 μmol) and N,N-diisopropylethylamine (0.157 mL, 892 μmol) are added to the reaction mixture at room temperature and stirring continued for 24 hrs. The mixture is diluted with DCM and washed with water, then with diluted HCl and water, dried over magnesium sulfate and concentrated. The residue is purified by flash chromatography on silica gel eluting with Chloroform:Ethyl Acetate: MeOH, 5:2:0.5→5:4:1 to give the "long-armed" di-succinimidyl ester (16, 188 mg, 269 μmol, 90%). R$_f$=0.25 (DCM:MeOH, 9:1). $^{13}$C-NMR (125 MHz, CDCl$_3$) δ 170.9, 169.9, 169.5, 168.5, 70.7, 70.6, 70.5, 70.4, 70.0, 38.7, 31.4, 30.7, 29.4, 28.6, 28.5, 28.4, 26.5, 25.5, 24.4. HRMS calcd for C$_{32}$H$_{50}$N$_4$O$_{13}$Na (M+Na)$^+$ m/z 721.3272. found 721.3259.

Although the invention has been described by way of example, it should be appreciated that variations and modifications may be made without departing from the scope of the invention. Furthermore, where known equivalents exist to specific features, such equivalents are incorporated as if specifically referred to in the specification.

INDUSTRIAL APPLICABILITY

The invention relates to compounds that are useful for the preparation of dendrimer compounds, the use of these compounds for preparing dendrimers and processes for preparing the compounds.

The invention claimed is:
1. A compound of formula (I)

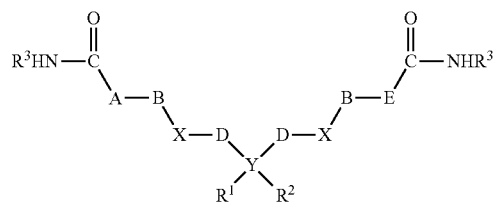

wherein:
Y is O;
B is O;
R$^1$ and R$^2$ are absent; and
either A, E, D and X are all CH$_2$; or A, D and X are all CH$_2$ and E is (CH$_2$CH$_2$O)$_t$$^\#$CH$_2$;
wherein $^\#$ indicates a point of attachment of E to its adjacent carbonyl group;
t is an integer from 1 to 10;
or wherein:
Y is C;
R$^1$ and R$^2$ are both H; and
A, E, B and D are CH$_2$ and X is O;
or wherein:
Y is C;
X is O;
B is (CH$_2$)$_p$;
A, E and D are all CH$_2$; and
R$^1$ is H, NHZ or C$_{1-6}$alkyl and R$^2$ is a radical of formula (i) or a radical of formula (ii)

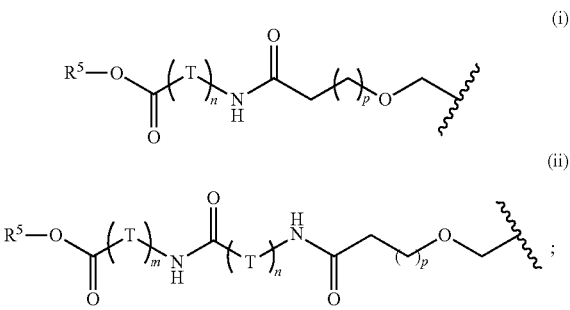

Z is H, acyl, C(O)(CH$_2$)$_w$N(H)G, *CH$_3$*C(O)— where *C denotes $^{13}$C or $^{14}$C, 4-carboxytetramethylrhodamine, resorcinolphthalein, 7-amino-4-methyl-6-sulfocoumarin-3-acetic acid, 4,4-difluoro-4-bora-3a,4a-diaza-s-indacene or 1-{3-{[4-(2-cyclooctyn-1-ylmethyl)benzoyl]amino}propyl}-4-{2-[4-(dimethylamino)phenyl]ethenyl}pyridinium hexafluorophosphate;
w is an integer from 1 to 11;
G is H, acyl, t-butoxycarbonyl, 2,2,2-trichloroethyloxycarbonyl, 9-fluorenylmethoxycarbonyl, benzyloxycarbonyl,*CH$_3$*CO— where *C denotes $^{13}$C or $^{14}$C, 4-carboxytetramethylrhodamine, resorcinolphthalein, 7-amino-4-methyl-6-sulfocoumarin-3-acetic acid, 4,4-difluoro-4-bora-3a,4a-diaza-s-indacene or 1-{3-{[4-(2-cyclooctyn-1-ylmethyl)benzoyl]amino}propyl}-4-{2-[4-(dimethylamino)phenyl]ethenyl}pyridinium hexafluorophosphate;

or wherein:
Y is C;
X is O;
B is (CH$_2$)$_p$;
A, E and D are all CH$_2$; and
R$^1$ and R$^2$, both the same, are a radical of formula (i) or a radical of formula (ii)

(i)
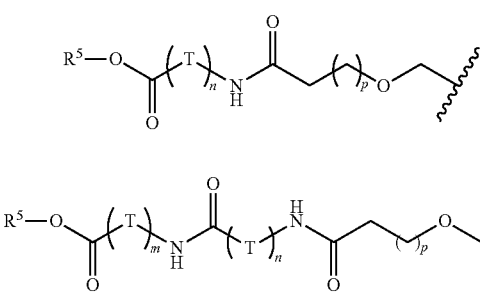

(ii)

R$^3$ is a radical of formula (iii) or a radical of formula (iv)

(iii)
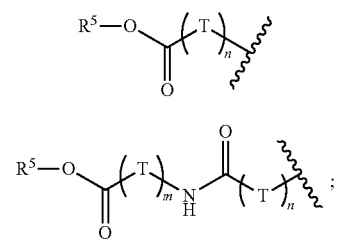

(iv)

each T is independently selected from the group consisting of (CH$_2$CH$_2$O)$_x$(CH$_2$CH$_2$ and CH$_2$;
each x is independently an integer from 1 to 12;
m is an integer from 1 to 11, provided that when T is (CH$_2$CH$_2$O)$_x$CH$_2$CH$_2$ then m is 1;
n is an integer from 1 to 11, provided that when T is (CH$_2$CH$_2$O)$_x$CH$_2$CH$_2$ then n is 1;
p is an integer from 1 to 5;
R$^5$ is H,

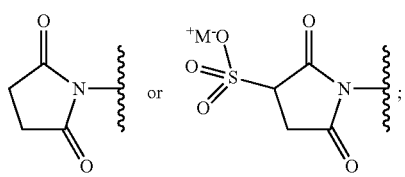

and

M is sodium or ammonium.

2. The compound of claim 1 wherein each T is CH$_2$.

3. The compound of claim 1 wherein at least one T is (CH$_2$CH$_2$O)$_x$CH$_2$CH$_2$.

4. The compound of claim 1, wherein Y is C.

5. The compound of claim 1, wherein R$^3$ is a radical of formula (iii).

(iii)
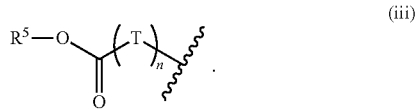

6. The compound of claim 1, wherein R$^3$ is a radical of formula (iv)

(iv)
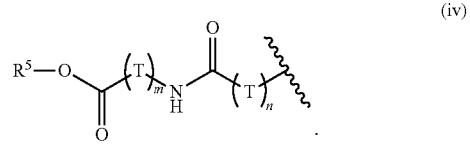

7. The compound of claim 1, wherein R$^1$ and R$^2$ are both a radical of formula (i)

(i)
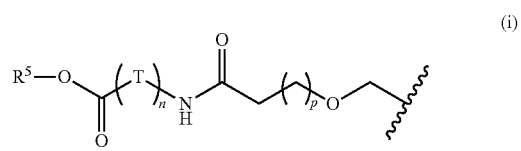

or are both a radical of formula (ii)

(ii)
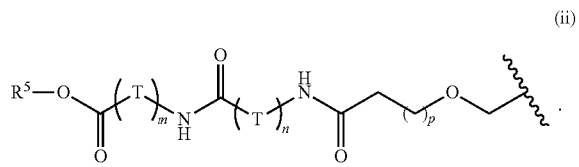

8. The compound of claim 1, herein R$^5$ is

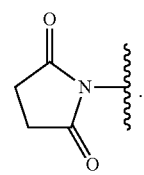 [SMILES: *N1C(=O)CCC1=O]

9. The compound of claim 1, wherein Y is C; R$^1$ and R$^2$ are both H; A, E, B and D are CH$_2$ and X is O.

10. The compound of claim 1, wherein:
Y is C; X is O; A, E and D are all CH$_2$; B is (CH$_2$)$_p$;
R$^1$ is NHZ or C$_{1-6}$alkyl;
R$^2$ is a radical of formula (i) or a radical of formula (ii)

(i)
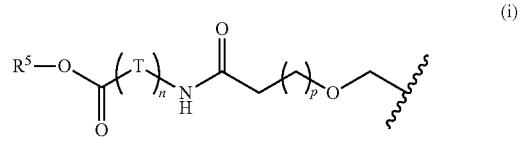

-continued

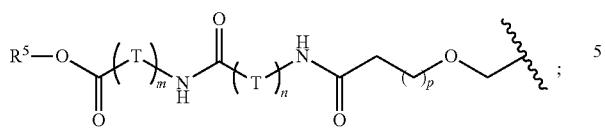
(ii)

Z is H, acyl, C(O)(CH$_2$)$_w$NHG, *CH$_3$*C(O)— where *C denotes $^{13}$C or $^{14}$C, 4-carboxytetramethylrhodamine; resorcinolphthalein, 7-amino-4-methyl-6-sulfocoumarin-3-acetic acid, 4,4-difluoro-4-bora-3a,4a-diaza-s-indacene or 1-{3-{[4-(2-cyclooctyn-1-ylmethyl)benzoyl]amino}propyl}-4-{2-[4-(dimethylamino)phenyl]ethenyl}pyridinium hexafluorophosphate;

w is an integer from 1 to 11; and

G is H, acyl, t-butoxycarbony 2,2,2-trichloroethyloxycarbonyl, 9-fluorenylmethoxycarbonyl, benzyloxycarbonyl, *CH$_3$*CO— where *C denotes $^{13}$C or $^{14}$C, 4-carboxytetramethylrhodamine, resorcinolphthalein; 7-amino-4-methyl-6-sulfocoumarin-3-acetic acid, 4,4-difluoro-4-bora-3a,4a-diaza-s-indacene or 1-{3-{[4-(2-cyclooctyn-1-ylmethyl)benzoyl]amino}propyl}-4-{2-[4-(dimethylamino)phenyl]ethenyl}pyridinium hexafluorophosphate.

11. The compound of claim 1, wherein Y is C; X is O; A, E and D are all CH$_2$; B is (CH$_2$)$_p$; R$^1$ and R$^2$, both the same, are a radical of formula (i)

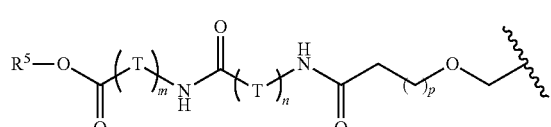
(i)

R$^3$ is a radical of formula (iii)

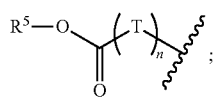
(iii)

and p is 1.

12. The compound of claim 1, wherein Y is C; Y is O; A, E and D are all CH$_2$; B is (CH$_2$)$_p$; R$^1$ and R$^2$, both the same, are a radical of formula (ii)

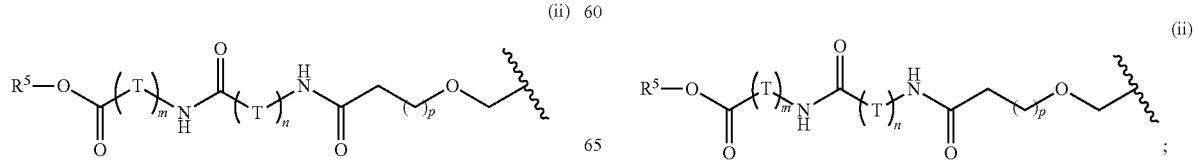
(ii)

and R$^3$ is a radical of formula (iv)

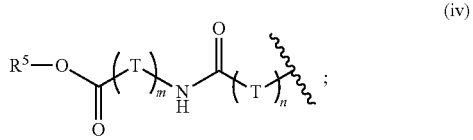
(iv)

and p is 1.

13. The compound of claim 1, wherein Y is C; R$^1$ and R$^2$ are both H; A, E, B and D are CH$_2$; X is O; and R$^3$ is a radical of formula (iii)

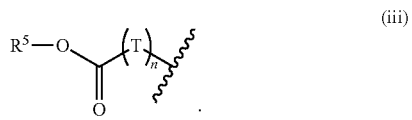
(iii)

14. The compound of claim 1, wherein Y is C; R$^1$ and R$^2$ are both H; A, E, B and D are CH$_2$; X is O; and R$^3$ is a radical of formula (iv)

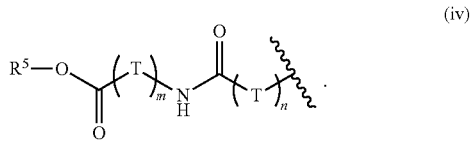
(iv)

15. The compound of claim 1, wherein Y is C; Y is O; A, E and D are all CH$_2$; B is (CH$_2$)$_p$; R$^1$ is H; R$^2$ is a radical of formula (i)

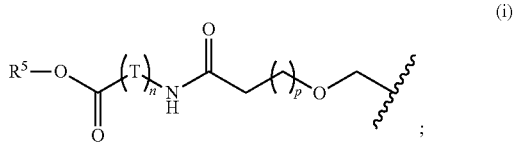
(i)

R$^3$ is a radical of formula (iii)

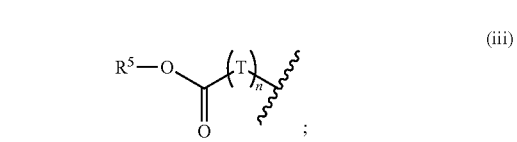
(iii)

and p is 1.

16. The compound of claim 1, wherein Y is C; X is O; E and D are all CH$_2$; B is (CH$_2$)$_p$; R$^1$ is H; R$^2$ is a radical of formula (ii)

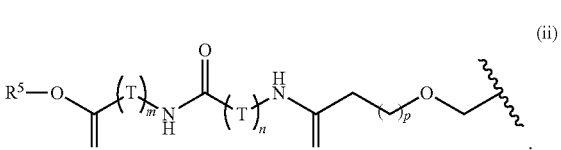
(ii)

$R^3$ is a radical of formula (iv)

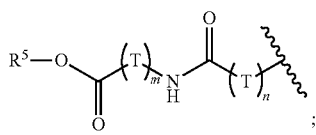
(iv)

and p is 1.

17. The compound of claim 1, wherein Y is C; X is O; A, E and D are all $CH_2$; B is $(CH_2)_p$; $R^1$ is H; $R^2$ is a radical of formula (ii)

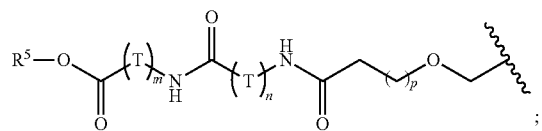
(ii)

$R^3$ is a radical of formula (iii)

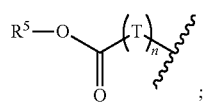
(iii)

and p is 1.

18. The compound of claim 1; wherein Y is C; X is O; A, E and D are all $CH_2$; B is $(CH_2)_p$; $R^1$ is H; $R^2$ is a radical of formula (i)

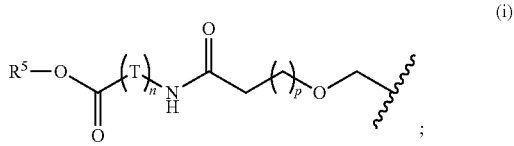
(i)

$R^3$ is a radical of formula (iv)

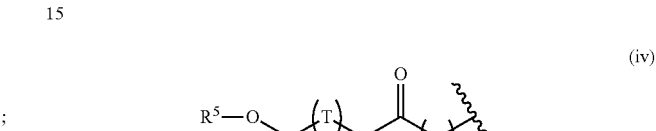
(iv)

and p is 1.

19. The compound of claim 1, when the co mound is selected from the group consisting of:

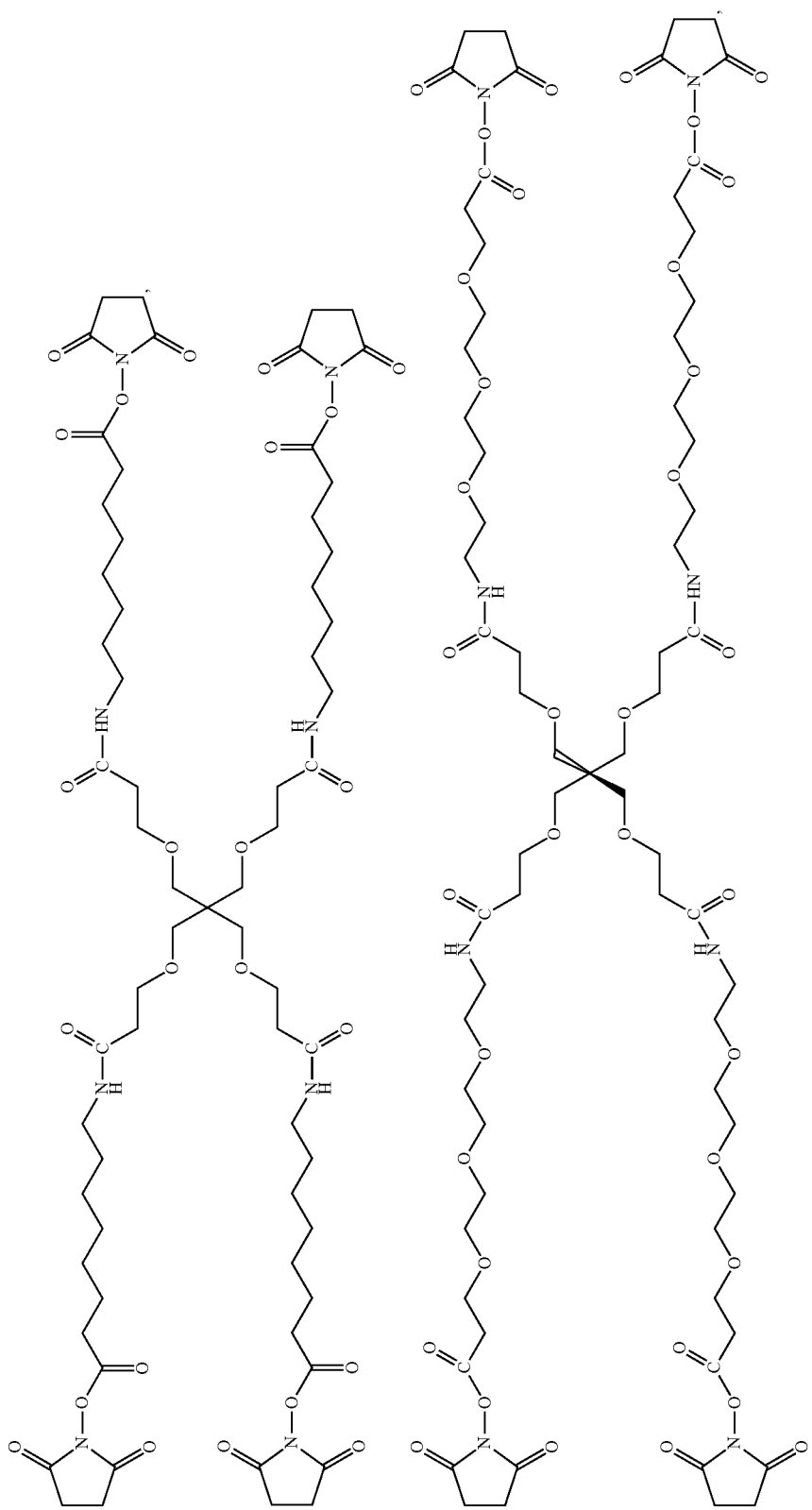

153 154
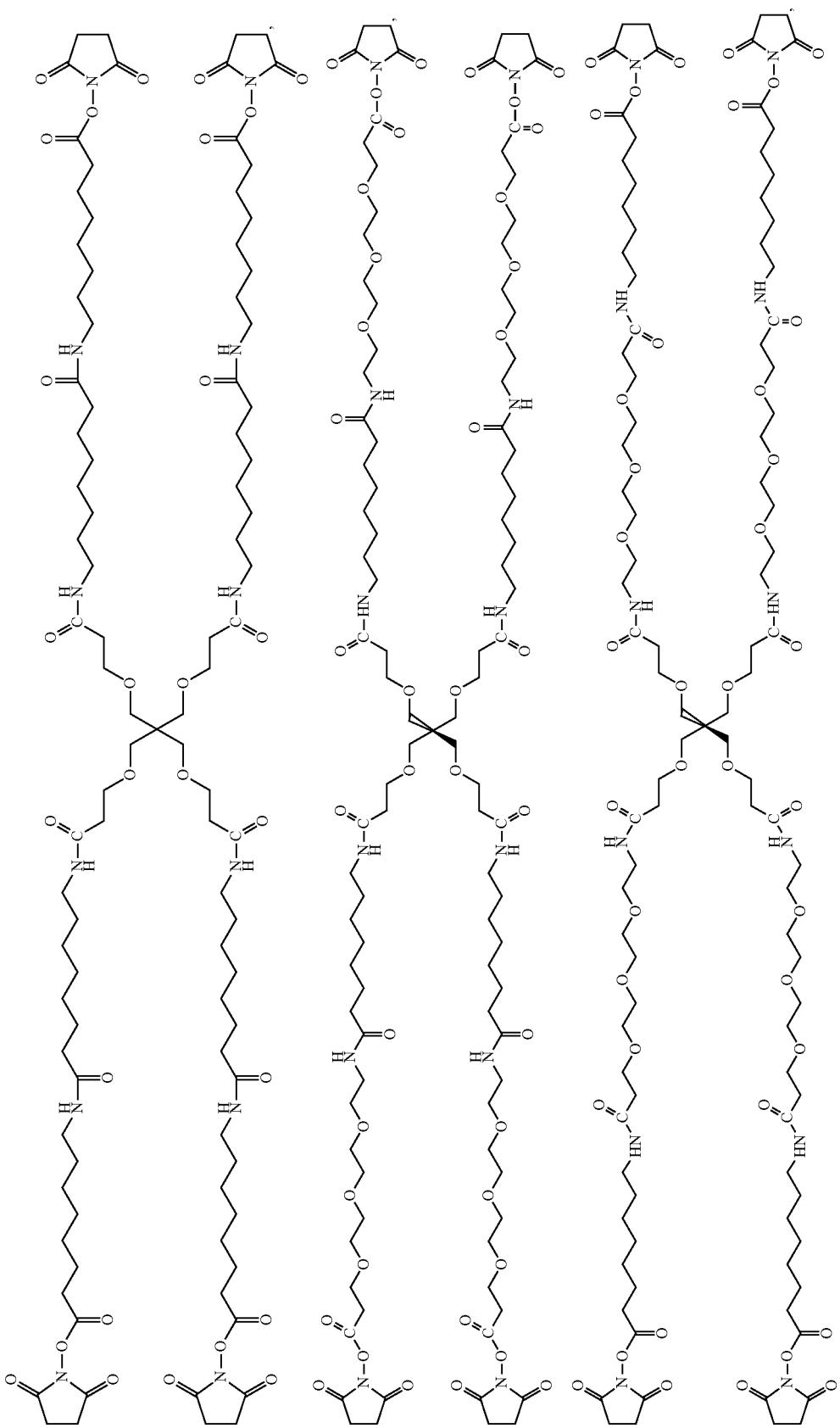

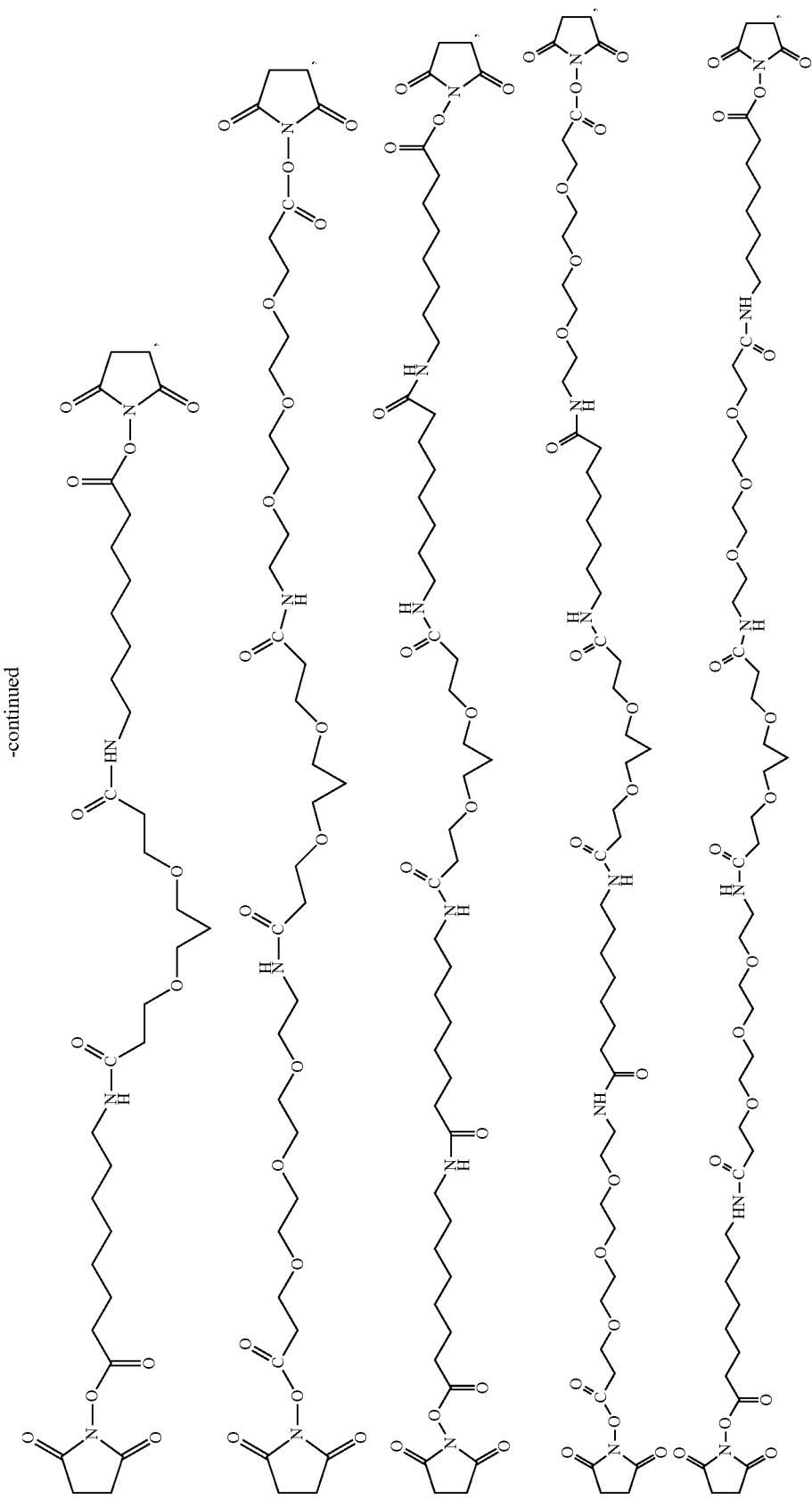

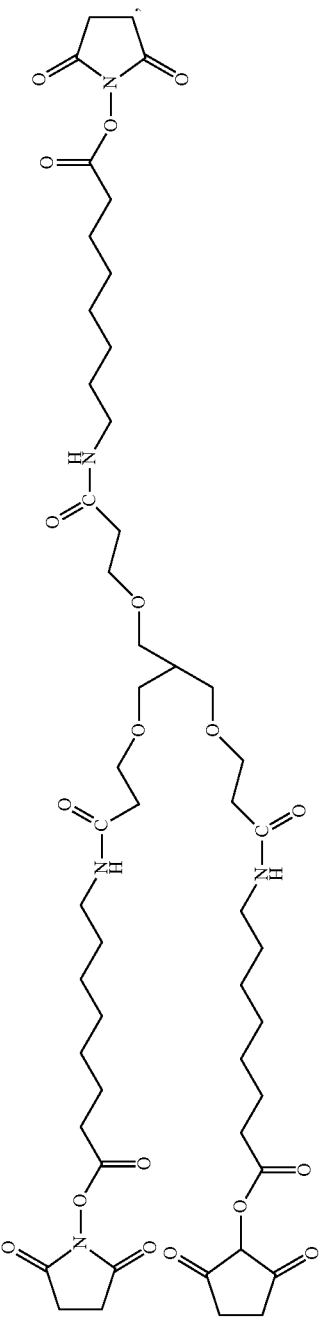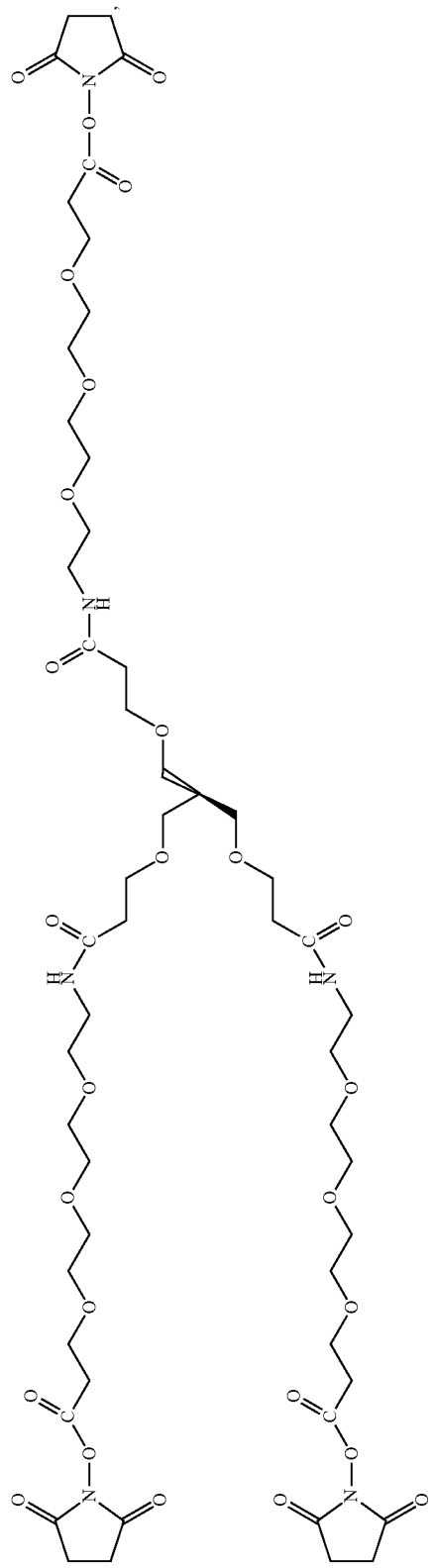

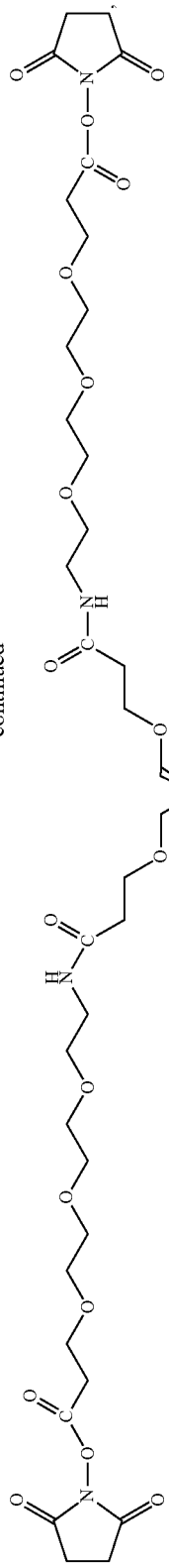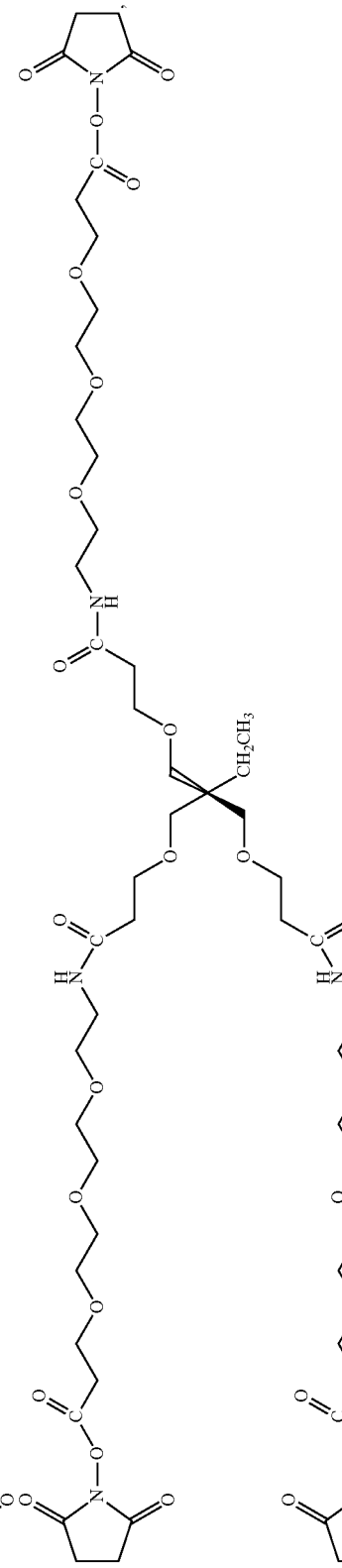

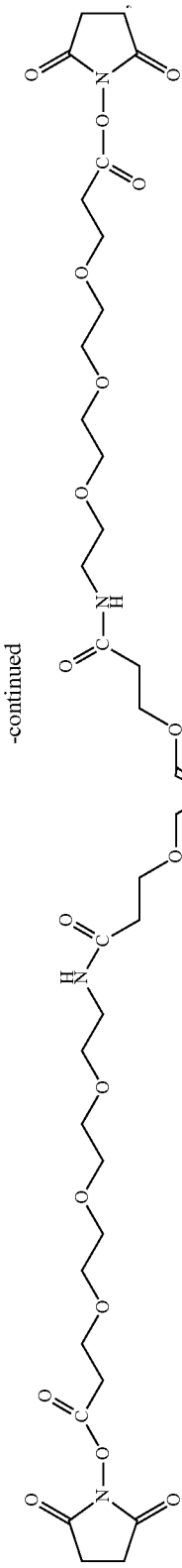
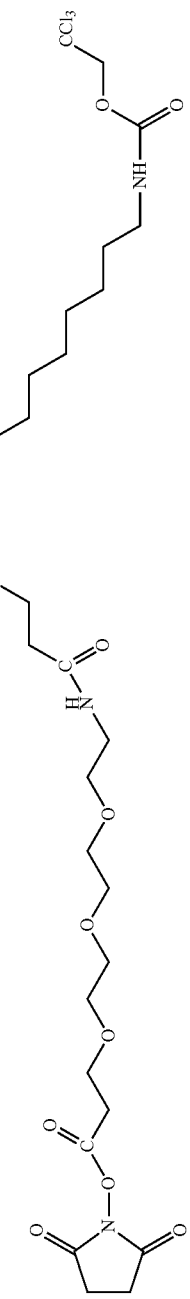
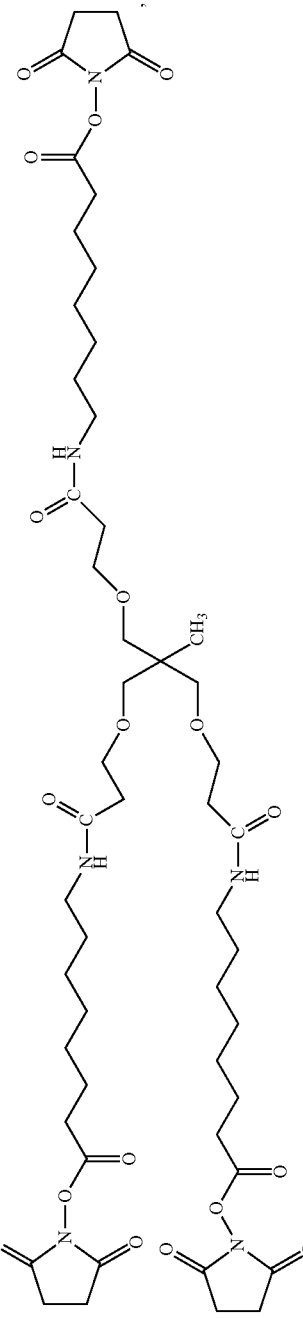
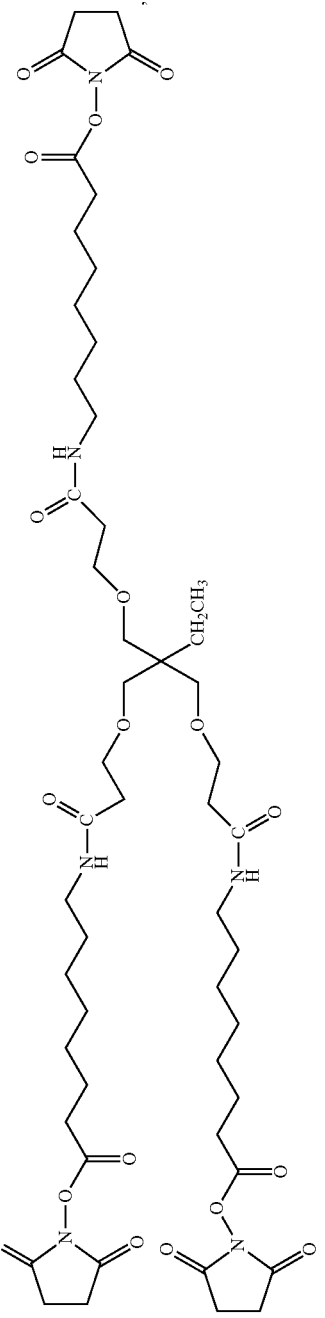

163 164
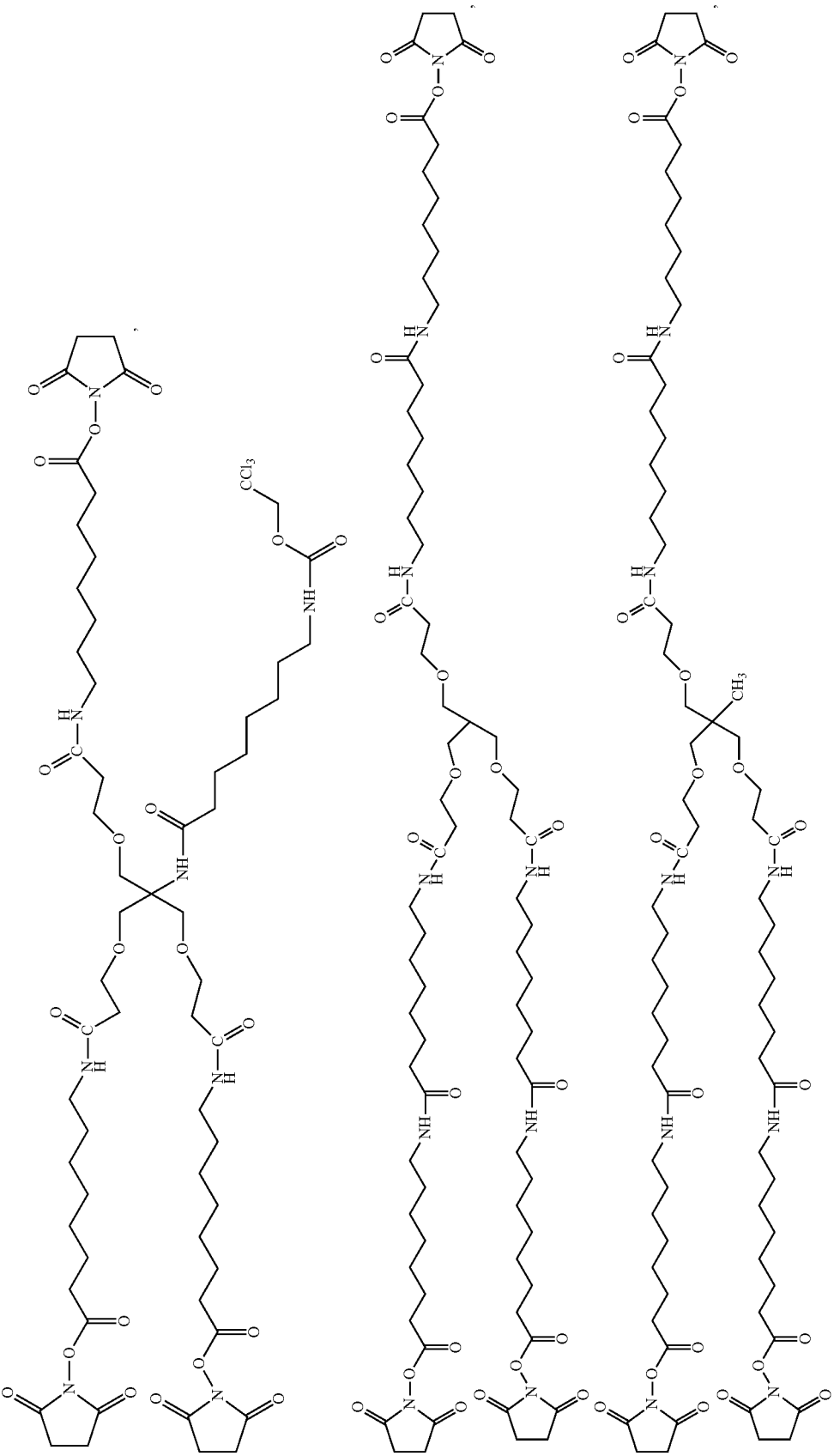

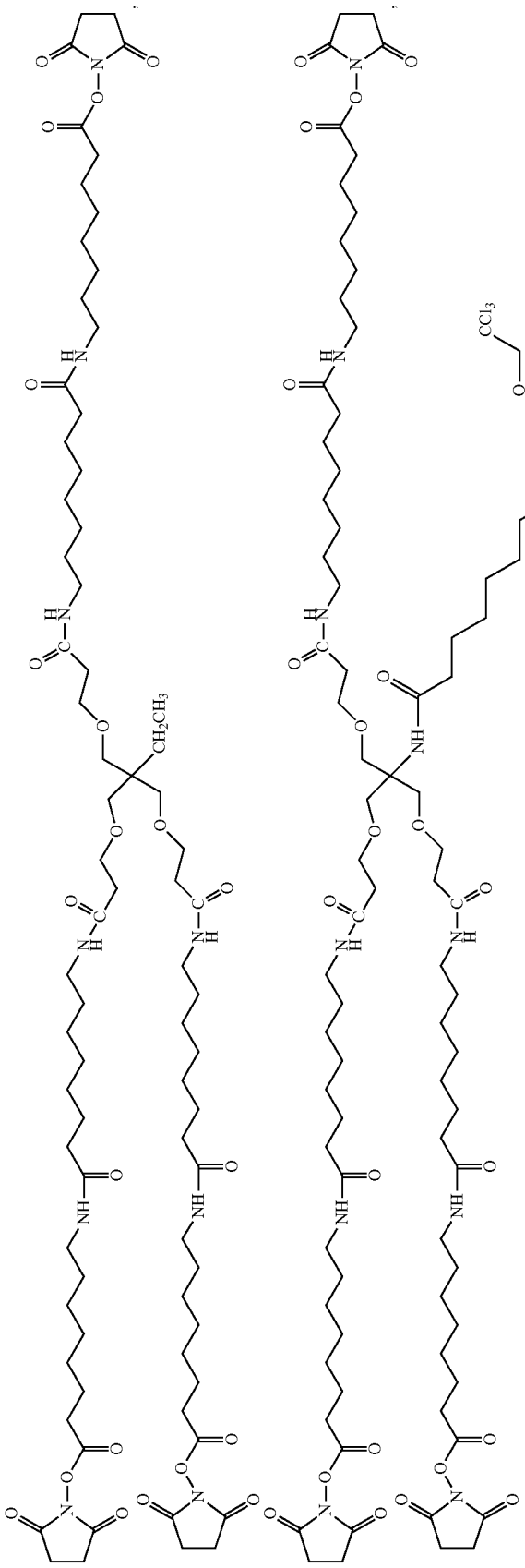
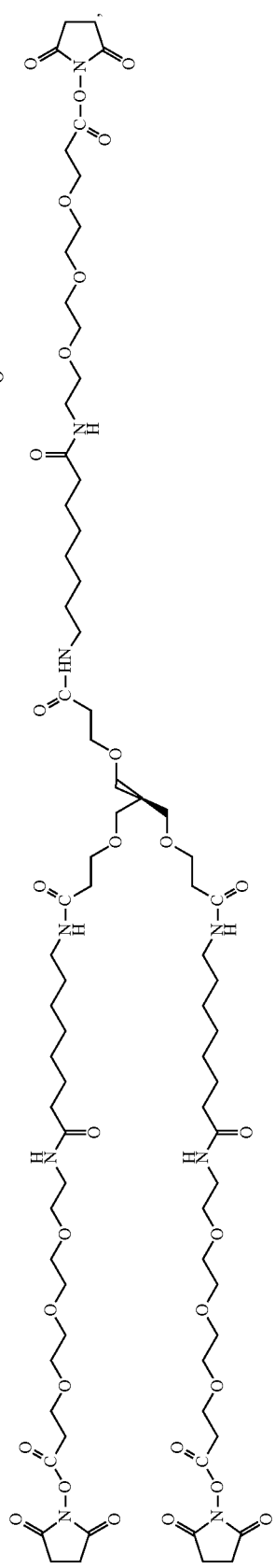

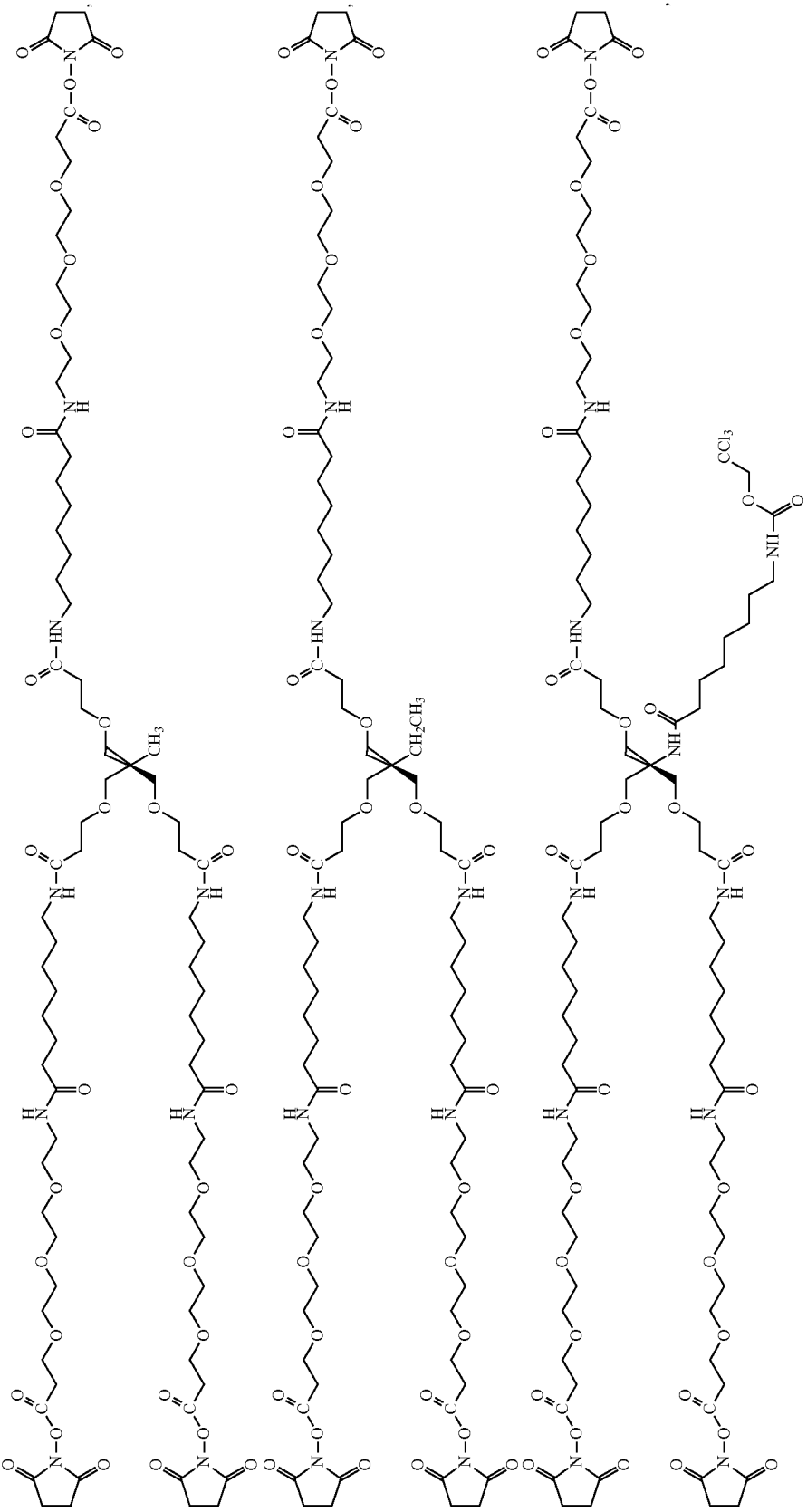

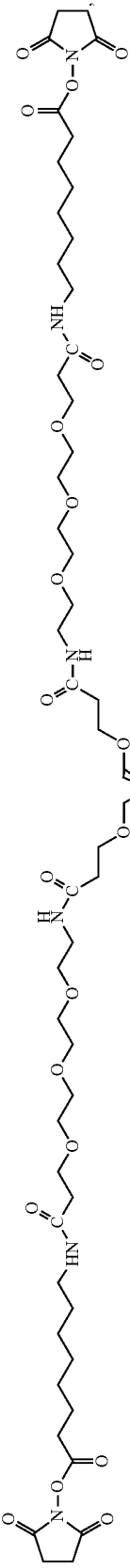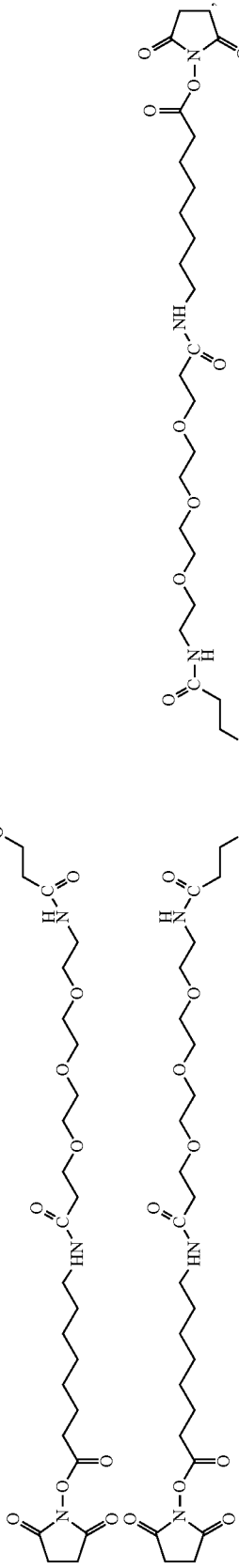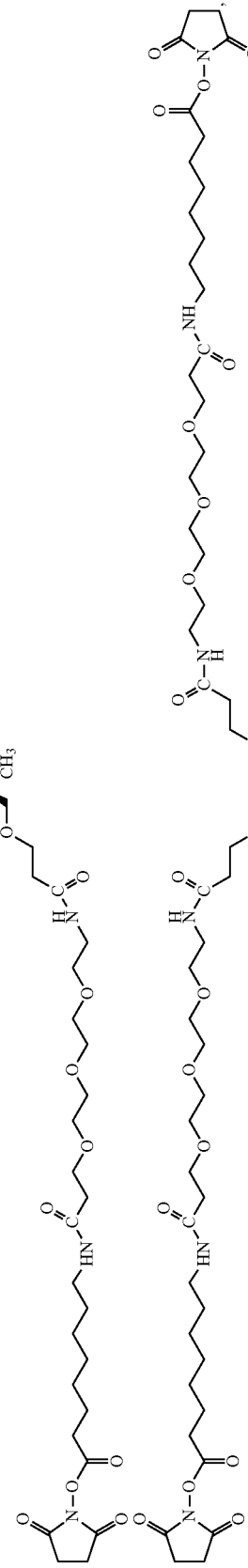

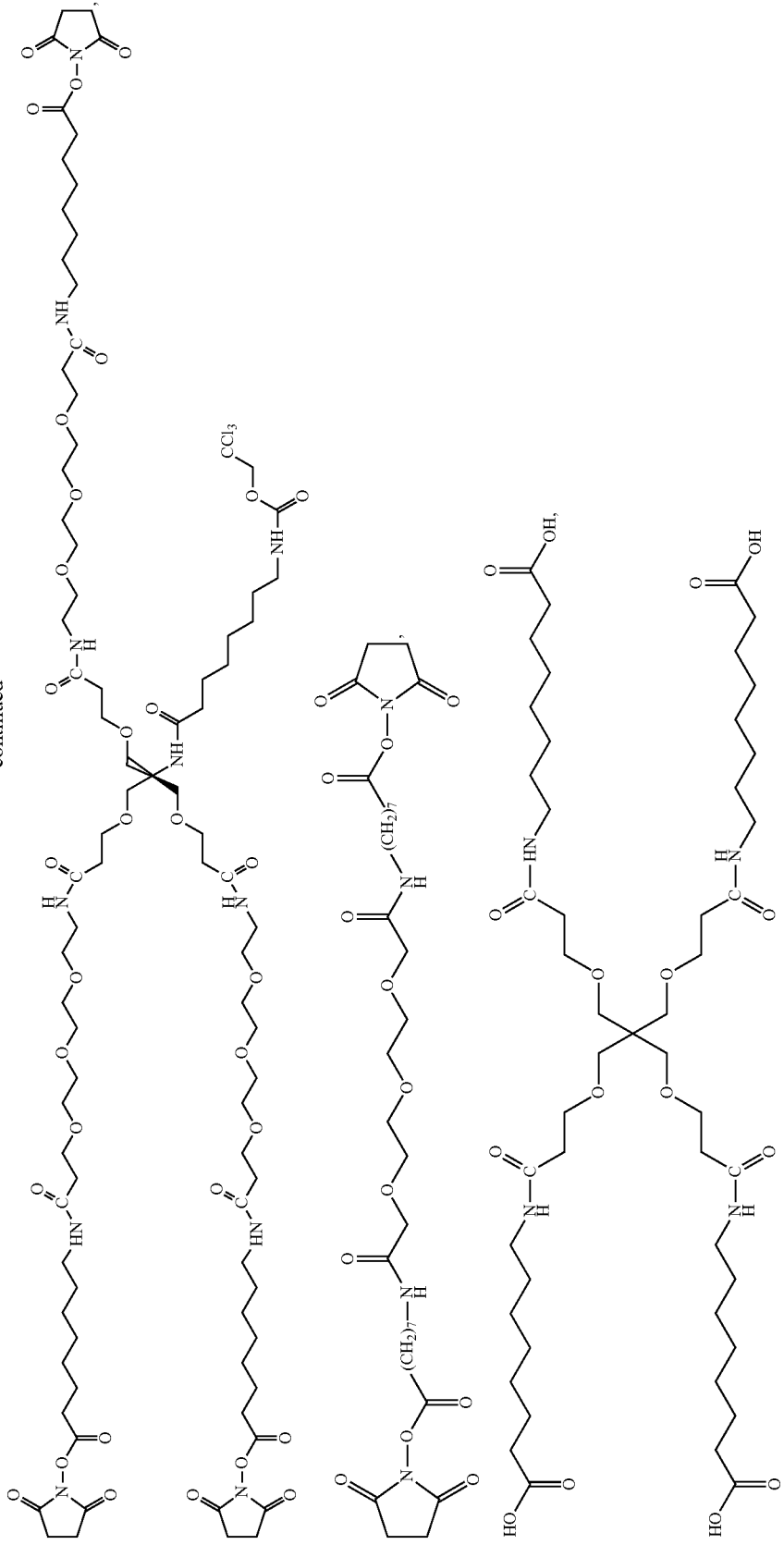

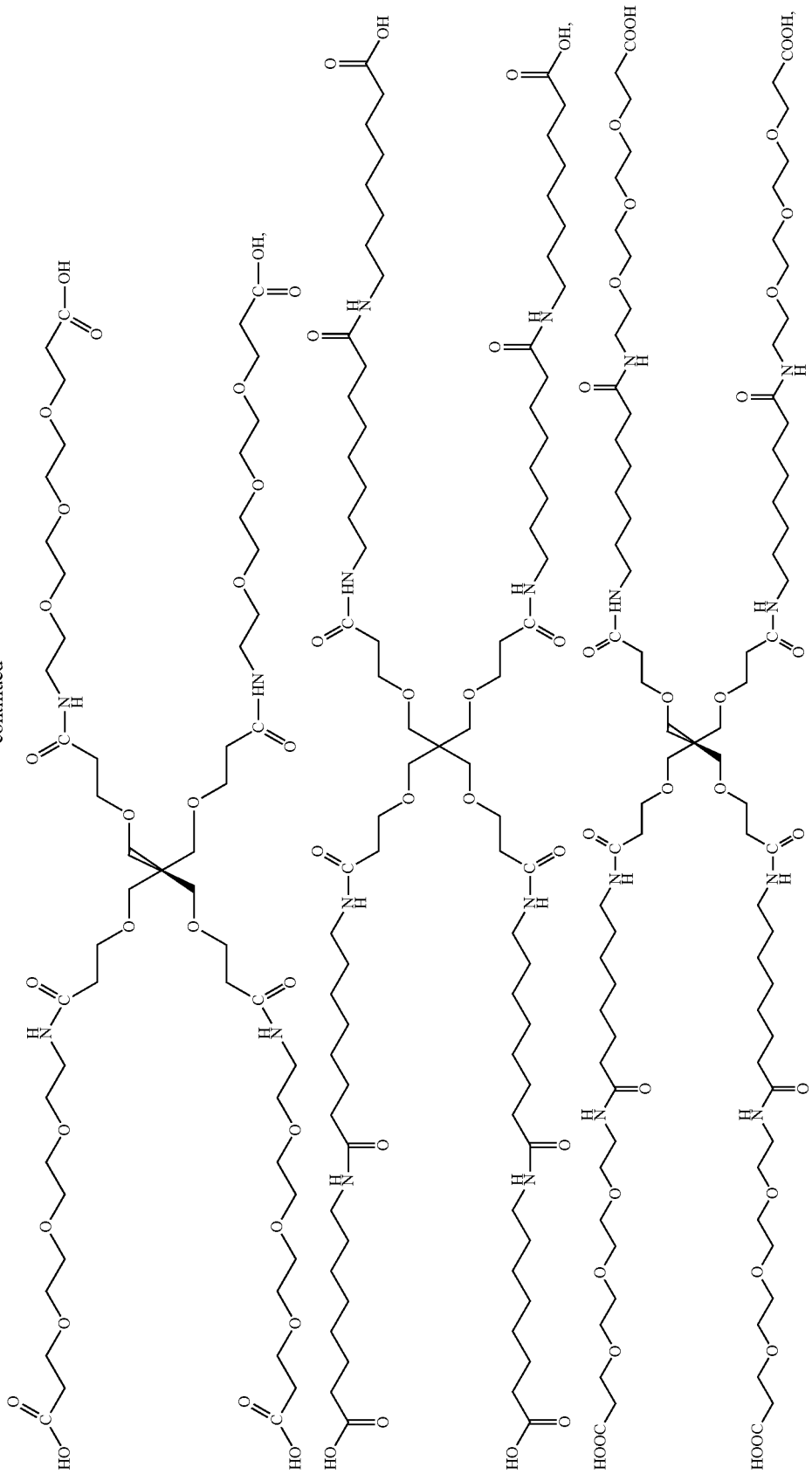

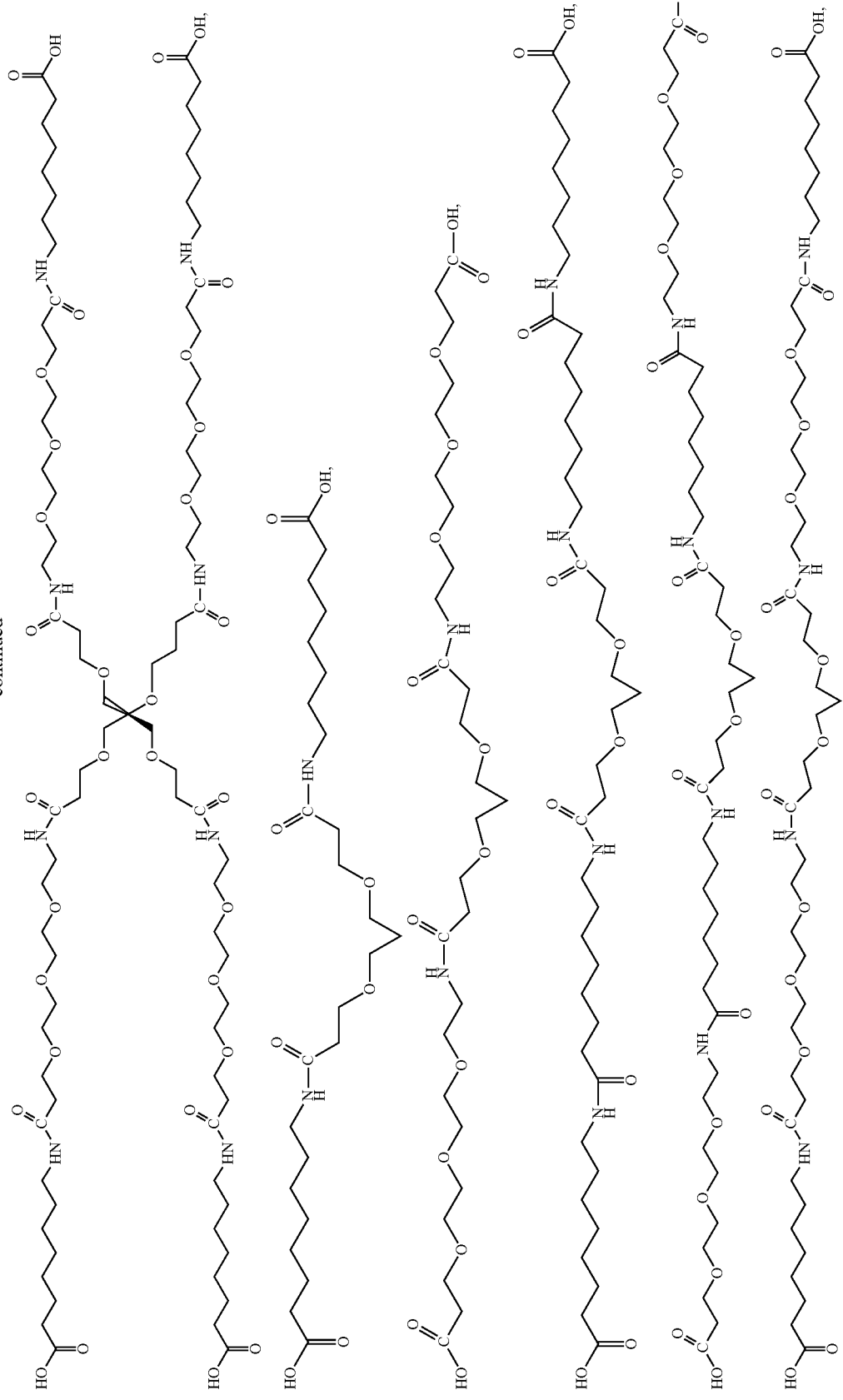

-continued
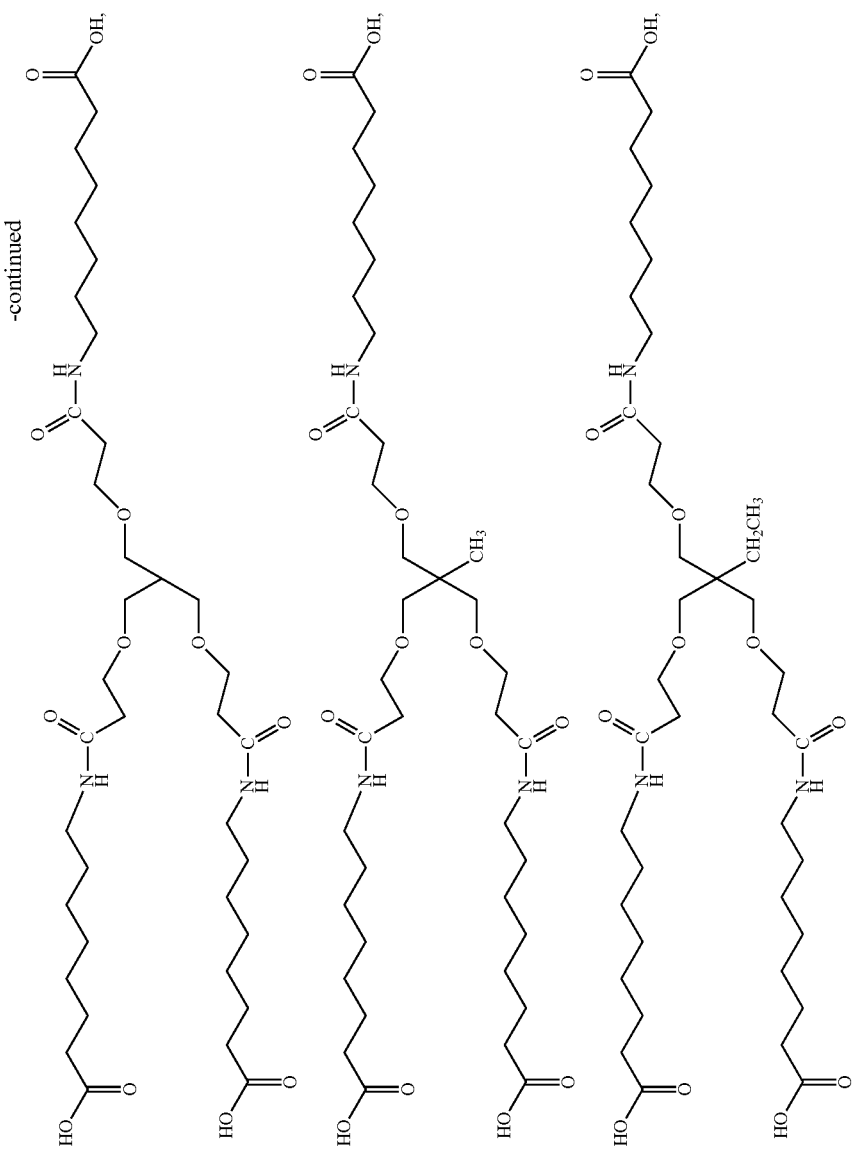

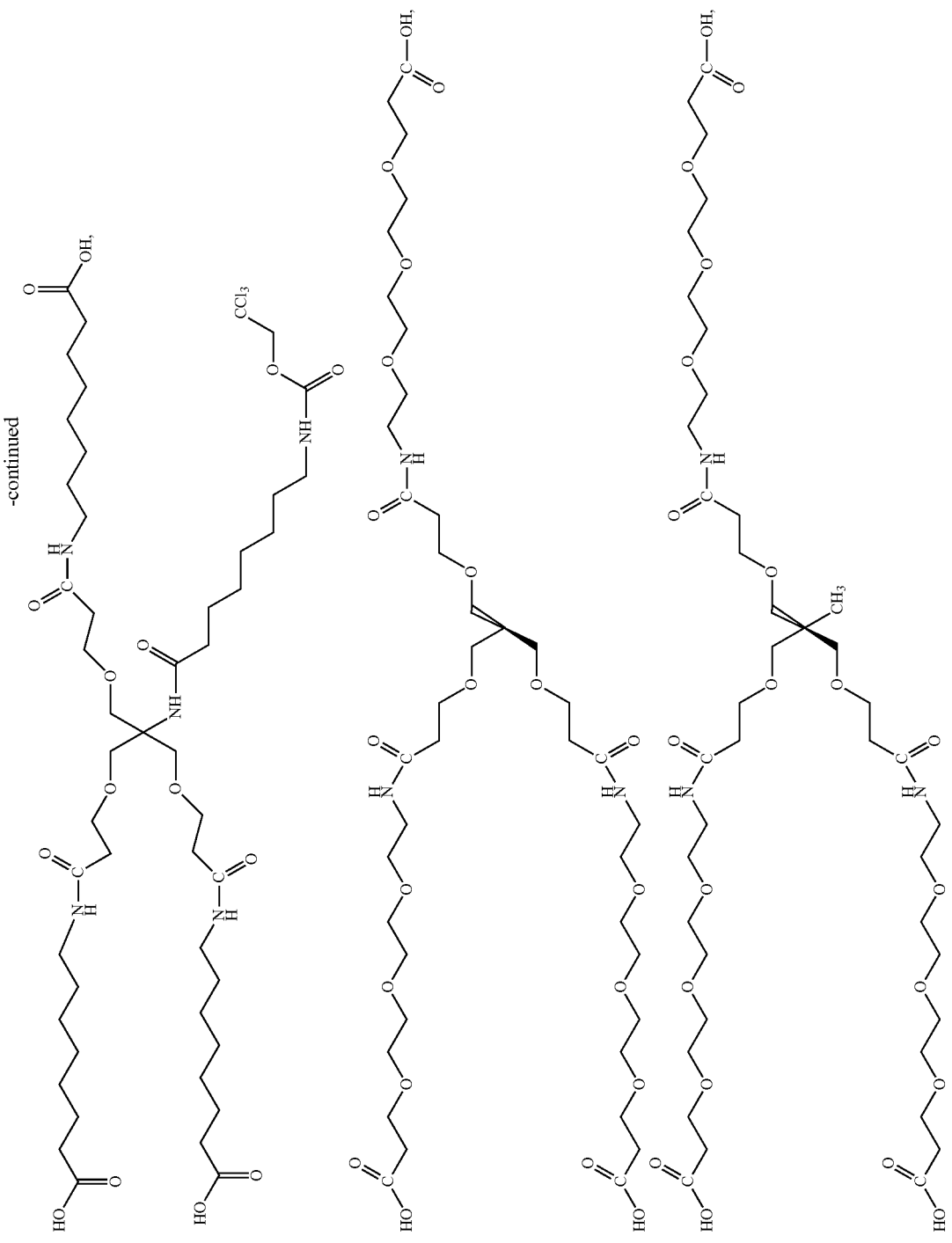

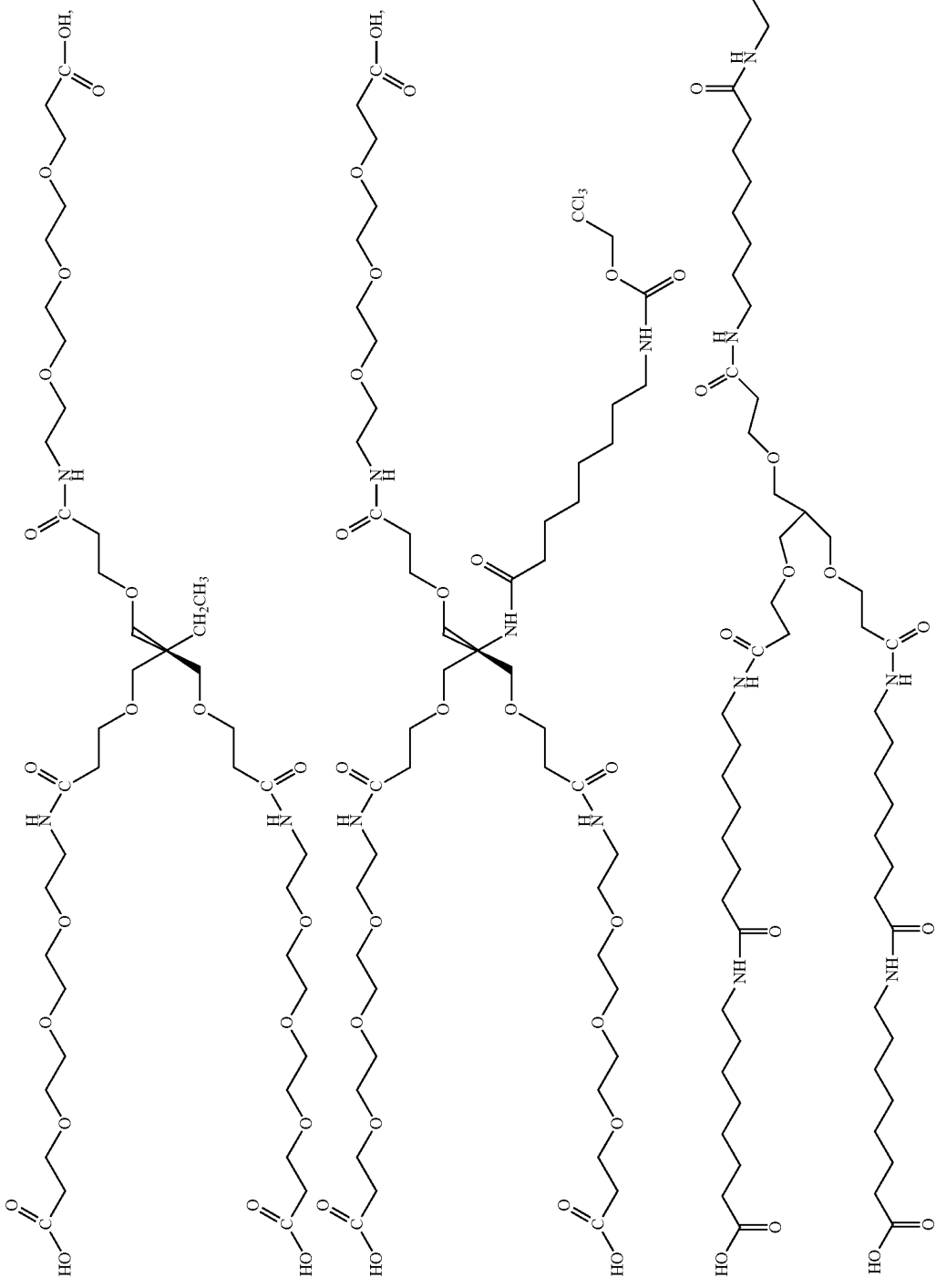

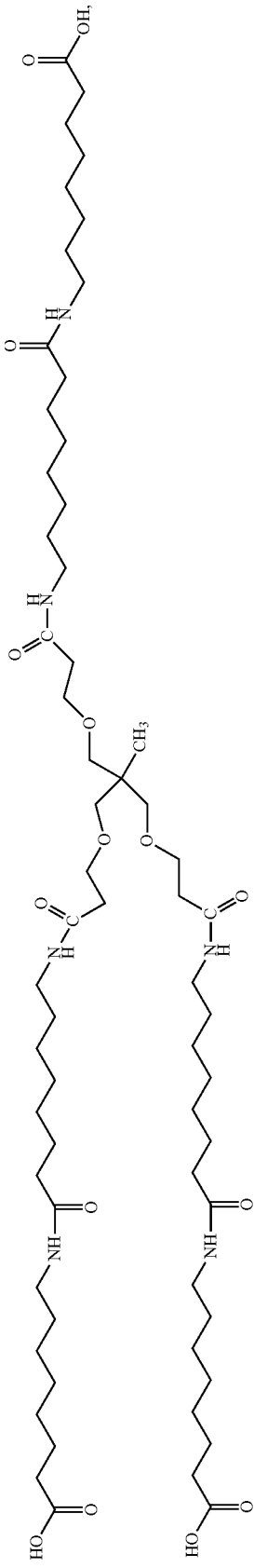
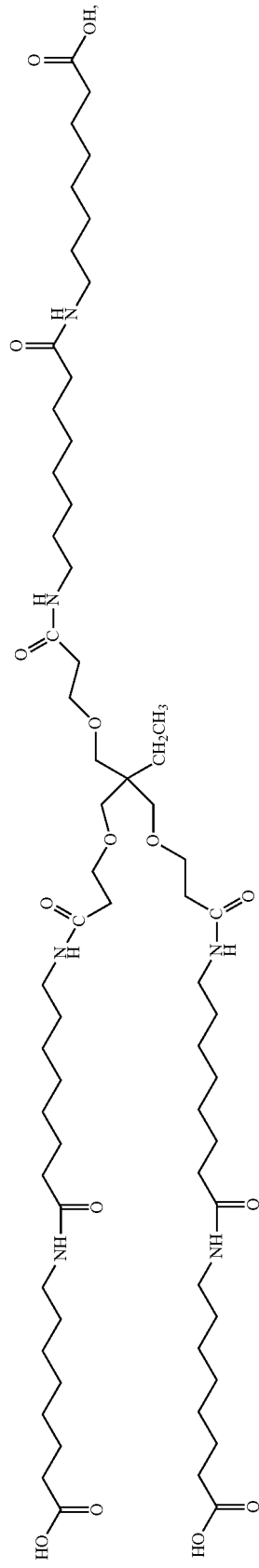
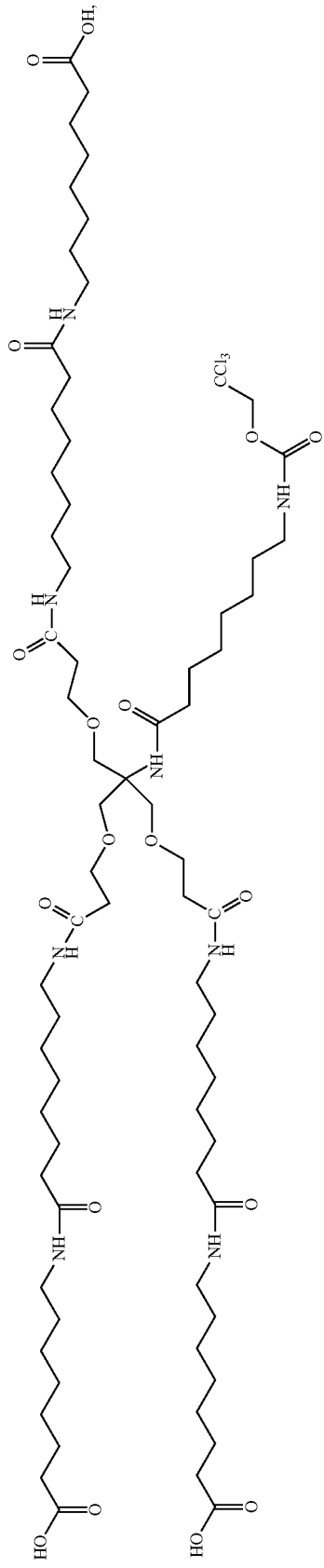

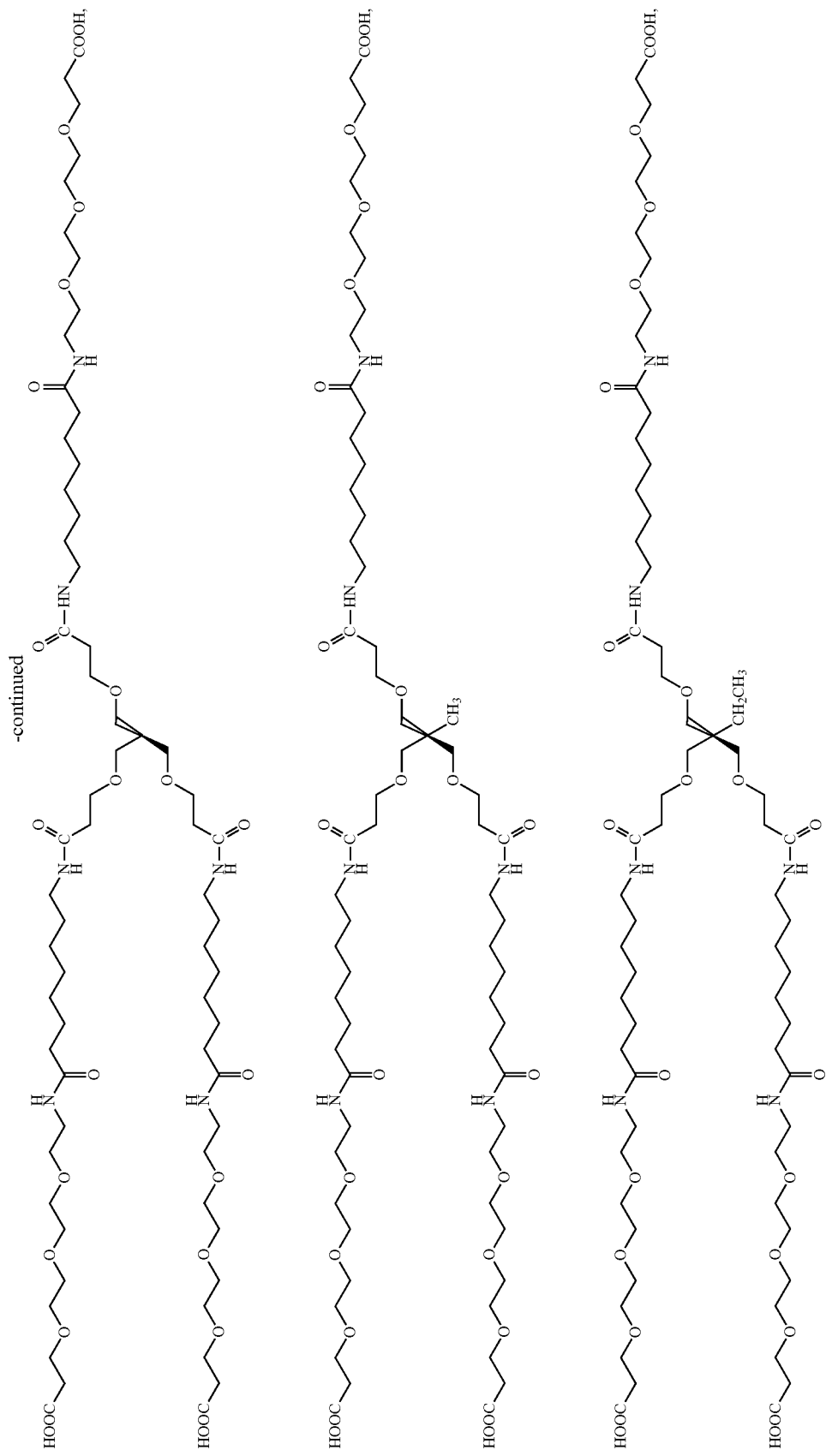

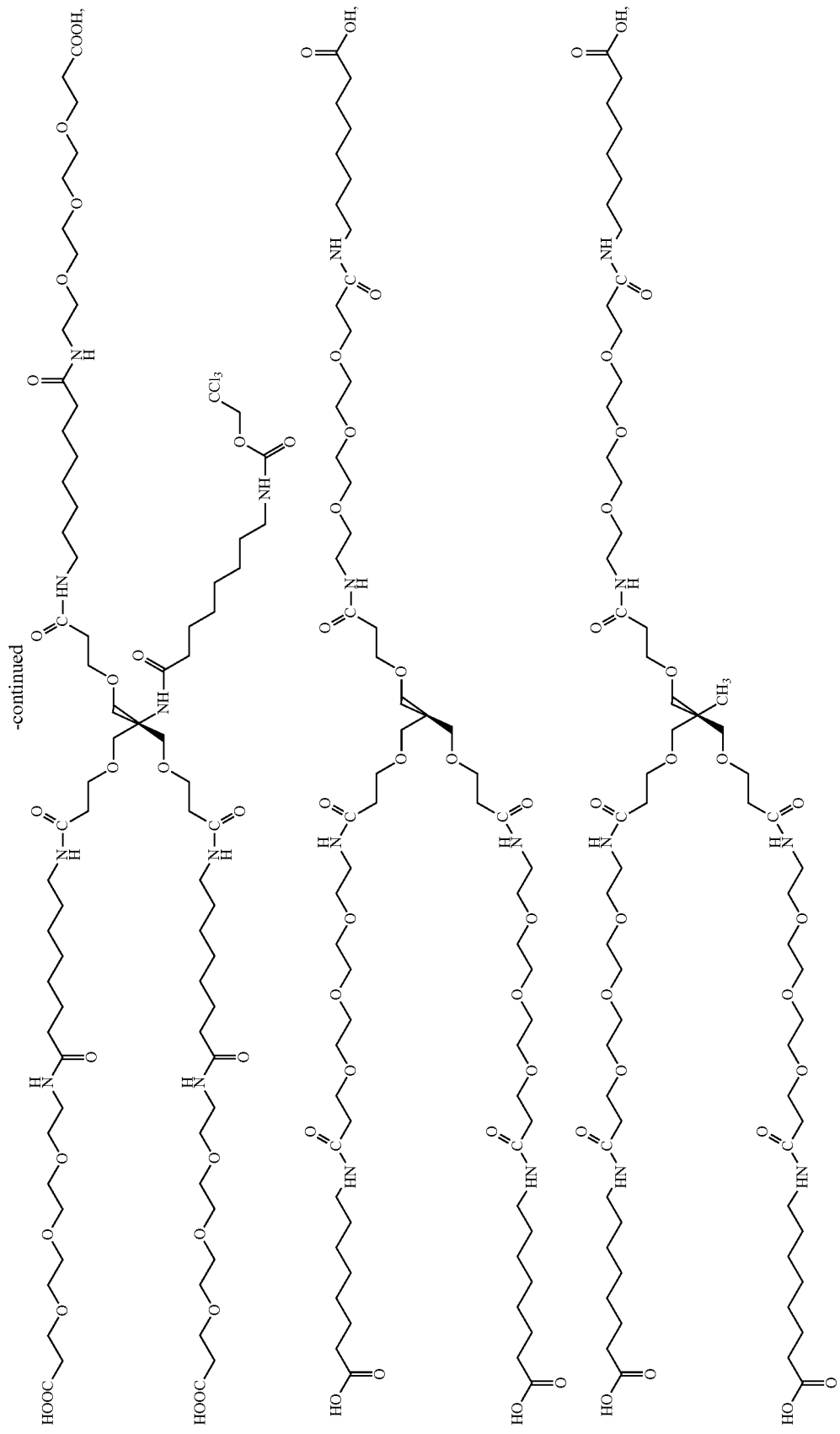

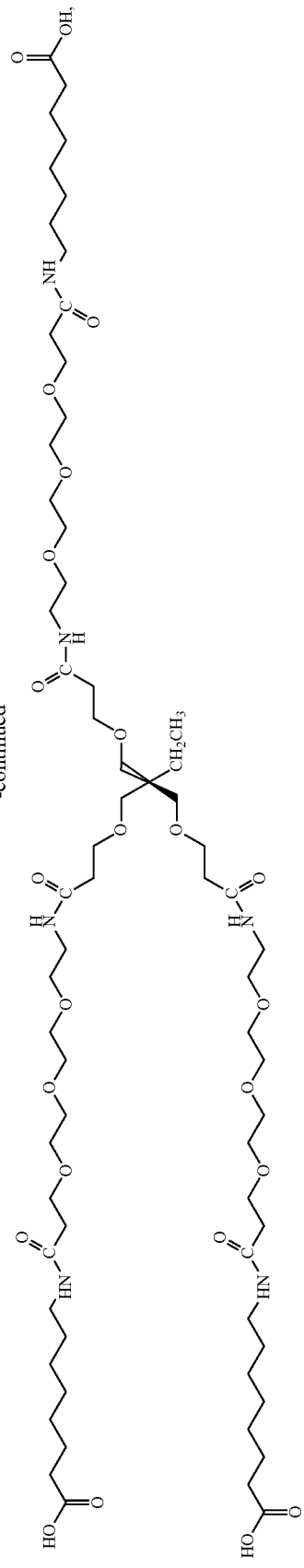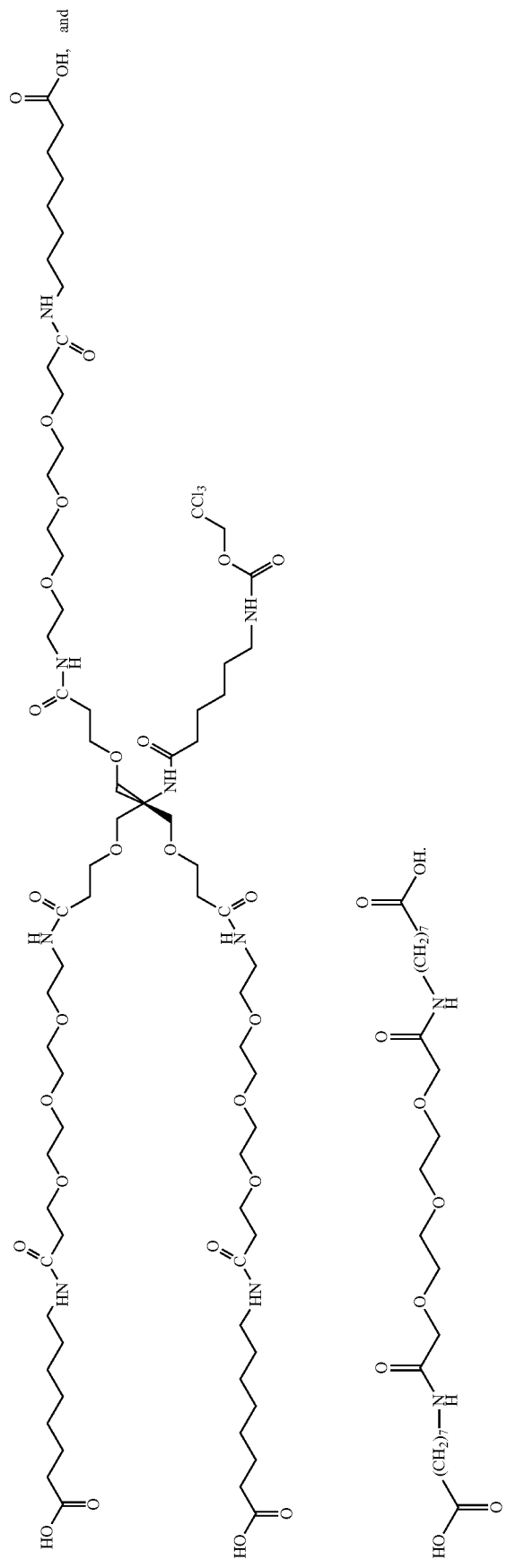

20. A compound selected from the group consisting of:
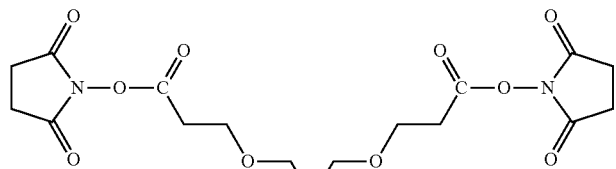
,
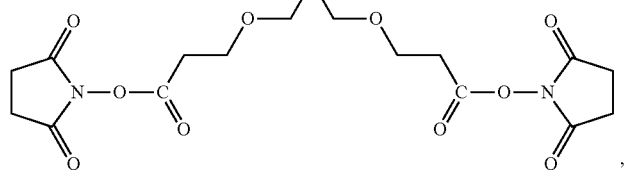
,
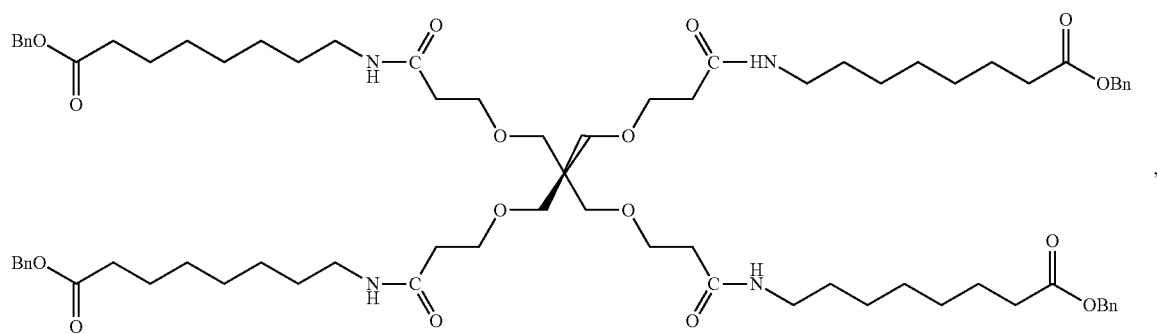
,
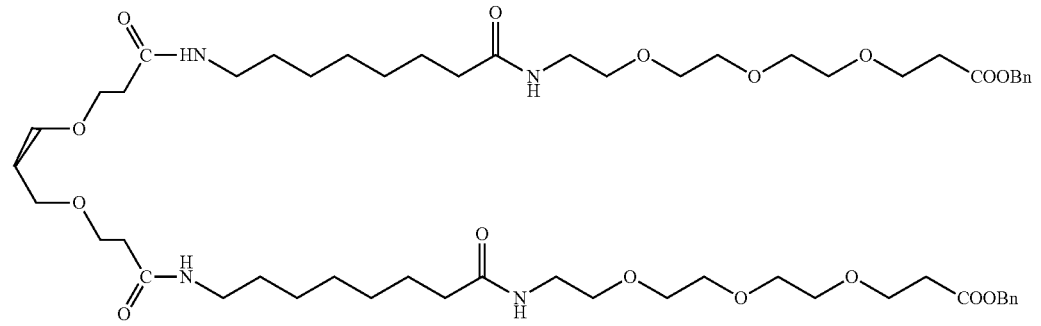
and -continued
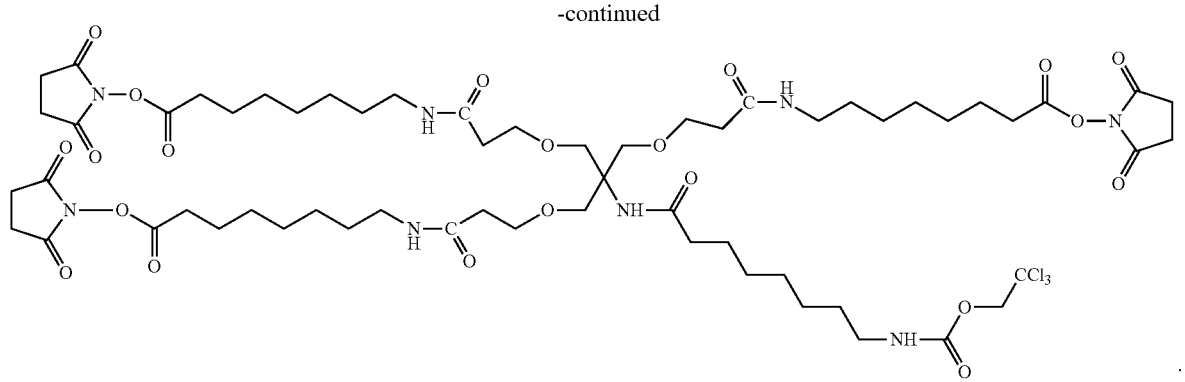
* * * * *